US 6,545,033 B1

(12) United States Patent
Dhanoa et al.

(10) Patent No.: US 6,545,033 B1
(45) Date of Patent: Apr. 8, 2003

(54) FUSED 1-(2,6-DICHLORO-4-TRIFLUOROMETHYLPHENYL)-PYRAZOLES, THE SYNTHESIS THEREOF AND THE USE THEREOF AS PESTICIDES

(75) Inventors: Daljit S. Dhanoa, Del Mar, CA (US); Sanath Meegalla, Devon, PA (US); Richard M. Soll, Lawrenceville, NJ (US); Dario Doller, Branford, CT (US); Deyou Sha, Yardley, PA (US); Ruiping Liu, Huntington, NY (US); Gary Silver, Bothell, WA (US); Yu-Kai Lee, Plainsboro, NJ (US)

(73) Assignee: 3-Dimensional Pharmaceuticals, Inc., DE (US)

( * ) Notice: Subject to any disclaimer, the term of this patent is extended or adjusted under 35 U.S.C. 154(b) by 0 days.

(21) Appl. No.: 09/680,275

(22) Filed: Oct. 6, 2000

Related U.S. Application Data
(60) Provisional application No. 60/157,858, filed on Oct. 6, 1999, and provisional application No. 60/234,273, filed on Sep. 21, 2000.

(51) Int. Cl.[7] ..................... A61K 31/416; C07D 231/54
(52) U.S. Cl. ................. 514/406; 546/275.7; 548/360.1; 548/363.1
(58) Field of Search ........................... 548/360.1, 363.1; 514/406; 246/275.7

(56) References Cited

U.S. PATENT DOCUMENTS

| 1,685,407 A | 9/1928 | Mannich |
| 3,235,360 A | 2/1966 | Soboczenski ............. 71/2.5 |
| 3,326,662 A | 6/1967 | Toyosato et al. ............ 71/2.5 |
| 3,364,227 A | 1/1968 | Robinson ................ 260/310 |
| 3,637,738 A | 1/1972 | Gschwend et al. ........ 260/311 |
| 3,818,026 A | 6/1974 | Boesch ................ 260/307 A |
| 3,836,539 A | 9/1974 | Boesch ................ 260/307 A |
| 3,846,440 A | 11/1974 | Boesch et al. ......... 260/307 A |
| 3,883,550 A | 5/1975 | Goddard ............... 260/310 C |
| 4,042,373 A | 8/1977 | Moje ......................... 71/91 |
| 4,059,434 A | 11/1977 | Wolf .......................... 71/92 |
| 4,084,055 A | 4/1978 | Fost et al. ................. 548/369 |
| 4,108,628 A | 8/1978 | Wolf .......................... 71/92 |
| 4,111,681 A | 9/1978 | Goddard .................... 71/92 |
| 4,123,252 A | 10/1978 | Goddard .................... 71/92 |
| 4,124,373 A | 11/1978 | Wolf .......................... 71/92 |
| 4,124,374 A | 11/1978 | Wolf .......................... 71/92 |
| 4,331,678 A | 5/1982 | De'Ath et al. ............. 424/273 |
| 4,335,134 A | 6/1982 | Maurer et al. ............. 424/273 |
| 4,608,080 A | 8/1986 | Haga et al. ................. 71/92 |
| 4,624,699 A | 11/1986 | Nagano et al. .............. 71/92 |
| 4,666,507 A | 5/1987 | Yanagi et al. ............... 71/92 |
| 4,670,043 A | 6/1987 | Nagano et al. .............. 71/92 |
| 4,695,312 A | 9/1987 | Hayase et al. ............... 71/92 |
| 4,740,231 A | 4/1988 | Gehring et al. ............. 71/92 |

(List continued on next page.)

FOREIGN PATENT DOCUMENTS

| DE | 39 17 469 A1 | 12/1990 | ......... C07D/401/04 |
| DE | 19511269 A1 | 10/1995 | |
| DE | 19518054 A1 | 9/1996 | |

(List continued on next page.)

OTHER PUBLICATIONS

Ando, I. et al., "Synthesis and Biological Activity of Cyclic Imide Derivatives and Related Compounds," *Agric. Biol. Chem.* 53:2001–2003, Japan Society for Bioscience, Biotechnology and Agrochemistry, Japan (1989).

(List continued on next page.)

Primary Examiner—Joseph K. McKane
Assistant Examiner—Golam M M Shameem
(74) Attorney, Agent, or Firm—Sterne, Kessler, Goldstein & Fox P.L.L.C.

(57) ABSTRACT

The present invention is directed to novel pyrazole derivatives and their use as pesticidal agents. The pyrazole derivatives have Formula I:

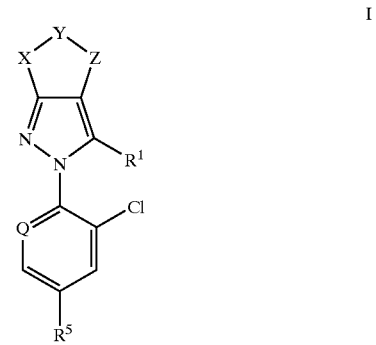

or a salt thereof, where $R^1$ is amino, hydrogen, alkyl, hydroxy, halo, alkoxy, alkylamino, dialkylamino, alkylthio, alkylsulfinyl, alkylsulfonyl, trifluoroalkylsulfinyl, trifluoroalkylsulfonyl, hydroxy, amino, trifluoromethyl, acetylamino, —OSO$_2$R$^2$, —OS(O)R$^2$, —OC(O)R$^2$, —OC(O)NHR$^2$, or —NHC(O)NHR$^2$ where $R^2$ is $C_{1-4}$ alkyl or optionally substituted aryl;

X, Y and Z are each independently $(CH)_n$, $(CR^3R^4)_n$, S, S(O), or SO$_2$, wherein n is 1–2, $R^3$ and $R^4$ are defined herein;

Q is N or C—$R^6$, wherein $R^6$ is fluoro, chloro, bromo, or iodo;

$R^5$ is halo, $C_1$–$C_6$ alkyl, $C_1$–$C_4$ alkenyl, $C_1$–$C_4$ alkoxy, $C_1$–$C_4$ alkylamino, $C_1$–$C_4$ dialkylamino, $C_1$–$C_4$ alkylthio, $C_1$–$C_4$ alkylsulfinyl, $C_1$–$C_4$ alkylsulfonyl, $C_1$–$C_4$ trifluoroalkylsulfinyl, $C_1$–$C_4$ trifluoroalkylsulfonyl, hydroxy, amino, or trifluoromethyl; and with the proviso that only one of X, Y and Z can be S, S(O) or SO$_2$.

21 Claims, No Drawings

U.S. PATENT DOCUMENTS

| | | | |
|---|---|---|---|
| 4,752,325 A | 6/1988 | Haga et al. | 71/92 |
| 4,831,149 A | 5/1989 | Haga et al. | 548/159 |
| 4,954,626 A | 9/1990 | Enomoto et al. | 544/105 |
| 4,990,174 A | 2/1991 | Rueb et al. | 71/92 |
| 4,997,472 A | 3/1991 | Rueb et al. | 71/92 |
| 5,035,740 A | 7/1991 | Poss | 71/93 |
| 5,049,181 A | 9/1991 | Pissiotas et al. | 71/90 |
| 5,104,442 A | 4/1992 | Schütze et al. | 71/92 |
| 5,104,994 A | 4/1992 | Roberts et al. | 548/376 |
| 5,134,155 A | 7/1992 | Connolly et al. | 514/403 |
| 5,185,025 A | 2/1993 | Moedritzer et al. | 504/282 |
| 5,232,940 A | 8/1993 | Hatton et al. | 514/407 |
| 5,306,694 A | 4/1994 | Phillips et al. | 504/253 |
| 5,387,693 A | 2/1995 | Connolly et al. | 548/360.1 |
| 5,464,811 A | 11/1995 | Hirai et al. | 504/281 |
| 5,487,976 A | 1/1996 | Soderlund et al. | 435/7.21 |
| 5,554,580 A | 9/1996 | Fischer et al. | 504/281 |
| 5,637,607 A | 6/1997 | Pilato et al. | 514/404 |
| 5,707,936 A | 1/1998 | Oberdorf et al. | 504/253 |
| 5,814,652 A | 9/1998 | Wu | 514/404 |
| 5,849,778 A | 12/1998 | Heil et al. | 514/403 |
| 5,869,517 A | 2/1999 | Müller et al. | 514/407 |
| 5,885,607 A | 3/1999 | Jeannin | 424/411 |
| 5,939,558 A | 8/1999 | Heistracher et al. | 548/360.1 |
| 6,069,157 A | 5/2000 | Banks | 514/341 |
| 6,083,519 A | 7/2000 | Jeannin | 424/411 |
| 6,239,076 B1 | 5/2001 | Ryu et al. | 504/271 |
| 6,335,357 B1 | 1/2002 | Okui et al. | 514/404 |

FOREIGN PATENT DOCUMENTS

| | | | |
|---|---|---|---|
| DE | 19544799 A1 | 6/1997 | |
| DE | 197 56 115 A1 | 6/1999 | |
| EP | 0 138 527 A2 | 4/1985 | |
| EP | 0 152 286 A1 | 8/1985 | |
| EP | 0 234 119 A1 | 9/1987 | |
| EP | 0 350 311 A1 | 1/1990 | |
| EP | 0 398 499 A2 | 11/1990 | |
| EP | 0 412 849 A2 | 2/1991 | |
| EP | 0 418 016 A1 | 3/1991 | |
| EP | 0 558 999 A2 | 9/1993 | |
| EP | 0 659 745 A1 | 6/1995 | |
| EP | 0 745 684 A1 | 12/1996 | |
| EP | 0 846 686 A1 | 6/1998 | |
| FR | 2301250 | 10/1976 | |
| GB | 1 519 906 | 8/1978 | C07D/231/54 |
| JP | 59181259 | 10/1984 | |
| JP | 6041667 | 3/1985 | |
| JP | 60-233061 | 11/1985 | |
| JP | 61-165373 | 7/1986 | |
| JP | 63-287766 | 11/1988 | |
| JP | 8208620 | 8/1996 | |
| KR | 917886 | 10/1991 | |
| WO | WO 92/13451 | 8/1992 | |
| WO | WO 93/06089 | 4/1993 | |
| WO | WO 93/19054 | 9/1993 | |
| WO | WO 93/21160 | 10/1993 | |
| WO | WO 94/13643 | 6/1994 | |
| WO | WO 94/13644 | 6/1994 | |
| WO | WO 94/13661 | 6/1994 | |
| WO | WO 94/13677 | 6/1994 | |
| WO | WO 94/21606 | 9/1994 | |
| WO | WO 95/22530 | 8/1995 | |
| WO | Wo 95/33727 | 12/1995 | |
| WO | WO 98/22442 A2 | 5/1998 | |

OTHER PUBLICATIONS

Baraldi, P.G. et al., "A Mild One–Pot Synthesis of Thieno [3,4–c]pyrazoles and Their Conversion into Pyrazole Analogs of o–Quinodimethane," *Synthesis* (9):1331–1334, Thieme, New York, NY (Sep. 1998).

Bardou, L. et al., "XVI.—Pyrazoles bicycliques," *Bulletin de la Société Chimique de France* (1):289–294, Société Chimique de France, Paris, France (1967).

Bauer, V.J. et al., "Synthesis, Alkylation, and Oxidation of Thieno[3,4–c]—and —[3,2–c]pyrazoles," *J. Med. Chem.* 14:454–456, American Chemical Society, Washington, DC (1971).

Chou, T.–s. and Chang, R.–C., "A Novel Route to the Preparation of Pyrazole Analogues of o–Xylylene," *J. Org. Chem.* 58:493–496, American Chemical Society, Washington, DC (1993).

Chou, T.–s. and Chang, R.–C., "Synthesis and Reactions of N–Substituted Pyrazolo–3–Sulfolenes," *Heterocycles* 36:2839–2850, Elsevier Science, New York, NY (1993).

Connolly, P.J. et al., "HMG–CoA Reductase Inhibitors: Design, Synthesis, and Biological Activity of Tetrahydroindazole–Substituted 3,5–Dihydroxy–6–heptenoic Acid Sodium Salts," *J. Med. Chem.* 36:3674–3685, American Chemical Society, Washington, DC (1993).

Duncan, D.C. et al., "The Preparation of N–Carboalkoxypyrazoles and N–Phenylpyrazoles from C($\alpha$)–Dianions of Carboalkoxyhydrazones and Phenylhydrazones," *J. Heterocyclic Chem.* 24:555–559, Hetero Corporation, Provo, Utah (1987).

Elguero, J. et al., "XIV.—Étude UV de pyrazoles," *Bulletin de la Société Chimique de France* (12):3744–3752, Société Chimique de France, Paris, France (1966).

Jacquier, R. and Maury, G., "(Dinitro–2', 4' phényl)–1 pyrazoles dérivant de l'hydroxyméthyléne–2 cycloheptanone et de l'hydroxymèthyléne–3 camphre (Note de Laboratorie)," *Bulletin de la Société Chimique de France* (1):295–297, Société Chimique de France, Paris, France (1967).

Jacquier, R. and Maury, G., "XVII.—Synthèses et étude des (dinitro–2',4'phényl)–1 pyrazoles isomères dérivant d'acétyl–2 cyclanones (Première partie)," *Bulletin de la Société Chimique de France* (1):306–315, SociétéChimique de France, Paris, France (1967).

Jacquier, R. and Maury, G., "XIX.—Synthèses et étude des (dinitro–2',4'phényl)–1 pyrazoles isomères dérivant d'acétyl–2 cyclanones (Deuxième partie)," *Bulletin de la Société Chimique de France* (1):316–320, Société Chimique de France, Paris, France (1967).

Lyga, J.W. et al., "Synthesis, Mechanism of Action, and QSAR of Herbicidal 3–Substituted–2–aryl–4,5,6,7–tetrahyroindazoles," *Pestic. Sci* 42:29–36, John Wiley & Sons, Inc., New York, NY (1994).

Malik, O.P. et al., "Synthesis of 2,3–Substituted 4,5,6, 7–Tetrahydro–2H–Indazoles; 2,4,5,6,7,8–Hexahydrocyclohepta(C) Pyrazoles and Their ω–t–Aminoalkyl Enol Ethers," *Harayana agric. Univ. J. Res.* 10:218–221 (1980).

Schenone, S. et al., "2–Aryl–3–Phenylamino–4, 5–Dihydro–2H–Benz[g]indazoles with Antiarrhythmic and Local Anaesthetic Activities," *Il Farmaco* 50:179–182, Società Chimica Italiana, Rome, Italy (1995).

Strakova, I.A. et al., "Synthesis and Reactions of 1–(2–Pyridyl)–3–Methyl–4–Chloro–5–Formyl–6,7–Dihydroindazoles," *Chem. Heterocyclic Compounds* 34:669–673, Plenum Publishing Corporation, London, England (1998).

Wang, Q. et al., "On the Reaction of 1–Aza–2–azoniaallene Salts with Acetylenes," *Chem. Ber.* 127:541–547, VCH Verlagsgesellschaft mbH, Weinheim, Germany (1994).

Williams, R.P. et al., "Synthesis and Alkylation of Tetrahydrocyclopentapyrazolols," *J. Med. Chem.* 13:773–775, American Chemical Society, Washington, DC (1970).

Yoichi, I., "Phenylpyrazole Derivative and Noxious Life Controlling Agent," *Patent Abstracts of Japan*, Publications No. 05262741, European Patent Office (1993).

Yukiaki, M., "Aminopyrazole Derivative, Its Production and Use," *Patent Abstracts of Japan*, Publication No. 08208620, European Patent Office (1996).

Yukiaki, M., "Pyrazole Derivative, Its Use," *Patent Abstracts of Japan*, Publication No. 08311036, European Patent Office (1996).

Dialog File 351, Accession No. 1662172, Derwent WPI English language abstract for FR 2,301,250 (Document AN5).

CAPLUS Accession No. 1967:473550, Document No. 67:73550, CAPLUS English language abstract, American Chemical Society, Washington, DC, for Document AS5, Bardou, L. et al., *Bulletin de la Société Chimique de France* (1):289–294, Société Chimique de France, Paris, France (1967).

Dialog File 351, Accession No. 4501508, Derwent WPI English language abstract for JP 60–233061 (Document AL6).

Dialog File 351, Accession No. 4732434, Derwent WPI English language abstract for JP 61–165373 (Document AM6).

Dialog File 351, Accession No. 7746781, Derwent WPI English language abstract for JP 63–287766 (Document AN6).

Dialog File 351, Accession No. 9588344, Derwent WPI English language abstract for EP 0 558 999 A2 (Document AO6).

CAPLUS Accession No. 1967:80664, Document No. 66:80664, CAPLUS English language abstract, American Chemical Society, Washington, DC, for Document AS7, Elguero, J. et al., *Bulletin de la Société Chimique de France* (12):3744–3752, Société Chimique de France, Paris, France (1966).

CAPLUS Accession No. 1967:403028, Document No. 67:3028, CAPLUS English language abstract, American Chemical Society, Washington, DC, for Document AT7, Jacquier, R. and Maury, G., *Bulletin de la Société Chimique de France* (1):295–297, Société Chimique de France, Paris, France (1967).

Dialog File 351, Accession No. 12565980, Derwent WPI English language abstract for DE 197 56 115 A1 (Document AP7).

CAPLUS Accession No. 1967:508588, Document No. 67:108588, CAPLUS English language abstract, American Chemical Society, Washington, DC, for Document AR8, Jacquier, R. and Maury, G., *Bulletin de la Société Chimique de France* (1):306–315, Société Chimique de France, Paris, France (1967).

CAPLUS Accession No. 1967:473551, Document No. 67:73551, CAPLUS English language abstract, American Chemical Society, Washington, DC, for Document AS8, Jacquier, R. and Maury, G., *Bulletin de la Société Chimique de France* (1):316–320, Société Chimique de France, Paris, France (1967).

Cole, L.M. et al., "Action of Phenylpyrazole Insecticides at the GABA–Gated Chloride Channel," *Pesticide Biochem. Physiol.* 46:47–54 Academic Press, New York, NY (1993).

Finkelstein, B.L. and C.J. Strock, "Synthesis and Insecticidal Activity of Novel Pyrazole Methanesulfonates," *Pestic. Sci.* 50:324–328 John Wiley & Sons, New York, NY (1997).

Dialog File 351, Accession No. 4146500, Derwent WPI English language abstract for JP 59181259 (Document AL1).

Dialog File 351, Accession No. 4264102, Derwent WPI English language abstract for JP 6041667 (Document AM1).

Dialog File 351, Accession No. 9260868, Derwent WPI English language abstract for KR 917886 (Document AN2).

Dialog File 351, Accession No. 10324917, Derwent WPI English language abstract for EP 0 659 745 A1 (Document AL4).

Dialog File 351, Accession No. 10392384, Derwent WPI English language abstract for WO 95/22530 (Document AM4).

Dialog File 351, Accession No. 10451076, Derwent WPI English language abstract for DE 19511269 A1 (Document AN4).

Dialog File 351, Accession No. 10925014, Derwent WPI English language abstract for JP 8208620 (Document AO4).

Dialog File 351, Accession No. 10916684, Derwent WPI English language abstract for DE 19518054 A1 (Document AP4).

Dialog File 351, Accession No. 11321362, Derwent WPI English language abstract for DE 19544799 A1 (Document AL5).

Dialog File 351, Accession No. 8482044, Derwent WPI English language abstract for DE 39 17 469 A1 (Document AM8).

FUSED 1-(2,6-DICHLORO-4-TRIFLUOROMETHYLPHENYL)-PYRAZOLES, THE SYNTHESIS THEREOF AND THE USE THEREOF AS PESTICIDES

CROSS REFERENCE

This application claims benefit under 35 U.S.C § 119(e) of U.S. Provisional Application Ser. No. 60/157,858, filed Oct. 6, 1999; and U.S. Provisional Application Ser. No. 60/234,273, filed Sep. 21, 2000, the contents of which are fully incorporated by reference herein.

BACKGROUND OF THE INVENTION

1. Field of the Invention

The present invention is in the field of substituted 1-arylpyrazole compounds, their synthesis and their use as pest GABA receptor inhibitors and pesticides.

2. Related Art

γ-Aminobutyric acid (GABA) receptors are intrinsic membrane glycoproteins in vertebrate and invertebrate neuronal tissues that are members of the ligand-gated ion channel superfamily of receptors. GABA receptors play a major role in the inhibition of central nervous system (CNS) neuronal activity due to the widespread distribution of GABA-releasing and GABA-receptive neurons.

Vertebrate GABA receptors can be divided into two major classes: the $GABA_A$ and $GABA_C$ subtypes, and $GABA_B$ receptor subtype, which are distinguished by differences in their effector mechanisms and pharmacology (Knapp, R. J., et al., Neurochem. Res. 15:105–112 (1990)). $GABA_A$ and $GABA_C$ receptors are transmitter-operated chloride channels that are activated by GABA to open their chloride channel while $GABA_B$ receptors are thought to mediate changes in cyclic AMP levels through the activation of phospholipase activity (Eldefrawi, A. T. and Eldefrawi, M. E., FASEB J. 1:262–271 (1987); Knapp, R. J., et al., Neurochem. Res. 15:105–112 (1990)). The $GABA_A$ receptor and its associated chloride ion channel make up the so-called $GABA_A$ receptor-channel complex.

GABA is the endogenous ligand for the $GABA_A$ receptor of the $GABA_A$-complex, and is the major inhibitory neurotransmitter in the vertebrate brain, in the insect CNS and at insect neuromuscular junctions (Enna et al., In: Benzodiazepine/GABA Receptors and Chloride Channels: Structural and Functional Properties, Alan R. Liss, Inc., New York, pp. 41–56 (1986); Sattelle, D. B., Adv. Insect Physiol. 22:1–113 (1990)). GABA binding to its receptor stimulates chloride ion conductance through the associated chloride ion channel to inhibit synaptic transmission (Knapp, R. J., et al., Neurochem. Res. 15:105–112 (1990); U.S. Pat. No. 5,487,976). When two molecules of GABA bind at sites on the receptor, the chloride channel undergoes a conformational change and opens, allowing chloride ions to flow passively down the electrochemical gradient into the neuron. An influx of chloride into the cell causes a change in the membrane potential, usually a hyperpolarization, which results in an inhibition of the nerve impulse. Blockage of the GABA-gated chloride channel reduces neuronal inhibition, which leads to hyper-excitation of the CNS, resulting in convulsions and death. In contrast, irreversible hyperactivation of the channel suppresses neuronal activity, resulting in ataxia, paralysis, coma and death (Bloomquist, J. R., Comp. Biochem. Physiol. 106C:301–314 (1993)).

$GABA_A$ receptors belong to the class 1 family of neurotransmitter/hormone receptors. Other class 1 members include the glycine receptor, the serotonin type-3 receptor, the nicotinic acetylcholine receptors (muscle and neuronal types) and several excitatory amino acid receptors of vertebrates. Class 1 receptors employ no second messengers and are found where a fast conductance is required. In contrast to class 1 receptors, class 2 receptors (e.g. muscarinic, adrenergic, and others) are coupled to a second messenger and/or a G protein for their transduction, with the channel involved being separate (and usually distant) from the receptor, which is both an agonist-binding and G protein-binding molecule (Barnard, E. A., et al., TiNS 10:502–509 (1987)).

$GABA_A$ receptors are pentameric oligomers, of about 250 kilodaltons (kDa), composed of six different types of subunits, α, β, γ, δ, ε and ρ, each of approximately 50 kDa (Olsen, R. W., and Tobin, A. J., FASEB J. 4:1469–1480 (1990); Hevers, W., and Lüddens, H., Mol. Neurobiol. 18:35–86 (1998)). Each subunit comprises a large extracellular N-terminal domain that putatively includes the ligand-binding site, four hydrophobic presumed membrane-spanning domains, one or more of which contribute to the wall of the ion channel, and a small extracellular C-terminus (Lüddens, H., and Wisden, W., TiPS 12:49–51 (1991); Olsen, R. W., and Tobin, A. J., FASEB J. 4:1469–1480 (1990); Hevers, W., and Lüddens, H., Mol. Neurobiol. 18:35–86 (1998)). Heterologous expression in vitro of different combinations of GABA receptor subunit types (α, β, γ, δ etc.) and subunit isoforms (α1, α2, etc. except δ) results in heteromultimeric receptors with differing structure and pharmacology (Schofield, P. R., TiPS 10:476–478 (1989); Burt et al., FASEB J. 5:2916–2923 (1991)).

GABA receptors also play an important role in the chemical control of pests, particularly insects, such as fleas, ticks, house flies, fruit flies, plant bugs, boll weevils, grasshoppers, cockroaches, mosquitoes, beetles, locust and moths (Hainzl, D., et al., Chem. Res. Toxicol. 11:1529–1535 (1998)). To date, all insect GABA receptors studied gate a fast acting chloride ion conductance. Although they appear to share many of the properties of $GABA_A$-type receptors in the vertebrate CNS, the majority of receptors in the insect nervous system appear to be bicuculline-, pitrazepin- and RU5135-insensitive (Anthony, N. M., et al., Comp. Mol. Neurobiol., Pichon, Y., ed., Birkhäuser Verlag, Basel, Switzerland, pp. 172–209 (1993); Wafford, K. A., et al., J. Neurochem. 48:177–180 (1987)). These findings indicate that insect GABA receptors contain several drug binding sites with structural and target site specificities that are different from vertebrate receptor-binding sites (Hainzl, D., et al., Chem. Res. Toxicol. 11:1529–1535 (1998)). Selective insecticides, e.g. insecticides with favorable selective toxicity for insects relative to vertebrates, are based in part on this target-site specificity between the GABA receptors of insects and the $GABA_A$ receptors of vertebrates (Moffat, A. S., Science 261:550–551 (1993); Hainzl, D., et al., Chem. Res. Toxicol. 11:1529–1535 (1998)).

Radiolabeled ligand binding studies have considerably expanded our knowledge of insect GABA receptor pharmacology. Within the insect GABA receptor three distinct binding sites have been identified: the GABA receptor agonist binding site, a benzodiazepine binding site and a convulsant binding site (Lummis, S. C. R., Comp. Biochem. Physiol. 95C:1–8 (1990); Rauh, J. J., et al., TiPS 11:325–329 (1990)). The convulsant binding site of GABA receptors in pests is the major target site for many of the drugs and pesticides currently on the market.

Convulsant drugs and pesticides act at the GABA receptor in pest brain, ganglia and muscle as noncompetitive blockers. Inhibition of GABA receptors in pests produces neurotoxicity (e.g. convulsions, paralysis, coma and death). In the early 1980s, the pesticides lindane and cyclodienes (e.g. dieldrin) were shown to antagonize the action of GABA in stimulating chloride uptake by various pest nerve and muscle preparations (Narahashi, T., *Pharmacol. Toxicol.* 78:1–14 (1996)). GABA receptors in pests are also blocked by picrotoxin, phenylpyrazole pesticides (e.g. Fipronil®), bicyclophosphorous esters (e.g. t-butylbicyclophosphoronthionate), and bicycloorthobenzoates (4-n-propyl-4'-ethynylbicycloorthobenzoate) (U.S. Pat. No. 5,853,002). These pesticides block transmission of signals by GABA, and are very effective on a wide range of economically important pests.

Unfortunately, many potent pesticides and their derivatives also act at the $GABA_A$ receptors of animals. For example, fipronil sulfone and desulfinyl fipronil, a metabolite and photoproduct of fipronil, respectively, are not only toxic to pests, but also to upland game birds, freshwater fish and invertebrates, and waterfowl. In addition, fipronil itself is a toxicant for mammals even without oxidation to the sulfone (Hainzl, D., et al., *Chem. Res. Toxicol.* 11:1529–1535 (1998)).

Pesticides that effectively kill pests but that have little toxicity for animals and humans remain the aim of current research efforts. The present invention addresses the need for the development and use of new and more efficacious pesticides that are highly toxic to pests but not to animals susceptible to pest infestation.

SUMMARY OF THE INVENTION

A first aspect of the present invention is directed to novel compounds of Formula I.

A second aspect of the present invention is directed to pesticidal compositions comprising at least one compound of Formula I, or a salt thereof, and one or more pesticidally-acceptable excipients.

A third aspect of the present invention is directed to a method of inhibiting a pest GABA receptor, comprising contacting one or more pest GABA receptors with one or more compounds of Formula I.

A fourth aspect of the invention is directed to a method for controlling pests, comprising contacting an animal, plant or object with a composition comprising a pesticidally effective amount of at least one compound of Formula I, or a salt thereof, and one or more pesticidally-acceptable excipients.

A fifth aspect of the present invention is directed to a method for synthesizing compounds of Formula I.

A sixth aspect of the invention is directed to the use of one or more compounds of Formula I for the manufacture of collars or external devices, as well as to a treatment process relating thereto.

DETAILED DESCRIPTION OF THE PREFERRED EMBODIMENTS

A first aspect of the invention is directed to compounds of Formula I. Such compounds include compounds of Formula I:

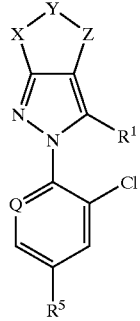

or a salt thereof, wherein $R^1$ is amino, hydrogen, alkyl, hydroxy, halo, alkoxy, alkylamino, dialkylamino, alkylthio, alkylsulfinyl, alkylsulfonyl, trifluoroalkylsulfinyl, trifluoroalkylsulfonyl, hydroxy, trifluoromethyl, acetylamino, —$OSO_2R^2$, —$OS(O)R^2$, —$OC(O)R^2$, —$OC(O)NHR^2$, or —$NHC(O)NHR^2$ where $R^2$ is $C_{1-4}$ alkyl or optionally substituted aryl;

X, Y and Z are each independently $(CH)_n$, $(CR^3R^4)_n$, S, S(O), or $SO_2$, wherein n is 1–2;

Q is N or C—$R^6$, wherein $R^6$ is fluoro, chloro, bromo, or iodo;

$R^5$ is halo, $C_1$–$C_6$alkyl, $C_1$–$C_4$ alkenyl, $C_1$–$C_4$ alkoxy, $C_1$–$C_4$ alkylamino, $C_1$–$C_4$ dialkylamino, $C_1$–$C_4$ alkylthio, $C_1$–$C_4$ alkylsulfinyl, $C_1$–$C_4$ alkylsulfonyl, $C_1$–$C_4$ trifluoroalkylsulfinyl, $C_1$–$C_4$ trifluoroalkylsulfonyl, hydroxy, amino, or trifluoromethyl;

$R^3$ and $R^4$ are each independently hydrogen, halo, alkyl, alkenyl, alkynyl, cycloalkyl, cyano, trifluoromethyl, aryl, alkylamino, dialkylamino, alkoxy, cycloalkoxy, trifluoroalkyl, pentafluoroalkyl, perfluoroalkyl, thioalkyl, cycloalkylthio, trifluoroalkylthio, alkylthio, alkylsulfinyl, alkylsulfonyl, amino, or hydroxy, or $R^3$ and $R^4$ taken together are oxo, or $R^3$ and $R^4$ taken together with the carbon to which they are attached form a 3- to 7-membered saturated ring optionally including one or two oxygen or sulfur atoms, said ring being optionally substituted by one to three $C_{1-4}$ alkyl groups;

or vicinal $R^4$ can form an optionally substituted cycloalkyl or aryl ring while $R^3$ is as defined above;

with the proviso that only one of X, Y and Z can be S, S(O) or $SO_2$.

Preferred values of Q are C—$R^6$ wherein $R^6$ is fluoro, chloro, bromo, or iodo. The most preferred value of Q is C—$R^6$ wherein $R^6$ is chloro.

Preferred values of $R^5$ are $CF_3$ and Cl. The most preferred value of $R^5$ is $CF_3$.

A second aspect of the invention is directed to pesticidal compositions comprising a pesticidally effective amount of at least one compound of Formula I, or a pesticidally-acceptable salt thereof, wherein $R^1$–$R^6$, Q, X, Y, and Z are as defined above, and one or more pesticidally-acceptable excipients.

A third aspect of the present invention is directed to a method of inhibiting a pest GABA receptor, comprising contacting one or more pest GABA receptors with one or more compounds of Formula I or a pesticidally-acceptable salt thereof, wherein $R^1$–$R^6$, Q, X, Y, and Z are as defined above.

A fourth aspect of the present invention is directed to methods for controlling pests, comprising contacting an animal, plant or object with a composition comprising a pesticidally effective amount of at least one compound of Formula I, or a pesticidally-acceptable salt thereof, wherein $R^1$–$R^6$, Q, X, Y, and Z are as defined above, and one or more pesticidally-acceptable excipients. For purposes of the present invention, pests are undesired arthropods, in particular insects and arachnids, which are harmful to plants or animals susceptible to infestation by such arthropods. The methods of the present invention are suitable for combating animal pests, preferably arthropods, in particular insects and arachnids, encountered in and on companion animals, in agriculture, in forestry, in the protection of stored products and of materials, and in the hygiene field. Compounds employed in the methods of the invention have good plant tolerance or favorable safety to warm-blooded animals.

In particular, compounds of Formula I may be applied to control arthropods in compositions suitable for internal or external administration to vertebrates, or application for the control of arthropods in any indoor or outdoor area. Such compositions comprise at least one compound of Formula I and one or more excipients. The methods are more preferably used to reduce the viability and/or reproductive capacity of any ectoparasite. Preferred ectoparasites to target include arachnids, insects and leeches. More preferred ectoparasites include fleas and ticks. For example, the invention can be employed for killing fleas of the genus Ctenocephalides, in particular *C. felis* and *C. canis*, and ticks, in particular of the genus Rhipicephalus, especially *R. sanguineus*, as well as harvest ticks (*Trombicula automnalis*), *Dermacentor variabilis, Dermacentor andersoni, Dermacentor occidentalis, Amblyomma americanum, Ixodes scapularis*, and *Ixodes pacificus*.

One subclass of compounds and pharmaceutically acceptable salts thereof include compounds of Formula II:

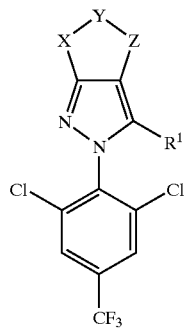

II or a salt thereof, wherein $R^1$ is amino, hydrogen, alkyl, hydroxy, halo, alkoxy, acetylamino, —OSO$_2$R$^2$, —OS(O)R$^2$, —OC(O)R$^2$, —OC(O)NHR$^2$, or —NHC(O)NHR$^2$ where R$^2$ is $C_{1-4}$ alkyl or optionally substituted aryl;

X, Y and Z are each independently (CH)$_n$, (CR$^3$R$^4$)$_n$, S, S(O), or SO$_2$, wherein n is 1–2;

$R^3$ and $R^4$ are each independently hydrogen, halo, alkyl, alkenyl, alkynyl, cycloalkyl, cyano, trifluoromethyl, aryl, alkoxy, cycloalkoxy, trifluoroalkyl, pentafluoroalkyl, perfluoroalkyl, thioalkyl, cycloalkylthio, trifluoroalkylthio, alkylthio, alkylsulfinyl, alkylsulfonyl or hydroxy, or $R^3$ and $R^4$ taken together are oxo, or $R^3$ and $R^4$ taken together with the carbon to which they are attached form a 3- to 7-membered saturated ring optionally including one or two oxygen or sulfur atoms, said ring being optionally substituted by one to three $C_{1-4}$ alkyl groups;

or vicinal $R^4$ can form an optionally substituted cycloalkyl or aryl ring while $R^3$ is as defined above;

with the proviso that only one of X, Y and Z can be S, S(O) or SO$_2$.

A second subclass of compounds and pharmaceutically acceptable salts thereof are compounds of Formula I wherein $R^3$ and $R^4$ are each independently hydrogen, halo, alkyl, cyano, trifluoromethyl, aryl, alkoxy or hydroxy, or $R^3$ and $R^4$ taken together are oxo or $R^3$ and $R^4$ taken together with the carbon to which they are attached form a 3- to 7-membered saturated ring optionally including one or two oxygen or sulfur atoms, said ring being optionally substituted by 1–3 $C_{1-4}$ alkyl groups; or vicinal $R^4$ can form an optionally substituted cycloalkyl or aryl ring.

Preferred values of $R^3$ and $R^4$ include hydrogen; $C_{1-4}$ alkyl including methyl, ethyl, n-propyl, i-propyl, butyl, t-butyl and i-butyl; fluoro; bromo; cyano; trifluoromethyl; phenyl; $C_{1-4}$ alkoxy including methoxy and ethoxy; and hydroxy. Preferred values of $R^3$ and $R^4$ when taken together include oxo, ethylenedithio and optionally substituted alkylenedioxy such as ethylenedioxy and propylenedioxy.

Preferred $R^1$ include hydrogen, $C_{6-10}$ arylsulfonyl, methyl, methoxy, hydroxy, acetylamino, amino, benzoyl, chloro and bromo. Most preferably, $R^1$ is hydrogen, amino and acetylamino.

Preferred values of X, Y and Z are such that, taken together, X, Y and Z form —CH═CH—S—, —CH$_2$SCH$_2$—, —(CH$_2$)$_2$S—, —CH$_2$S(O)CH$_2$—, —CH$_2$SO$_2$CH$_2$—, —CH$_2$CH$_2$SCH$_2$—, —CH$_2$CH$_2$S(O)CH$_2$—, —CH$_2$CH$_2$SO$_2$CH$_2$—, —(CH$_2$)$_3$—, —(CH$_2$)$_4$—, —(CH$_2$)$_5$—, —(CF$_2$)$_3$— —C(CH$_3$)$_2$CH$_2$CH$_2$—, —C(CH$_3$)$_2$CH$_2$CH$_2$CH$_2$—, —CH$_2$CF$_2$S—, —CH$_2$CF$_2$SO$_2$—, —CH$_2$CF$_2$S(O)—,

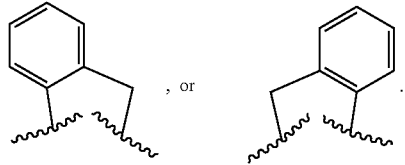

, or

Most preferred values of X, Y and Z include —CH$_2$SCH$_2$—, —CH$_2$S(O)CH$_2$—, —CH$_2$SO$_2$CH$_2$— and —(CH$_2$)$_3$—.

A third subclass of compounds and pharmaceutically acceptable salts thereof includes compounds of Formula II, or a salt thereof, wherein $R^1$ is hydrogen;

X, Y, and Z are each independently (CH)$_n$, or (CR$^3$R$^4$)$_n$, wherein n is 1–2 and $R^3$ and $R^4$ are each independently:

hydrogen; or hydroxy; or fluoro, chloro, bromo or iodo; or $C_1$–$C_6$ alkyl, $C_2$–$C_6$ alkenyl, $C_2$–$C_6$ alkynyl or $C_3$–$C_7$ cycloalkyl; or $C_1$–$C_6$ alkoxy, $C_3$–$C_7$ cycloalkyloxy, trifluoroalkyl, pentafluoroalkyl, or perfluoroalkyl; or $C_1$–$C_6$ thioalkyl, $C_3$–$C_7$ cycloalkylthio, $C_1$–$C_2$ trifluoroalkylthio or $C_1$–$C_6$ alkylthio; or $C_1$–$C_6$ sulfinyl, $C_1$–$C_6$ sulfonyl, $C_{1-2}$ trifluoroalkylsulfinyl, $C_{1-2}$ trifluoroalkylsulfonyl; or R³ and R⁴ are taken together form oxo.

In said third subclass of compounds, preferred values of R¹ include hydrogen, $C_{1-4}$ alkyl, amino, and $C_{1-4}$ alkoxy, more preferably hydrogen.

Preferred values of X, Y and Z are such that, taken together, X, Y and Z form —CH₂CH₂CR³R⁴—, —CH₂CR³R⁴CH₂—, —CR³R⁴CH₂CH₂—, —CR³R⁴CH₂CR³R⁴—, —CR³R⁴CR³R⁴CH₂—, —CH₂CR³R⁴CR³R⁴—, and —CR³R⁴CR³R⁴CR³R⁴—.

Preferred values of R³ and R⁴ are hydrogen, hydroxy, fluoro, chloro, bromo or iodo; $C_1-C_6$ alkyl, $C_2-C_6$ alkenyl, $C_2-C_6$ alkynyl, $C_3-C_7$ cycloalkyl; $C_{1-C6}$ alkoxy, $C_2$, $C_3-C_7$ cycloalkyloxy; trifluoroalkyl, pentafluoroalkyl, perfluoroalkyl; $C_1-C_6$ thioalkyl, $C_3-C_7$ cycloalkylthio, $C_1-C_2$ trifluoroalkylthio, $C_1-C_6$ alkylthio; $C_1-C_6$ sulfinyl, $C_1-C_6$ sulfonyl, $C_{1-2}$ trifluoroalkylsulfinyl, or $C_{1-2}$ trifluoroalkylsulfonyl. Preferred values of R³ and R⁴ when taken together include oxo, ethylenedithio and optionally substituted alkylenedioxy such as ethylenedioxy and propylenedioxy.

More preferred values of R³ and R⁴ are hydrogen, fluoro, chloro, methyl, ethyl, hydroxy, methoxy, trifluoromethoxy, methylthio, trifluoromethylthio, methylsulfinyl, methylsulfonyl, trifluoromethylsulfinyl, and trifluoromethylsulfonyl. More preferred values of R³ and R⁴ when taken together are oxo, ethylenedithio, ethylenedioxy, and propylenedioxy.

A fourth subclass of compounds and pharmaceutically acceptable salts thereof are compounds of Formula II wherein:

R¹ is hydrogen;

X, Y and Z are each independently $(CH)_n$ or $(CR^3R^4)_n$, wherein n is 1–2;

R³ and R⁴ are each independently hydrogen, fluoro, hydroxy, $C_1-C_6$ alkoxy, $C_1-C_6$ alkyl, $C_2-C_6$ alkenyl, $C_2-C_6$ alkynyl or $C_3-C_7$ cycloalkyl; or R³ and R⁴ are taken together form oxo.

Examples of suitable compounds include:

2-[2,6-dichloro-4-(trifluoromethyl)phenyl]-4,6-dihydrothieno[3,4-c]pyrazole-3-ylamine (1);

3-amino-2-[2,6-dichloro-4-(trifluoromethyl)phenyl]-4,6-dihydrothieno-[3,4-c]pyrazole-5-one (1');

N-{2-[2,6-dichloro-4-(trifluoromethyl)phenyl]-4,6-dihydrothieno[3,4-c]pyrazol-3-yl}acetamide (2);

N-{2-[2,6-dichloro-4-(trifluoromethyl)phenyl]-5-oxo-4,6-dihydrothieno-[3,4-c]pyrazol-3-yl}acetamide (2');

2-[2,6-dichloro-4-(trifluoromethyl)phenyl]-4,6-dihydrothieno-[3,4-c]pyrazole (3);

2-[2,6-dichloro-4-(trifluoromethyl)phenyl]-4,6-dihydrothieno-[3,4-c]pyrazole-5-one ((±), (+), (−)-3');

2-[2,6-dichloro-4-(trifluoromethyl)phenyl]-4,6-dihydrothieno-[3,4-c]pyrazole-5,5-dione (3");

2-[2,6-dichloro-4-(trifluoromethyl)phenyl]-4,6-dihydrothieno-[3,4-c]pyrazole-3-yl benzenesulfonate (6);

2-[2,6-dichloro-4-(trifluoromethyl)phenyl]-2H,4H,6H,7H-thiano[4,3-c]pyrazole (10);

2-[2,6-dichloro-4-(trifluoromethyl)phenyl]-2,4,5,6-tetrahydrocyclopenta[c]pyrazole (11);

2-[2,6-dichloro-4-(trifluoromethyl)phenyl]-6,6-dimethyl-2,4,5,6-tetrahydrocyclopenta[c]pyrazole (12);

2-[2,6-dichloro-4-(trifluoromethyl)phenyl]-4,5,6,7-tetrahydro-2H-indazole (13);

2-[2,6-dichloro-4-(trifluoromethyl)phenyl]-2,4,5,6,7,8-hexahydrocyclohepta[c]pyrazole (15);

2-[2,6-dichloro-4-(trifluoromethyl)phenyl]indeno[1,2-c]pyrazole (16);

2-[2,6-dichloro-4-(trifluoromethyl)phenyl]-2H-thieno[3,2-c]pyrazole (22);

2-[2,6-dichloro-4-(trifluoromethyl)phenyl]-2H-indazole (46);

2-[2,6-dichloro-4-(trifluoromethyl)phenyl]-3-methyl-2,4,5,6-tetrahydrocyclopenta[c]pyrazole (33);

2-[2,6-dichloro-4-(trifluoromethyl)phenyl]-3-methyl-4,5,6,7-tetrahydro-2H-indazole (34);

3,4-diaza-4-[2,6-dichloro-4-(trifluoromethyl)phenyl]tricyclo[5.2.1.0$^{2.6}$]deca-2,5-diene (35);

8-[2,6-dichloro-4-(trifluoromethyl)phenyl]-5,5,9-trimethylspiro-[1,3-dioxane]-2,5'-2,4',5,6',7'-tetrahydro-2H-indazole (36);

2-[2,6-dichloro-4-(trifluoromethyl)phenyl]-2,4,6,7-tetrahydroindazole-5-one (37);

2-[2,6-dichloro-4-(trifluoromethyl)phenyl]-5-phenyl-4,5,6,7-tetrahydro-2H-indazole (39);

2-[2,6-dichloro-4-(trifluoromethyl)phenyl]-4,6,6-trimethyl-2,4,5,6-tetrahydrocyclopenta[c]pyrazole (45);

5,6-diaza-5-[2,6-dichloro-4-(trifluoromethyl)phenyl]tetracyclo-[8.2.1.0$^{2,9}$0.0$^{3,7}$]trideca-3,6-diene (47);

2-[2,6-dichloro-4-(trifluoromethyl)phenyl]-4,4-dimethyl-2,4,5,6-tetrahydrocyclopenta[c]pyrazole (38);

2-[2,6-dichloro-4-(trifluoromethyl)phenyl]-4-phenyl-2,4,5,6-tetrahydrocyclopenta[c]pyrazole (40);

2-[2,6-dichloro-4-(trifluoromethyl)phenyl]-4-methyl-2,4,5,6-tetrahydrocyclopenta[c]pyrazole (42);

2-[2,6-dichloro-4-(trifluoromethyl)phenyl]-4-hydroxy-2,4,5,6-tetrahydrocyclopenta[c]pyrazole (62);

2-[2,6-dichloro-4-(trifluoromethyl)phenyl]-4-methoxy-2,4,5,6-tetrahydrocyclopenta[c]pyrazole (71);

2-[2,6-dichloro-4-(trifluoromethyl)phenyl]-4-trifluoromethoxy-2,4,5,6-tetrahydrocyclopenta[c]pyrazole;

2-[2,6-dichloro-4-(trifluoromethyl)phenyl]-4-methylthio-2,4,5,6-tetrahydrocyclopenta[c]pyrazole (68);

2-[2,6-dichloro-4-(trifluoromethyl)phenyl]-4-trifluoromethylthio-2,4,5,6-tetrahydrocyclopenta[c]pyrazole (65);

2-[2,6-dichloro-4-(trifluoromethyl)phenyl]-5,5-difluoro-4-hydroxy-2,4,5,6-tetrahydrocyclopenta[c]pyrazole;

2-[2,6-dichloro-4-(trifluoromethyl)phenyl]-5,5-difluoro-4-methoxy-2,4,5,6-tetrahydrocyclopenta[c]pyrazole;

2-[2,6-dichloro-4-(trifluoromethyl)phenyl]-5,5-difluoro-4-trifluoromethoxy-2,4,5,6-tetrahydrocyclopenta[c]pyrazole;

2-[2,6-dichloro-4-(trifluoromethyl)phenyl]-5,5-difluoro-4-methylthio-2,4,5,6-tetrahydrocyclopenta[c]pyrazole;

2-[2,6-dichloro-4-(trifluoromethyl)phenyl]-5,5-difluoro-4-trifluoromethylthio-2,4,5,6-trihydrocyclopenta[c]pyrazole;

2-[2,6-dichloro-4-(trifluoromethyl)phenyl]-6,6-difluoro-2,4,5,6-tetrahydrocyclopenta[c]pyrazole (50);

2-[2,6-dichloro-4-(trifluoromethyl)phenyl]-4,4-difluoro-2,4,5,6-tetrahydrocyclopenta[c]pyrazole (61);

2-[2,6-dichloro-4-(trifluoromethyl)phenyl]-5,5-difluoro-2,4,5,6-tetrahydrocyclopenta[c]pyrazole;

2-[2,6-dichloro-4-(trifluoromethyl)phenyl]-4,4,6,6-tetrafluoro-2,4,5,6-tetrahydrocyclopenta[c]pyrazole (53);

2-[2,6-dichloro-4-(trifluoromethyl)phenyl]-4,4,5-trifluoro-2,4,5,6-tetrahydrocyclopenta[c]pyrazole (56);

2-[2,6-dichloro-4-(trifluoromethyl)phenyl]-4,4,5,5-tetrafluoro-2,4,5,6-tetrahydrocyclopenta[c]pyrazole (92);

2-[2,6-dichloro-4-(trifluoromethyl)phenyl]-5,5-difluoro-4-methyl-2,4,5,6-tetrahydrocyclopenta[c]pyrazol-4-ol (93);

2-[2,6-dichloro-4-(trifluoromethyl)phenyl]-5,5-difluoro-5,6-dihydrocyclopenta[c]pyrazol-4-one (91);

2-[2,6-dichloro-4-(trifluoromethyl)phenyl]-5,5-difluoro-2,4,5,6-tetrahydrocyclopenta[c]pyrazole (90);

2-[2,6-dichloro-4-(trifluoromethyl)phenyl]-4,6-dihydrocyclopenta[c]pyrazol-5-one (85);

2-[2,6-dichloro-4-(trifluoromethyl)phenyl]-4,4,5,6-tetrafluoro-2,4,5,6-tetrahydrocyclopenta[c]pyrazole (89);

2-[2,6-dichloro-4-(trifluoromethyl)phenyl]-5,6-difluoro-4-methyl-2,4,5,6-tetrahydrocyclopenta[c]pyrazol-4-ol (88);

2-[2,6-dichloro-4-(trifluoromethyl)phenyl]-5,6-difluoro-5,6-dihydrocyclopenta[c]pyrazol-4-one (87); and 2-[2,6-dichloro-4-(trifluoromethyl)phenyl]-5,6-difluoro-2,4,5,6-tetrahydrocyclopenta[c]pyrazole (86);

DEFINITIONS

The term "optionally substituted" when not otherwise explicitly provided for refers to the replacement of a hydrogen (or in the case of keto, two hydrogens) in a particular radical, with a functional group selected from the group consisting of halogen, trifluoromethyl, hydroxy, $C_{1-4}$ alkoxy, $C_{1-4}$ alkylthio, $C_{1-4}$ alkylsulfinyl, amino, nitro, cyano, $C_{2-6}$ carboxyalkyl, amidine, tetrazolyl, mono- or di-($C_{1-6}$) alkylamino, mono- or di-($C_{6-10}$) arylamino, $C_{6-10}$ arylthio, $C_{6-10}$ arylsulfonyl, $C_{6-10}$ arylsulfinyl, keto, $C_{6-10}$ aryl hydrazone, aminocarbonyl, mono- or di-($C_{1-6}$) alkylaminocarbonyl and mono- or di-($C_{1-6}$) alkylamino-thiocarbonyl.

The term "alkyl" as employed herein by itself or as part of another group refers to both straight and branched chain radicals of up to 10 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, and decyl. Preferably, the alkyl chain is 1 to 8 carbon atoms in length, more preferably from 1 to 4 carbon atoms in length. The term "cycloalkyl" includes bicycloalkyl and other bridged ring structures.

The term "aryl" as employed herein by itself or as part of another group refers to monocyclic or bicyclic aromatic groups containing from 6 to 14 carbons in the ring portion, preferably 6–10 carbons in the ring portion, such as phenyl, naphthyl, tetrahydronaphthyl, or biphenyl.

The terms "alkoxy" refers to any of the above alkyl groups linked to an oxygen atom.

The term "halogen" or "halo" as employed herein by itself or as part of another group refers to chlorine, bromine, fluorine or iodine with chlorine or fluorine being preferred.

The term "vicinal" is used herein to refer to substituents on adjacent carbon atoms. For example, reference to "vicinal $R^4$" denotes both $R^4$ substituents in a —$CR^3R^4$—$CR^3R^4$— group.

By the term "pesticidally-acceptable salts" is meant salts the cations of which are known and accepted in the art for the formation of salts of pesticidally active acids for agricultural or horticultural use. When intended for application to vertebrates to combat infection or infestation by arthropods, the salts with bases used will be non-toxic to vertebrates. By the term "non-toxic" is meant salts with bases the cations of which are innocuous to the vertebrates at the doses administered and which do not vitiate the beneficial effects produced by the anion.

Preferably, the salts are water-soluble. Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts. Where reference is made in the present specification to the compounds of Formula I such reference is intended to include also the salts with pesticidally-acceptable bases of compounds of Formula I where appropriate.

As used herein, the term "excipient" refers to the additives used to convert pesticidally-active compounds into forms suitable for their intended purpose. For pesticidal compositions of the present invention suitable for administration to an animal, the term "excipient" is meant to include, but not be limited by, those excipients described in the *Handbook of Pharmaceutical Excipients*, American Pharmaceutical Association, $2^{nd}$ Edition (1994), which is herein incorporated by reference in its entirety. The term "excipients" is meant to include diluents, carriers, fillers, binders, disintegrating agents, lubricants, coatings, solvents, suspending agents, dyes, extenders, surfactants, auxiliaries and the like as understood by those of skill in the art.

The term "pesticidally-acceptable excipient" is meant to include excipients which are known and accepted in the art for the formation of pesticides for agricultural or horticultural use. When intended for application to vertebrates to combat infection or infestation by arthropods, the excipients used will be non-toxic to vertebrates. The term "non-toxic" is meant to refer to excipients which are innocuous to the vertebrates at the concentrations administered and which do not vitiate the beneficial effects produced by the active pesticide.

COMPOSITIONS AND METHODS OF USE

The compounds of Formula I can be employed as pesticides. For purposes of the present invention, pests are undesired arthropods, for example insects or arachnids, which are harmful to plants or animals susceptible to infestation by such arthropods.

Compounds of the invention are suitable for controlling animal pests, preferably arthropods, in particular insects and arachnids, encountered in and on companion animals, in agriculture, in forestry, in the protection of stored products and of materials, and in the hygiene field, and have good plant tolerance or favorable safety to warm-blooded animals.

Compounds of the invention while active against plant, hygiene and stored product pests, are particularly useful in the veterinary medicine sector, against animal ectoparasites such as scaly ticks, argasidae, scab mites, trombidae, flies (stinging and sucking), parasitic fly larvae, lice, hair lice, bird lice and fleas. For example, the compounds have activity against fleas, such as fleas of the genus Ctenocephalides, in particular *C. felis* and *C. canis*, and ticks, such as ticks of the genus Rhipicephalus, especially *R. sanguineus*, as well as harvest ticks (*Trombicula automnalis*), *Dermacentor variabilis, Dermacentor andersoni, Dermacentor occidentalis, Amblyomma americanum, Ixodes scapularis*, and *Ixodes pacificus*. By virtue of their activity against fleas and ticks, compounds of the invention are suitable for treating companion animals, such as dogs and cats.

Compounds of the invention are also suitable for the controlling of arthropods which infest useful animals in agriculture such as, cattle, sheep, goats, horses, pigs, donkeys, camels, buffalo, rabbits, hens, turkeys, ducks, geese, bees, other domestic animals such as, dogs, cats, cage birds, aquarium fish and so-called experimental animals such as, hamsters, rabbits, guinea pigs, rats and mice. The aim of combating these arthropods is to reduce fatalities and reductions in yield (in meat, milk, wool, skins, eggs, honey, etc.) so that the use of a compound according to the invention renders the keeping of animals more economic and more simple.

Compositions and methods of the present invention can be used to reduce the viability and/or reproductive capacity of any ectoparasite. Preferred ectoparasites to target include arachnids, insects and leeches. More preferred ectoparasites include fleas; ticks, including both hard ticks of the family Ixodidae (e.g., Ixodes and Amblyomma) and soft ticks of the family Argasidae (e.g., Ornithodoros, such as *O. parkeri* and *O. turicata*); flies, such as midges (e.g., Culicoides), mosquitos, houseflies, sand flies, black flies, horse flies, horn flies, deer flies, tsetse flies, stable flies, myiasis-causing flies and biting gnats; ants; spiders; lice; mites; and true bugs, such as bed bugs and kissing bugs, including those carrying Chagas disease. Even more preferred ectoparasites include fleas, mosquitos, midges, houseflies, sandflies, blackflies, ticks and kissing bugs, with fleas, ticks, mosquitos, houseflies and midges being even more preferred.

Particularly preferred compositions and methods of the present invention targets fleas. Preferred fleas include Ctenocephalides, Xenopsylla, Pulex, Tunga, Nosopsyllus, Diamanus, Ctopsyllus and Echidnophaga fleas, with *Ctenocephalides canis* and *Ctenocephalides felis* fleas being even more preferred. For the purposes of illustration, many of the following embodiments discuss efficacy against fleas. Such discussion of efficacy against fleas is not intended, in any way, to limit the scope of the present invention.

A preferred aspect of the invention is directed towards killing fleas of the genus Ctenocephalides, in particular *C. felis* and *C. canis*, and ticks, in particular of the genus Rhipicephalus, especially *R. sanguineus*, as well as harvest ticks (*Trombicula automnalis*), *Dermacentor variabilis*, *Dermacentor andersoni*, *Dermacentor occidentalis*, *Amblyomma americanum*, *Ixodes scapularis*, and *Ixodes pacificus*.

A further aspect of the present invention is the use of a compound of Formula I for the production of a collar or other external device intended to be attached or attachable to an animal, in particular cats and dogs.

This aspect of the invention is directed mainly towards fleas of the genus Ctenocephalides, in particular *C. felis* and *C. canis*, and ticks, in particular of the genus Rhipicephalus, especially *R. sanguineus*, as well as harvest ticks (*Trombicula automnalis*), *Dermacentor variabilis*, *Dermacentor andersoni*, *Dermacentor occidentalis*, *Amblyomma americanum*, *Ixodes scapularis*, and *Ixodes pacificus*.

Collars intended to eliminate common ectoparasites from cats and dogs consist of a matrix, usually a plastic matrix, which incorporates a compound of Formula I, preferably between 5 and 40% active substance, and is capable of releasing the compound over time.

Slow release compositions that can be in the form of a collar or earrings for controlling harmful insects are also contemplated. Such formulations comprise from about 0.5 to about 25% active material, from about 75 to about 99.5% of a suitable resin, such as polyvinyl chloride and a catalytic amount of a plasticizer, such as dioctyl phthalate.

A subject of the present invention is thus a collar or other external device for a pet, in particular a cat or dog, made of a matrix in which is incorporated from about 0.1 to about 40% by weight, relative to the collar, of a substance which is active against ectoparasites such as fleas and ticks (antiflea and anti-tick collar or other external device), this active substance being formed of at least one compound corresponding to Formula I.

One aspect of this method is non-therapeutic and in particular relates to the cleaning of animal hairs and skin by elimination of the parasites which are present, as well as their residues and secretions. The treated animals thus have hair which is more pleasant to look at and to feel.

The invention also relates to such a method for therapeutic purposes, intended to treat and prevent parasitoses having pathogenic consequences.

Compounds of Formula I may be applied to control arthropods in compositions suitable for internal or external administration to vertebrates or application for the control of arthropods in any indoor or outdoor area. Such compositions comprise at least one compound of Formula I and one or more excipients. Such compositions can be prepared in any manner known in the art.

Suitable means of applying compounds of Formula I include:

to persons or animals infested by or exposed to infestation by arthropods by parenteral, oral or-topical application. Examples include incorporation of an active compound in feed or suitable orally-ingestible pharmaceutical formulations, edible baits, salt licks, dietary supplements, pour-on and spot-on formulations, sprays, baths, dips, showers, jets, dusts, greases, shampoos, creams, wax-smears and livestock self-treatment systems; to the environment in general or to specific locations where pests may lurk, including stored products, timber, household goods, and domestic and industrial premises, as sprays, fogs, dusts, smokes, wax-smears, lacquers, granules and baits, and in tricklefeeds to waterways, wells, reservoirs and other running or standing water; to domestic animals in feed to control fly larvae feeding in their feces;

to growing crops as foliar sprays, dusts, granules, fogs and foams; also as suspensions of finely divided and encapsulated compounds of Formula I;

as soil and root treatments by liquid drenches, dusts, granules, smokes and foams; and as seed dressings by liquid slurries and dusts.

Compositions suitable for administration to vertebrates include preparations suitable for oral, parenteral, percutaneous, e.g. pour-on, spot-on or other topical administration.

Compositions for oral administration comprise one or more of the compounds of Formula I in association with non-toxic veterinary carriers or coatings and include, for example, chewable treats, tablets, pills, capsules, pastes, gels, drenches, medicated feeds, medicated drinking water, medicated dietary supplements, slow-release boluses or other slow-release devices intended to be retained within the gastro-intestinal tract. Any of these may incorporate active ingredient contained within microcapsules or coated with acid-labile or alkali-labile or other pharmaceutically acceptable enteric coatings. Feed premixes and concentrates containing compounds of the present invention for use in preparation of medicated diets, drinking water or other materials for consumption by animals may also be used.

Compositions for parenteral administration include solutions, emulsions or suspensions in any suitable veterinary vehicle and solid or semisolid subcutaneous implants or pellets designed to release active ingredient over a protracted period and may be prepared and made sterile in any appropriate manner known to the art.

Compositions for percutaneous and topical administration include sprays, dusts, baths, dips, showers,jets, greases, shampoos, creams, wax-smears, or spot-on or pour-on preparations. Compounds of Formula I can also be administered with the aid of shaped articles which contain active compound, such as neck bands, ear tags, tail tags, limb bands, halters, marking devices and the like devices (e.g. ear tags) attached externally to animals in such a way as to provide local or systemic arthropod control.

Solid or liquid baits suitable for controlling arthropods comprise one or more compounds of Formula I and a carrier or diluent which may include a food substance or some other substance to induce consumption by the arthropod.

Medicated feeds which comprise a compound of Formula I and arthropodicidally-acceptable salts thereof and an edible carrier or diluent form an additional feature of the present invention.

Liquid compositions include water miscible concentrates, emulsifiable concentrates, flowable suspensions, wettable or soluble powders containing one or more compounds of Formula I which may be used to treat substrates or sites infested or liable to infestation by arthropods including premises, outdoor or indoor storage or processing areas, containers or equipment and standing or running water.

Solid homogenous or heterogenous compositions containing one or more compounds of Formula I, for example granules, pellets, briquettes or capsules, may be used to treat standing or running water over a period of time. A similar effect may be achieved using trickle or intermittent feeds of water dispersible concentrates.

Compositions in the form of aerosols and aqueous or non-aqueous solutions or dispersions suitable for spraying, fogging and low- or ultra-low volume spraying may also be used.

The compositions of the invention, besides at least one compound of Formula I and, if appropriate, besides extenders and auxiliaries, may also comprise at least one surfactant (wetting, dispersing and emulsifying agents).

The wetting, dispersing and emulsifying agents which may be present, particularly in wettable powders, may be of the ionic or non-ionic types, for example sulphoricinoleates, quaternary ammonium derivatives or products based upon condensates of ethylene oxide with nonyl- and octylphenol, or carboxylic acid esters of anhydrosorbitols which have been rendered soluble by etherification of the free hydroxy groups by condensation with ethylene oxide, or mixtures of these types of agents. Wettable powders may be treated with water immediately before use to give suspensions ready for application.

Liquid compositions for the application of the compounds of Formula I may take the form of solutions, suspensions and emulsions of the compounds of Formula I optionally encapsulated in natural or synthetic polymers, and may, if desired, incorporate wetting, dispersing or emulsifying agents. These emulsions, suspensions and solutions may be prepared using aqueous, organic or aqueous-organic diluents, for example acetophenone, isophorone, toluene, xylene, mineral, animal or vegetable oils, and water soluble polymers (and mixtures of these diluents), which may contain wetting, dispersing or emulsifying agents of the ionic or non-ionic types or mixtures thereof, for example those of the types described above. When desired, the emulsions containing the compounds of Formula I may be used in the form of self-emulsifying concentrates containing the active substance dissolved in the emulsifying agents or in solvents containing emulsifying agents compatible with the active substance, the simple addition of water to such concentrates producing compositions ready for use.

Compositions containing compounds of Formula I which may be applied to control arthropod pests, may also contain synergists (e.g. piperonyl butoxide or sesamex), stabilizing substances, other insecticides or other pesticides, acaricides, plant nematocides, anthelmintics or anticoccidials, fungicides (agricultural or veterinary as appropriate, e.g. benomyl, iprodione), bactericide, antivirals, arthropod or vertebrate attractants or repellents or pheromones, reodorants, flavoring agents, dyes and auxiliary therapeutic agents, e.g. trace elements or vitamins. These may be designed to improve potency, persistence, safety, uptake where desired, spectrum of pests controlled or to enable the composition to perform other useful functions in the same animal or area treated.

Examples of other pesticidally-active compounds which may be included in, or used in conjunction with, the compositions of the present invention are: chlorpyrifos, demeton-S-methyl, disulfoton, ethoprofos, fenitrothion, malathion, parathion, triazophos, amitraz, cypermethrin, deltamethrin, fenpropathrin, fenvalerate, permethrin, aldicarb, carbosulfan, pirimicarb, bendiocarb, teflubenzuron, dicofol, endosulfan, lindane, benzoximate, avermectins, ivermectin, milbemycins, thiophanate, trichlorfon, dichlorvos, diaveridine and dimetridazole.

A "pesticidally effective amount" refers to an amount of compound that will be toxic to one or more pests under the conditions administered. When administered to vertebrates parenterally, orally or by percutaneous or other means, the dosage of compounds of Formula I will depend upon the species, age and health of the vertebrate and upon the nature and degree of the vertebrate's actual or potential infestation by arthropod pest. Determination of optimal ranges of effective amounts of each component in a composition is within the skill of the art. A single dose of 0.1 to 100 mg, preferably 2.0 to 20.0 mg, per kg body weight of the animal per month or doses of 0.01 to 20.0 mg, preferably 0.1 to 5.0 mg, per kg body weight of the animal per day for sustained medication are generally suitable by oral, topical or parenteral administration. By use of sustained release formulations or devices, the daily doses required over a period of months may be combined and administered to animals on a single occasion.

Compounds are screened for GABA receptor inhibiting activity using in vitro assays that measure the ability of a test compound to bind to pest and/or mammal GABA receptors. These assays, exemplified herein in working Examples 62 and 63, employ membranes possessing active GABA receptors. Preferred compounds have selectivity towards arthropod GABA receptor versus mammalian GABA receptor. Immediately following is a description of methods for forming such membranes. Ectoparacitidal activity can be determined in vivo. Suitable tests are described in working Examples 64 and 65.

Preparation of Housefly Membranes Possessing Active GABA Receptors

Newly emerged houseflies (*Musca domestica*, available from Rincon-Vitova Insectaries, Inc., Ventura, Calif.) were sedated with carbon dioxide gas, collected in 50 mL polypropylene conical tubes, and immediately frozen by submersion in liquid nitrogen. Unless specified, all of the following work was performed at 0–4° C. After removal from liquid nitrogen, the tubes of frozen houseflies were shaken vigorously by hand to decapitate the houseflies. The decapitated houseflies were then passed through a #10 mesh tissue sieve to separate the heads, which went through the sieve, from the larger abdomen, thoraxes, and residual intact houseflies that did not pass through the sieve. Contaminating wings were removed by holding a vacuum nozzle approximately 4 cm above the heads, and contaminating legs were separated from the heads by passage through a #15 mesh screen. All remaining debris were removed from the pool of heads using forceps. The purified heads were collected in 50 mL polypropylene conical tubes and stored in liquid nitrogen until processed further.

About 13 g of purified housefly heads were suspended in about 65 mL of 10% sucrose buffer (10% sucrose (w/w) in 10 mM Tris, pH 7.5). The heads were homogenized for about 1 minute, using a Tissumizer™ homogenizer equipped with a SDT-100EN probe (available from Tekmar-Dohrmann, Cincinnati, Ohio) running at 70% of its maximum speed. The extract was further homogenized by about 5 passes through a 40 mL Dounce tissue grinder. The extract was then centrifuged at about 500×g for about 5 minutes to pellet large debris. The supernatant was collected; the pellet was washed with an additional 65 mL of 10% sucrose buffer and centrifuged at 500×g for about 5 minutes. The second supernatant was collected and combined with the first supernatant, and the pool was filtered through a 100μ CellMicroSieve™ mesh to remove residual debris (available from BioDesign of New York, Carmel, N.Y.).

Neuronal membranes containing active GABA receptors were collected via sucrose density centrifugation by the following method. About 8 mL of 35% sucrose buffer (35% sucrose (w/w) in 10 mM Tris, pH 7.5), were dispensed into each of six 38 mL ultracentrifuge tubes. These layers were overlaid with about 8 mL of 20% sucrose buffer (20% sucrose (w/w) in 10 mM Tris, pH 7.5), and finally overlaid with about 20 mL of filtered extract supernatant. The tubes were centrifuged at about 120,000×g for about 100 min at 4° C. After centrifugation, the 10% sucrose layer and most of the 20% sucrose layer were removed by aspiration. The membranes at the interface of the 20% sucrose and 35% sucrose layers were collected, pooled, diluted with 10% sucrose buffer, and centrifuged at about 120,000×g for about 40 min at 4° C. After centrifugation, the supernatant was discarded, and the pellets resuspended in about 6.5 mL of assay buffer (10 mM phosphate, 300 mM NaCl, pH 7.5) using a 10 mL Potter-Elvehjem tissue grinder with a Teflon® pestle. Protein concentration was determined by the Bio-Rad Protein Assay (available from Bio-Rad Laboratories, Hercules, Calif.) using bovine serum albumin as a standard. The membranes were aliquoted and stored in liquid nitrogen for up to 2 months before use.

Preparation of Mouse Brain Membranes Possessing Active GABA Receptors

Mouse brains were obtained from carbon dioxide-asphyxiated Swiss-Webster mice, washed with phosphate-buffered saline, and used either fresh or after storage at −80° C. for up to 10 months. Unless specified, all preparation steps were performed at 0–4° C. For each preparation, 20 brains were suspended in about 40 mL of 0.32 M sucrose and homogenized for about 2 minutes, using a Tissumizer™ homogenizer equipped with a SDT-100EN probe (available from Tekmar-Dohrmann, Cincinnati, Ohio) running at 50% of its maximum speed. The extract was centrifuged for about 5 min at about 1000×g to pellet intact brain tissue. The supernatant was retained and the pellet washed with an additional 40 mL of 0.32 M sucrose and centrifuged at 1000×g for about 5 minutes. The 1000×g supernatants were combined and centrifuged at about 10,000×g for about 20 min to pellet membranes. The 10,000×g supernatant was discarded and the pellet was resuspended in about 20 mL of water containing 1 mM EDTA. The sample was dialyzed two times for about 3 hours each against about 3 L of water. The sample was then centrifuged at about 25,000×g for about 30 min to pellet the membranes. After centrifugation, the supernatant was discarded and the wet pellet recovered. The protein concentration of the pellet was determined by the Bio-Rad Protein Assay (available from Bio-Rad Laboratories, Hercules, Calif.) using bovine serum albumin as a standard. The membranes were aliquoted and stored at −80° C. for up to 6 months before use.

Preparation of Compounds

The present invention is also directed to the multi-step synthesis of compounds of Formula I, including intermediates and intermediate reaction steps as herein described.

Compounds of the present invention can be synthesized according to methods outlined in the following scheme descriptions.

Scheme 1: 2,6-Dichloro-4-trifluoromethylphenylhydrazine was condensed with 3-cyanotetrahydrothiophen-4-one under acidic conditions to obtain aminopyrazole I which was then oxidized with m-CPBA to obtain the corresponding sulfoxide II and sulfone III. Deamination of I gave pyrazole IV, whereas acetylation of I gave the acetamide V. Sulfoxide IV' and sulfone IV" were obtained by oxidation of IV with m-CPBA. Likewise, sulfoxide V' and sulfone V" were obtained by oxidation of V with m-CPBA.

Scheme 2: 2,6-Dichloro-4-trifluoromethylphenylhydrazine was condensed with 3-carbomethoxytetrahydrothiophen-4-one to obtain the corresponding hydrazone IX which was cyclized under basic conditions to obtain the corresponding pyrazolone X. Pyrazolone X was also converted to the corresponding chloride XIa, phenyl sulfonate XIb, methyl ether XIc, and benzoate XId under standard conditions. Pyrazolone X and pyrazoles XIa–d were converted to the corresponding sulfoxides (n=1) and sulfones (n=2) by oxidation with m-CPBA.

Scheme 3: Cycloalkanones XII (n=0, 1 or 2) were treated with LDA and TMSCl to obtain the corresponding silylenol ethers XIII which were subsequently treated with TMSI and trimethylorthoformate to obtain the corresponding ketoacetals XIV. The ketoacetals XIV were condensed with 2,6-dichloro-4-trifluoromethylphenylhydrazine under acidic conditions to obtain the corresponding cycloalkapyrazoles XV.

Scheme 4: 2-Nitroaldehydes XVI were condensed with 2,6-dichloro-4-trifluoromethylaniline to obtain the corresponding imines XVII which were treated with (EtO)$_3$P to arrive at the corresponding pyrazoles XVIII.

Scheme 5: Reaction of organometallic reagents with optionally substituted cyclopentenone XIX followed by enolate trapping with TMSCl/HMPA afforded the corresponding silyl enol ethers XX which were converted to the corresponding ketoacetals XXI by treatment with TMSI and trimethylorthoformate. The ketoacetals XXI were subsequently condensed with 2,6-dichloro-4-trifluoromethylphenylhydrazine to obtain the corresponding pyrazoles XXII.

Scheme 6: Optionally-substituted cycloalkanones XXIII were treated with BF$_3$OEt$_2$ and triethyl- or trimethylorthoformate to obtain the corresponding ketoacetals XXIV which were condensed with 2,6-dichloro-4-trifluoromethylphenylhydrazine to obtain the corresponding optionally-substituted pyrazoles XXV.

Scheme 7: The halocarboxylic acids XXVII, obtained from dihalocycloalkenes XXVI by treatment with alkyl lithium and CO$_2$, were converted first to acyl halides, and then converted to the corresponding amides XXVIII under standard conditions. Dehydration of the amides XXVIII gave the corresponding nitriles XXIX which were condensed with 2,6-dichloro-4-trifluoromethylphenylhydrazine to obtain the corresponding amino pyrazoles XXX. Deamination of the aminopyrazoles XXX gave corresponding pyrazoles XXXI.

Scheme 8: The carboxylic acids XXXII were converted to the corresponding acid chlorides XXXIII and then reacted with the Wittig reagent. Pyrolysis gave the corresponding acrylonitriles XXXV which were condensed with 2,6-dichloro-4-trifluoromethylphenylhydrazine to obtain the corresponding pyrazoles XXXVI. The side chain halogen was then displaced by a protected thiol, e.g., tritylthiol, and the 4 position of the resulting pyrazole XXXVII was brominated under free radical conditions. Deprotection of thiol XXXVIII followed by cyclization gave the corresponding tetrahydrothienopyrazoles XL. Deamination gave the corresponding pyrazoles XLI and oxidation with m-CPBA gave the corresponding sulfoxides XLII and sulfones XLIII.

Scheme 9: Pyrazole 11 was oxidized to pyrazolone 48 and 49. The ratio of 48 to 49 formed from the reaction was dependent upon the oxidizing conditions used. Pyrazolone 48 was treated with ethanedithiol to form pyrazole 62. Pyrazole 62 was converted to difluoropyrazole 63 by treatment with N-iodosuccinimide (NIS) and pyridinium poly (hydrogen fluoride) (PPHF). Likewise, pyrazolone 48 was converted, under basic conditions, to the silyl enol ether, which was then reacted with 1-chloromethyl-4-fluoro-1,4-diazoniabicyclo[2.2.2]octanebis(tetrafluoroborate) (SELECTFLUOR) to provide fluoropyrazolone 54. Fluoropyrazolone 54 was reacted with ethanedithiol to yield fluoropyrazole 55, which was then treated with NIS and PPHF to produce trifluoropyrazole 56. Alternatively, Grignard reaction of 54 provided monofluorohydroxypyrazole 57. Pyrazolone 48 was also used to produce pyrazole 60, which was converted to difluoropyrazole 61. Pyrazolone 49 was fluorinated with diethylaminesulfur trifluoride (DAST) to produce difluoropyrazole 50. Difluoropyrazole 50 was oxidized to difluoropyrazolone 51, which was converted to difluoropyrazole 52, followed by fluorination to yield tetrafluoropyrazole 53. Additionally, pyrazolone 49 was lithiated, treated with TMSCl to form the silyl enol ether, and reacted with SELECTFLUOR to form fluoropyrazolone 58. Fluoropyrazolone 58 was converted to fluoropyrazole 59.

Scheme 10: Reduction of pyrazolone 48 yielded hydroxypyrazole 62, which was reacted with thionyl chloride to produce pyrazole 63 and chloropyrazole 64. Treatment of 64 with trifluoromethylthiocuprate provided trifluoromethylthiopyrazole 65, which was subsequently oxidized to produce sulfoxide 66 and sulfone 67. Additionally, chloropyrazole 64 was treated with methylthiocuprate to yield methylmercaptopyrazole 68, which was subsequently oxidized to produce sulfoxide 69 and sulfone 70.

Scheme 11: Difluoropyrazolone 51 was reduced to yield difluorohydroxypyrazole 75, which was methylated under basic conditions to provide difluoromethoxypyrazole 76. Additionally, difluoropyrazolone 51 was reacted with a Grignard reagent to produce difluorohydroxypyrazole 77, which was treated with DAST, yielding trifluoropyrazole 78.

Scheme 12 Pyrazole 79 was oxidized under standard conditions to yield dihydroxypyrazole 80, which was fluorinated with DAST to provide difluoropyrazole 81. Additionally, pyrazole 79 was treated with mCPBA to provide oxirane 82. Fluorination of 82 with PPHF provided fluorohydroxypyrazole 83.

Scheme 13: Alcohol 64 in benzene was heated at reflux with p-Toluenesulfonic acid (pTSA) for 6 hr to obtain 1:1 mixture of cyclopentens 65 and 83. This mixture was then converted to diols 84 and 85 by treating with OsO$_4$ and N-methylmorpholine-N-oxide (NMO). The two diols were then separated and 84 was converted to difluo compound 86 by treating it with DAST. Compound 86 was then oxidized to ketone 87 with CrO$_3$ and the resulting ketone was reacted with Grignard reagents to obtain tertiary alcohols 88. Compound 85 was converted to ketone 90 by heating with pTSA. The ketone 90 was reacted with ethanedithiol to obtain the corresponding thiolane which was converted to gem difluoro compound 91. Oxidation of 91 with CrO$_3$ gave ketone 92 which was converted to tetrafluoro compound 94 via dithiolane. Reaction of ketone 94 with Grignard reagents gave alcohols 93.

The included examples are illustrative, but not limiting, of the compounds, methods and compositions of the present invention. Other suitable modifications and adaptations of the variety of conditions and parameters normally encountered and obvious to those skilled in the art are within the spirit and scope of the invention.

Compounds of the present invention are shown in Table I and Schemes 1–13. In Schemes 9–11, Ar is equivalent to 2,6-dichloro-4-trifluoromethylphenyl radical. Compounds having other aromatic groups in the 1-position can be synthesized by substituting other known hydrazines for 2,6-dichloro-4-trifluoromethylphenyl hydrazine in the following schemes.

Scheme 1
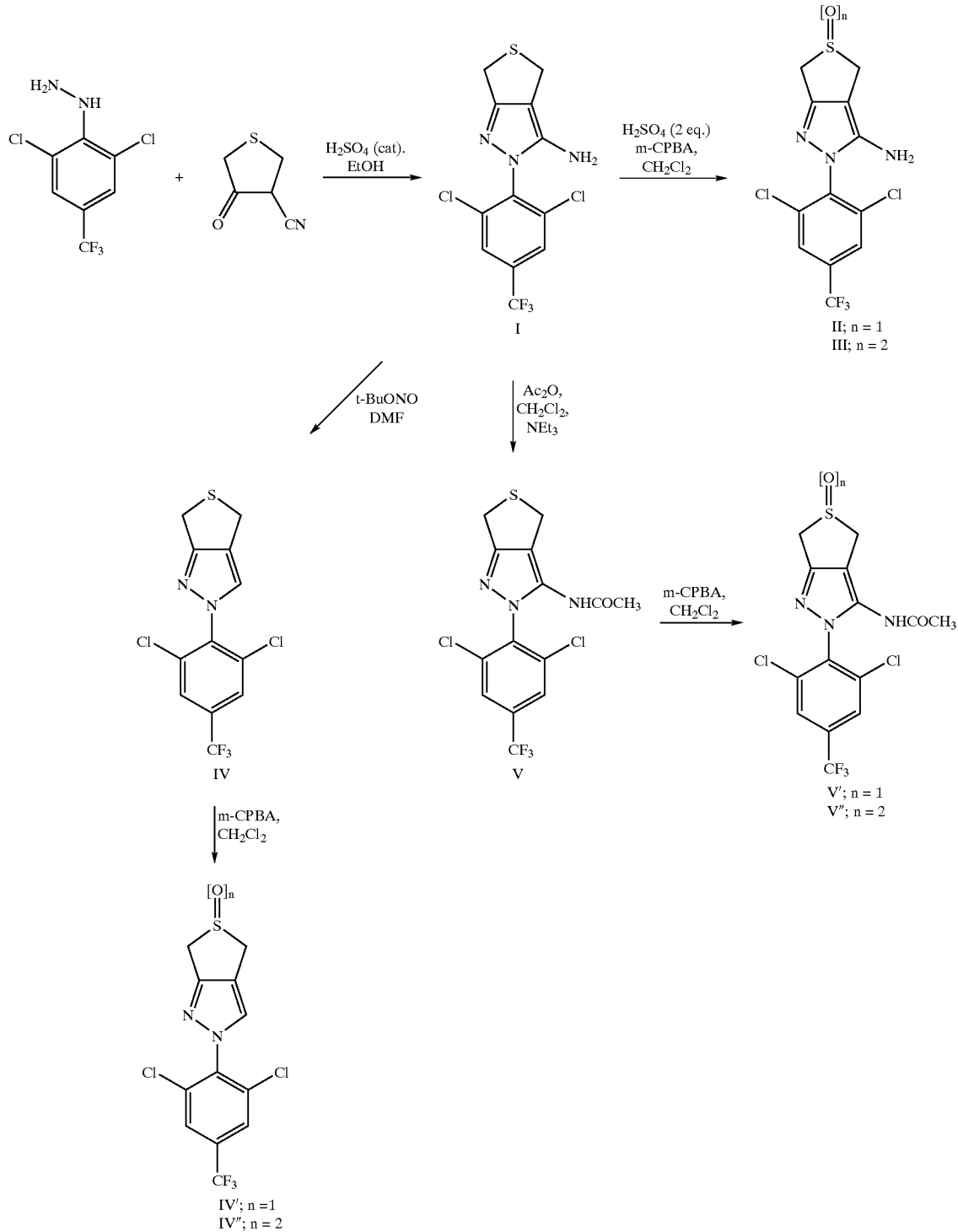

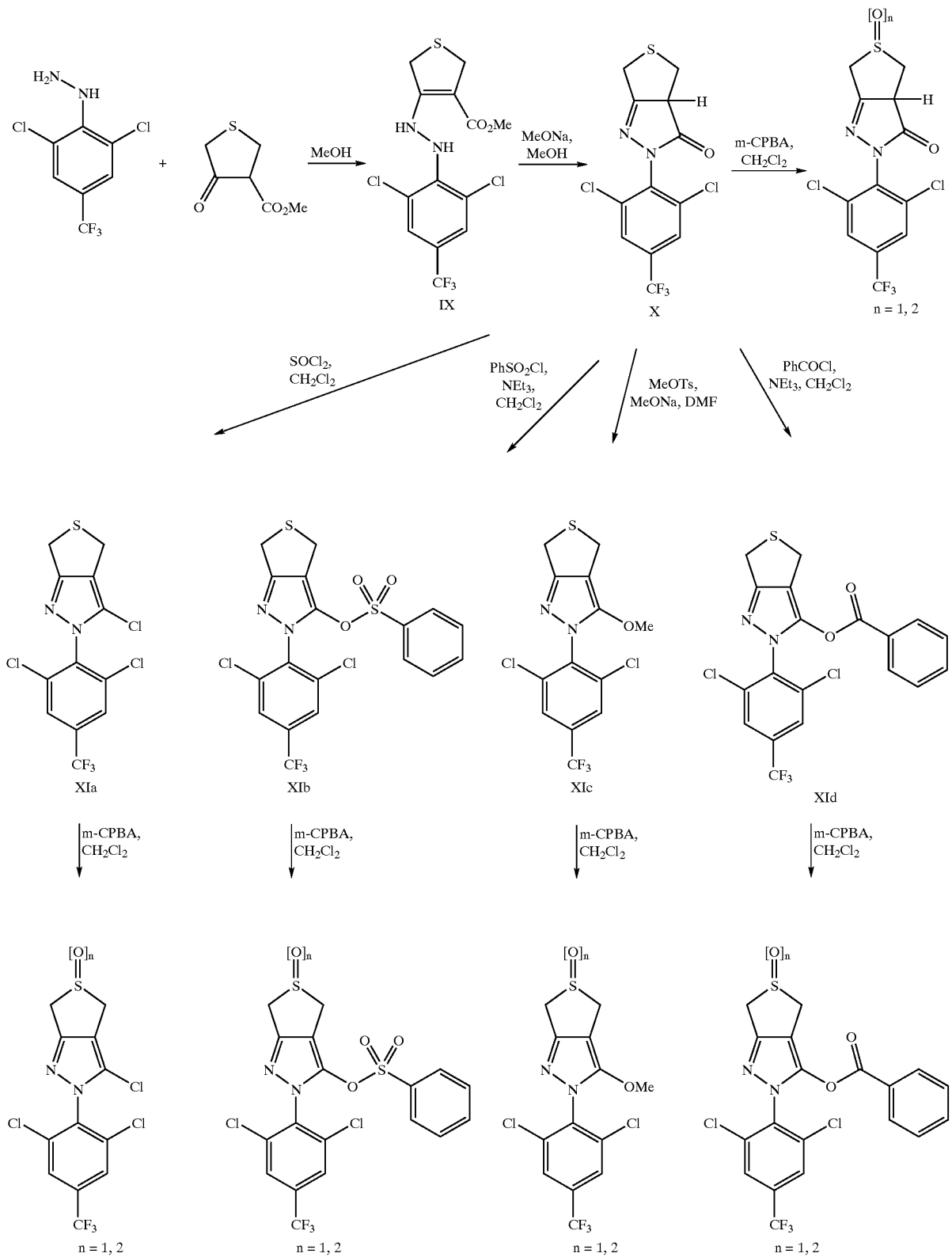

Scheme 3
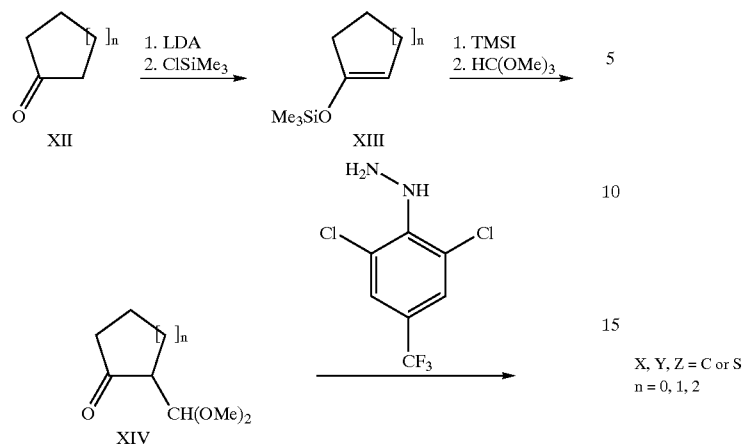
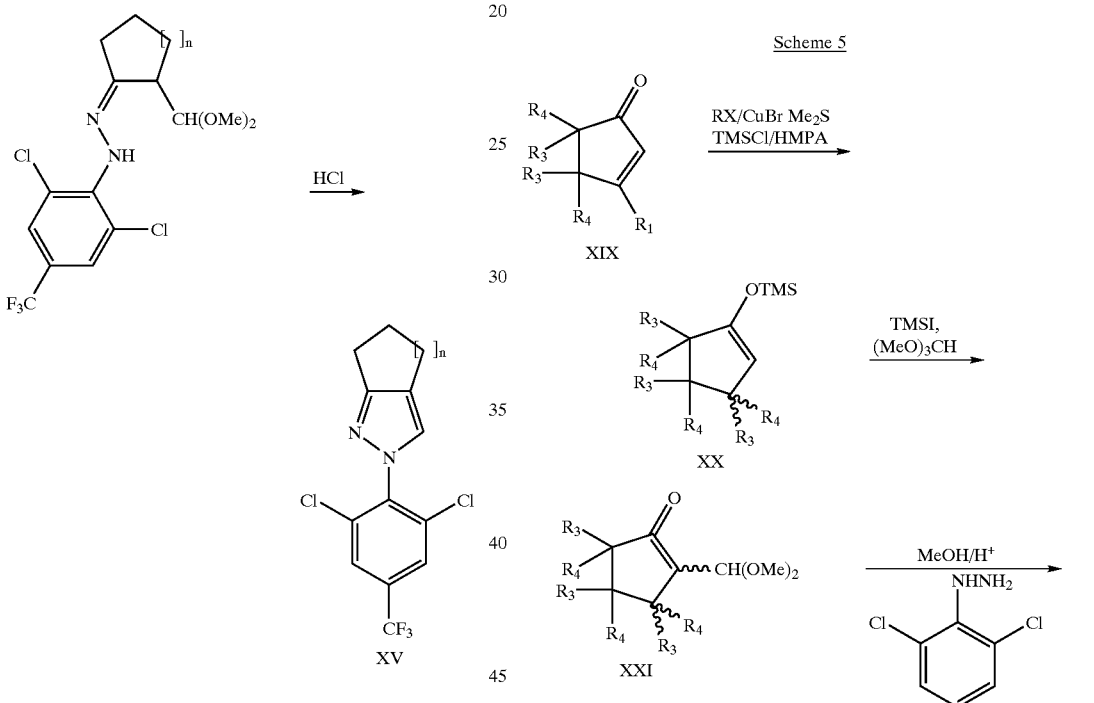
X, Y, Z = C or S
n = 0, 1, 2
Scheme 4
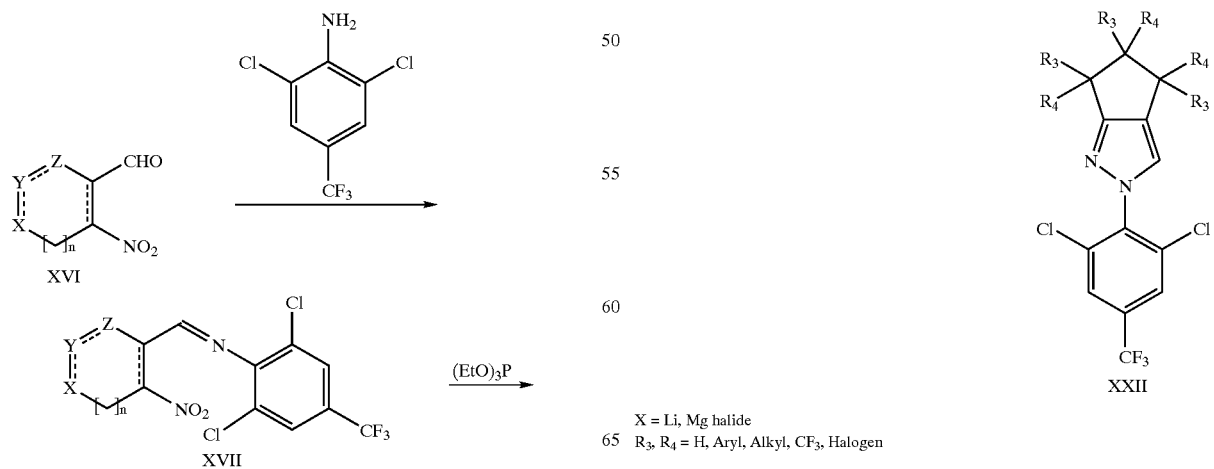
X = Li, Mg halide
R$_3$, R$_4$ = H, Aryl, Alkyl, CF$_3$, Halogen Scheme 6
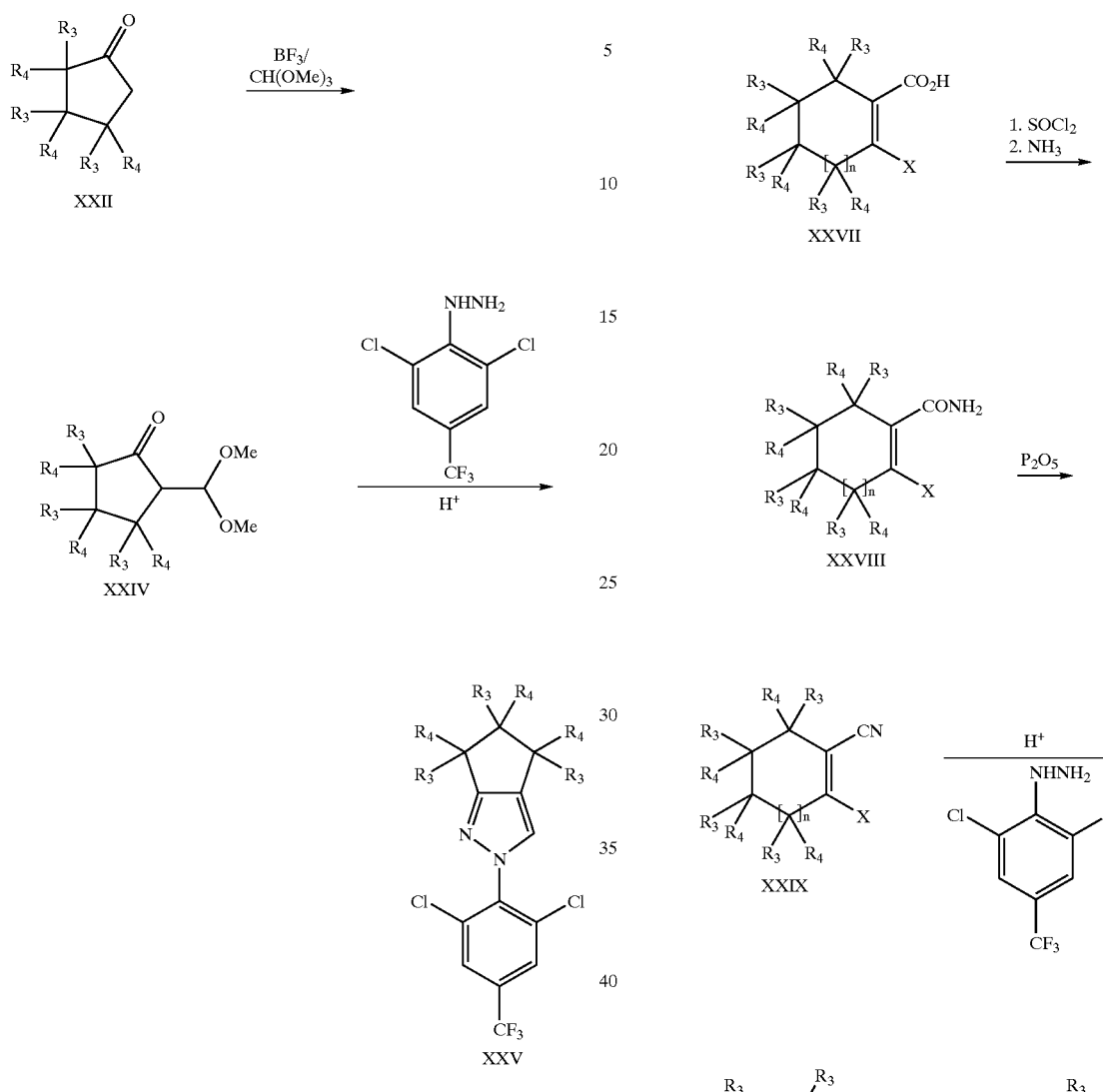
$R_3$, $R_4$ = H, alkyl, $CF_3$, halogen
Scheme 7
XXVI
X = Cl, Br, I
$R_3$, $R_4$ = H, aryl, alkyl, $CF_3$, halogen
n = 0, 1, 2

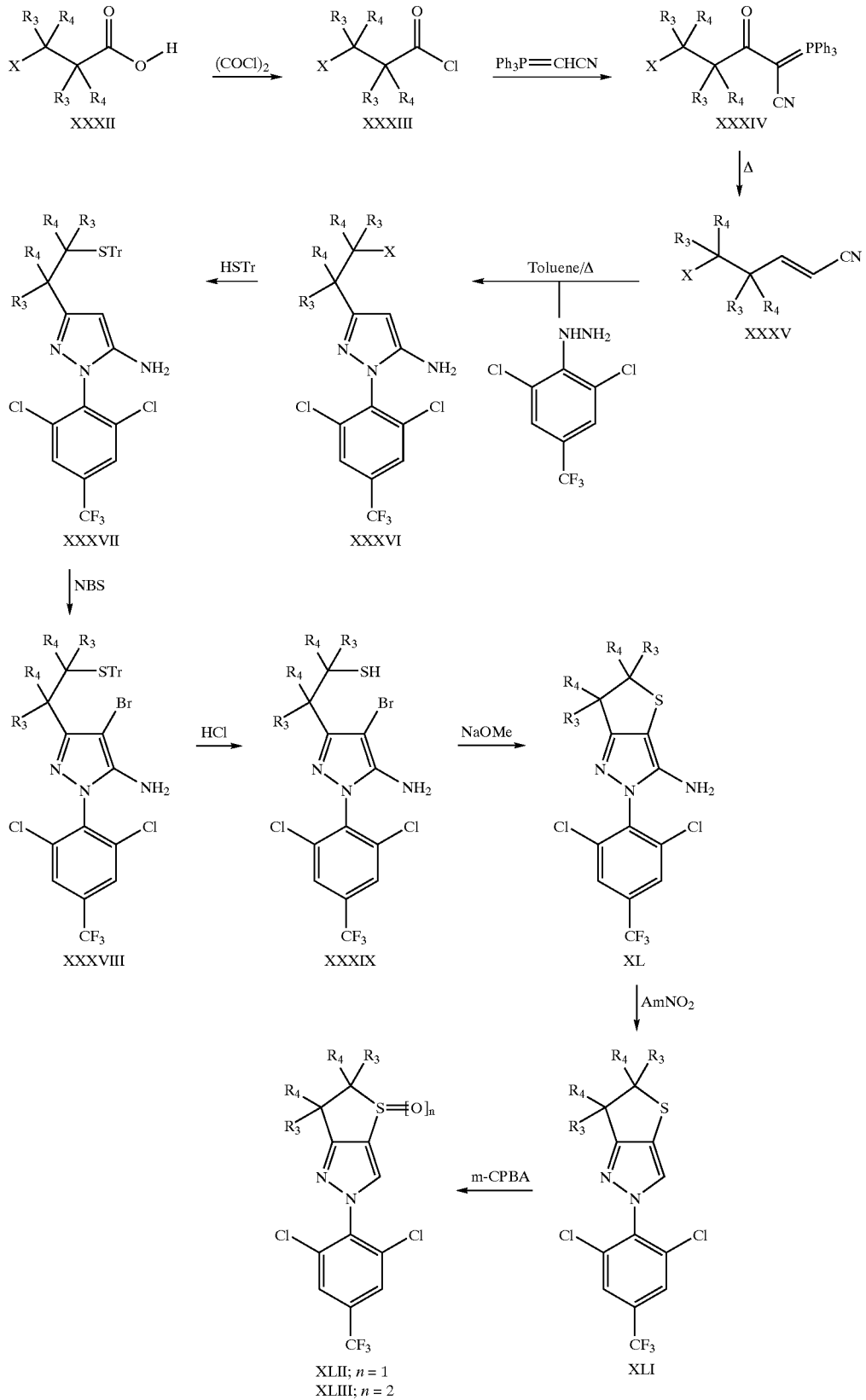

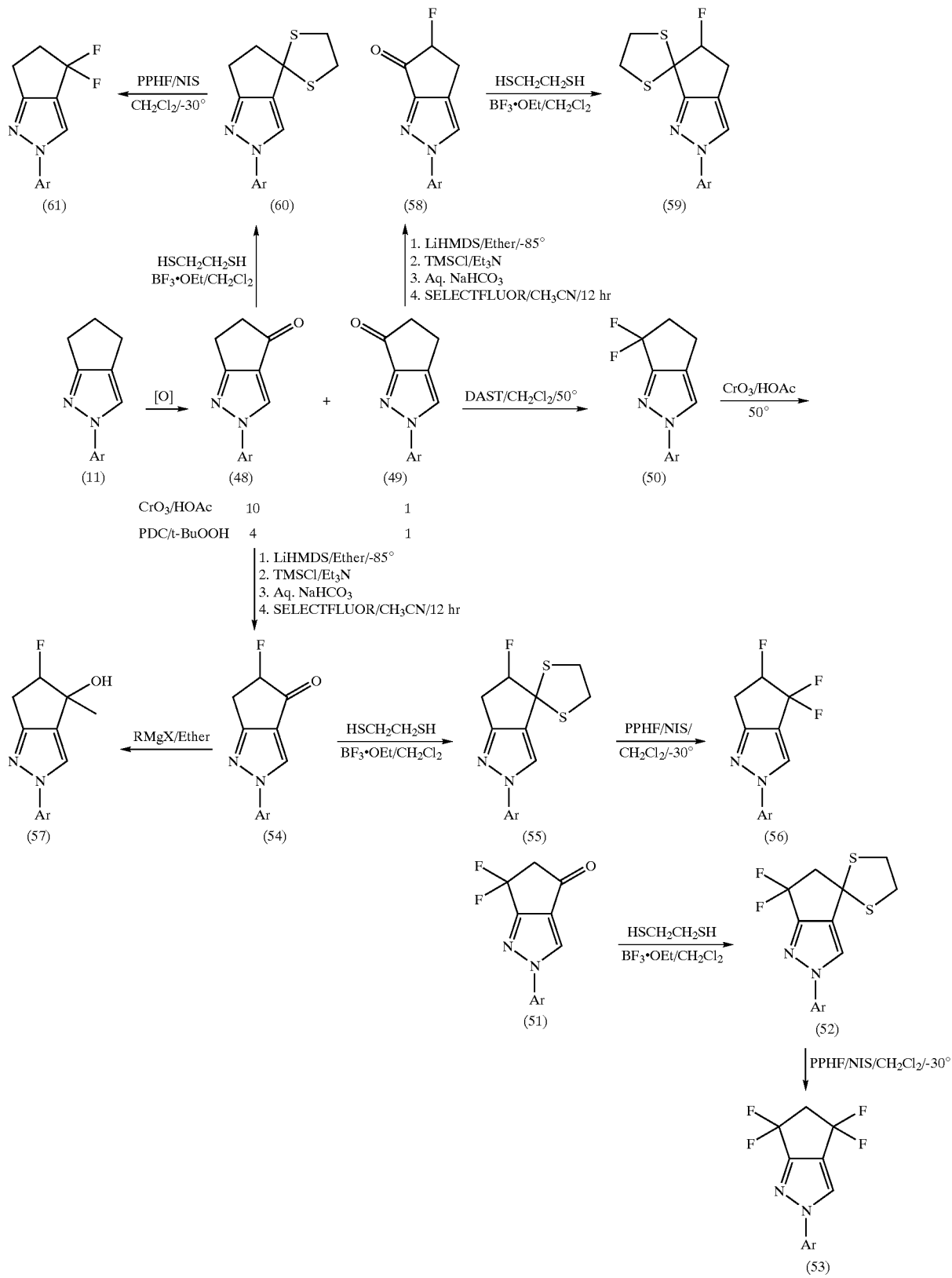
Scheme 9

Scheme 10
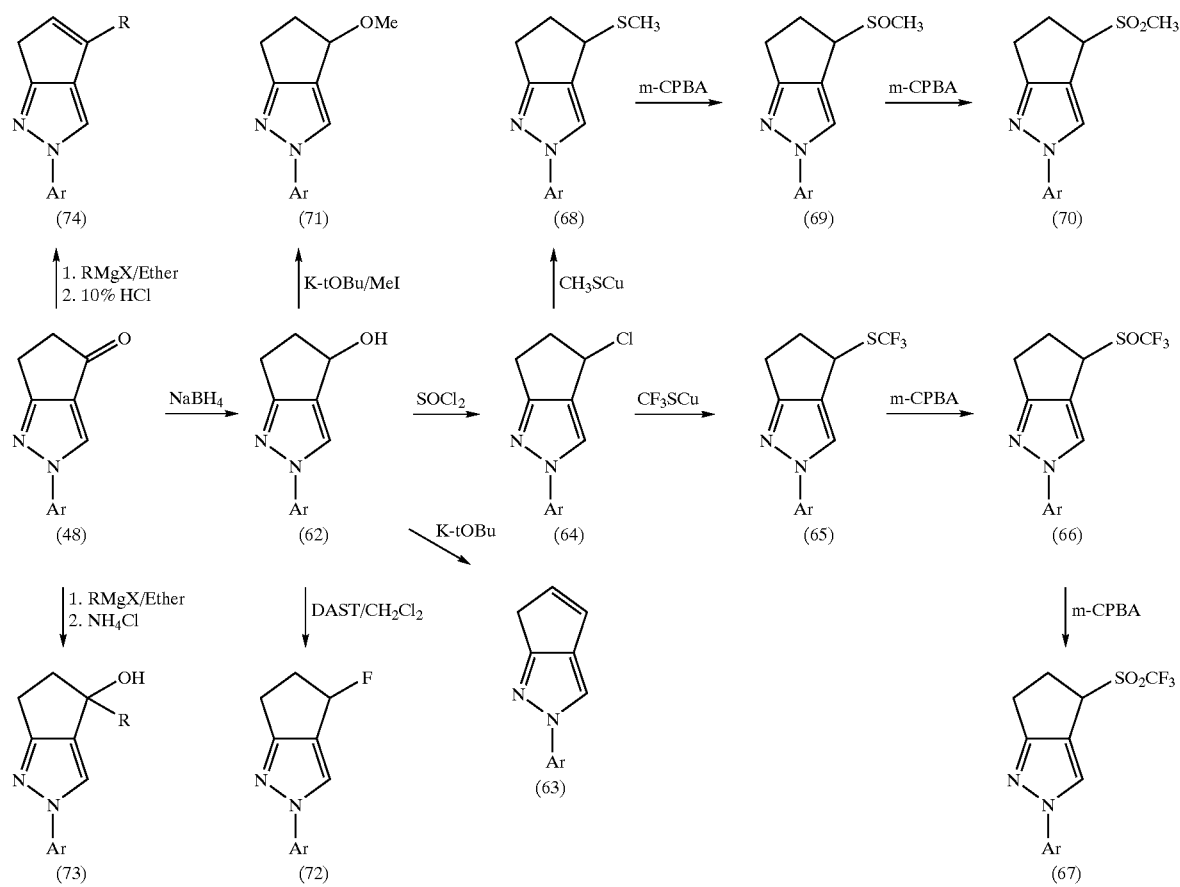
Scheme 11
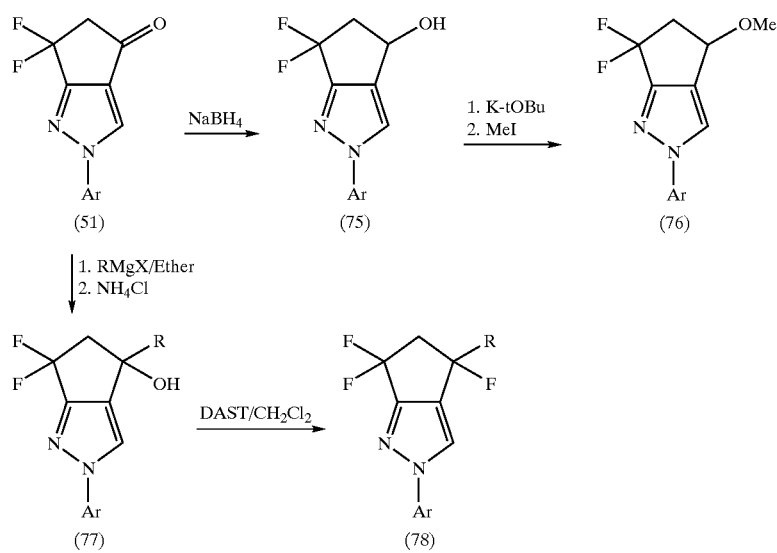

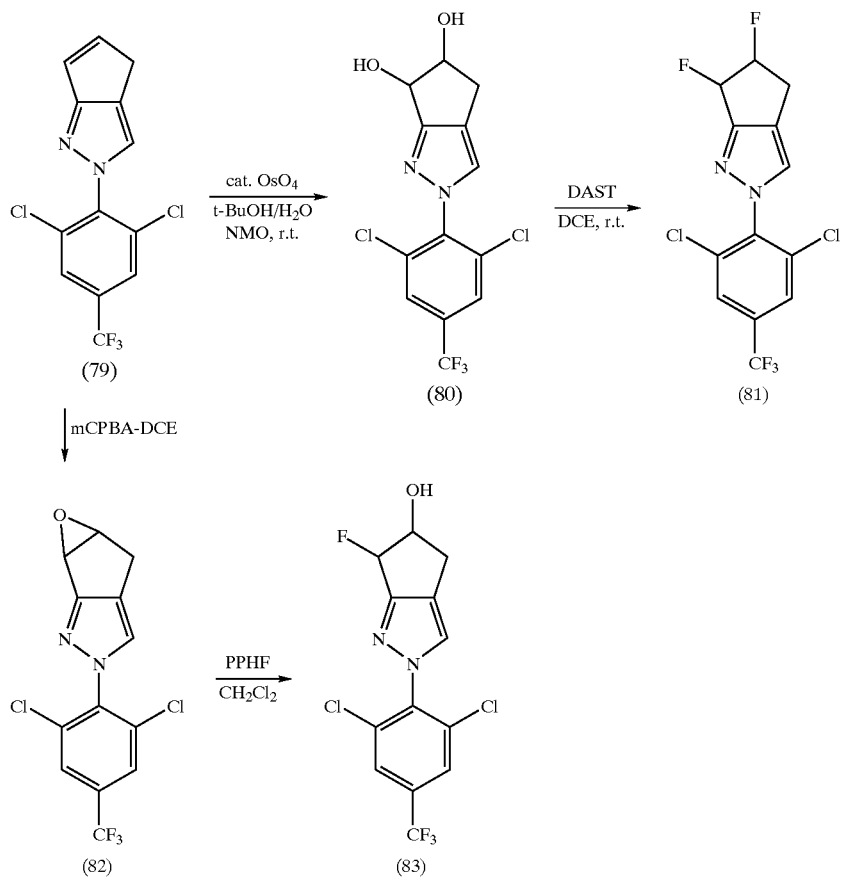
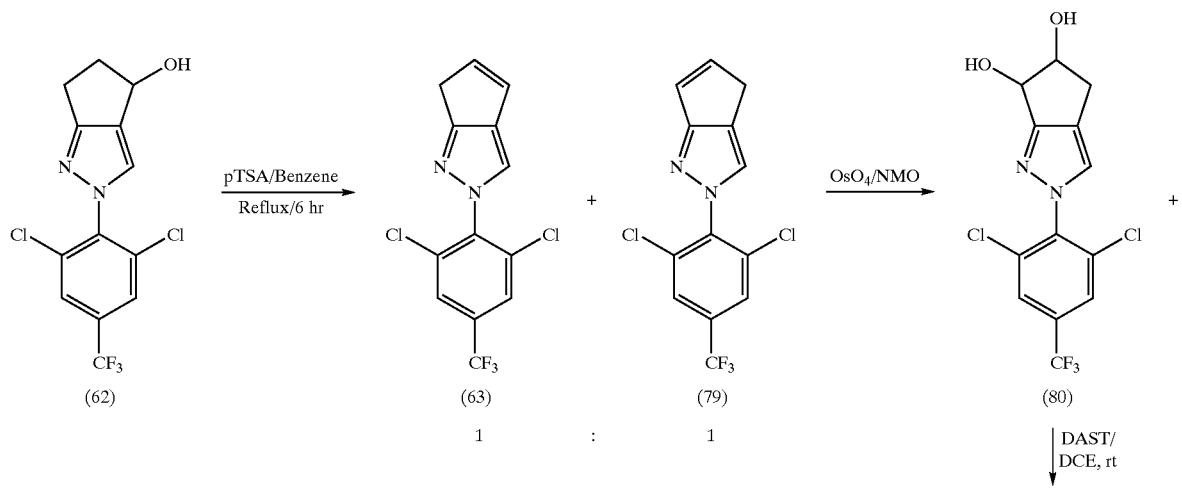

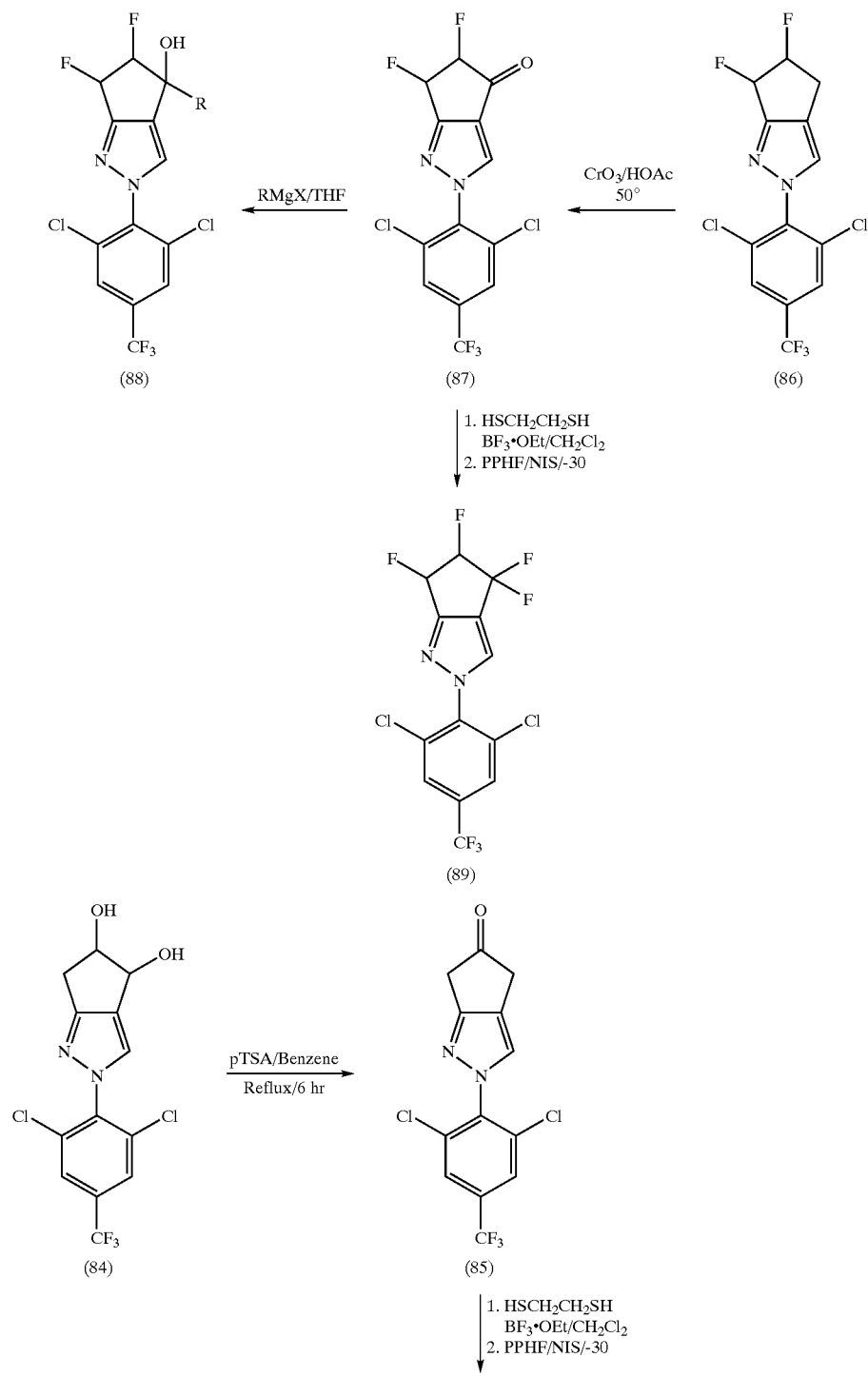

-continued
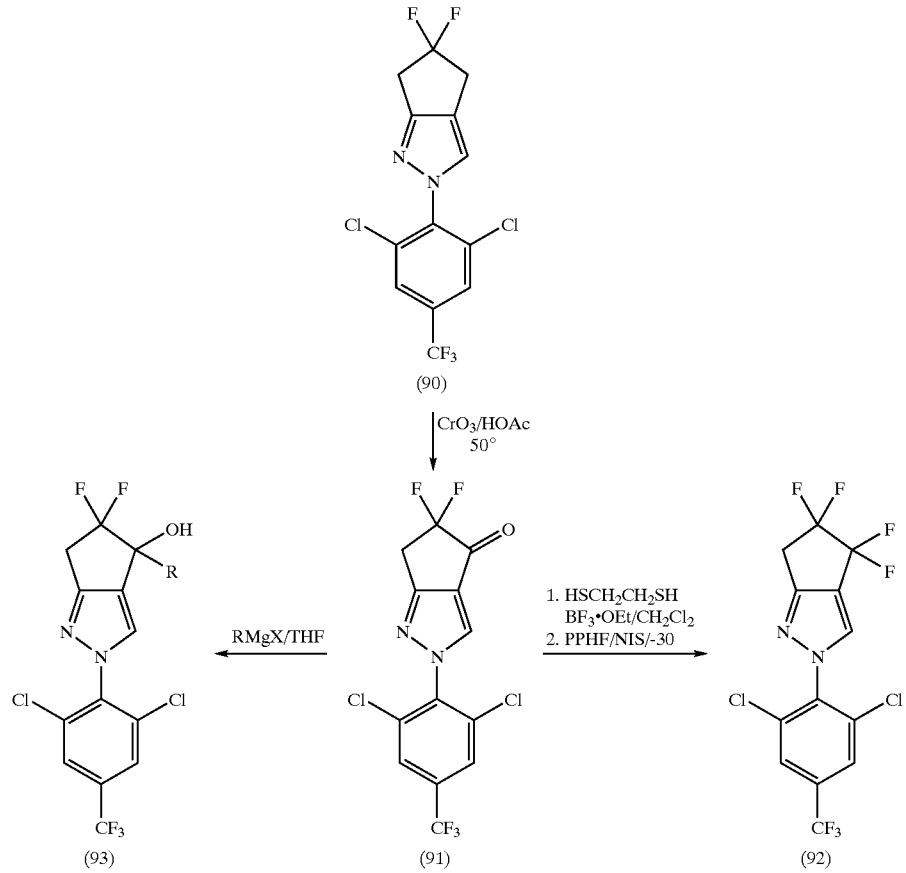
TABLE 1
Compounds of general formula I:
| Compound # | R |
|---|---|
| 1 | (thienopyrazole-amine structure) |
TABLE 1-continued
Compounds of general formula I:
| Compound # | R |
|---|---|
| (±), (+), (−)-1' | (S-oxide thienopyrazole-amine structure) |

TABLE 1-continued
Compounds of general formula I:
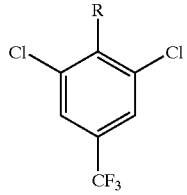
| Compound # | R |
|---|---|
| 1" | 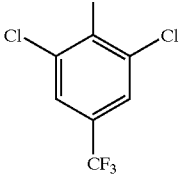 |
| 2 | 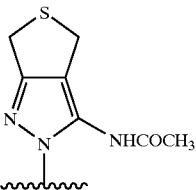 |
| (±), (+), (−)-2' | 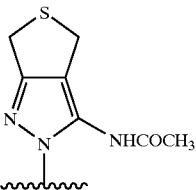 |
| 2" | 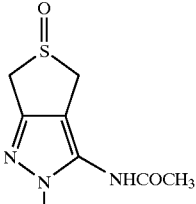 |
| 3 | 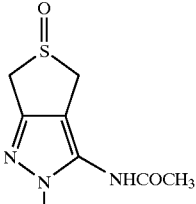 |
TABLE 1-continued
Compounds of general formula I:
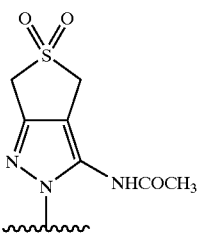
| Compound # | R |
|---|---|
| (±), (+), (−)-3' | 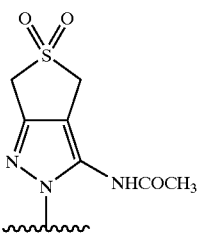 |
| 3" | 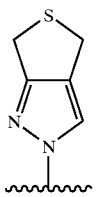 |
| 4 | 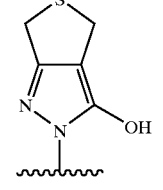 |
| (±), (+), (−)-4' | 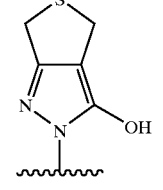 |
| 4" | 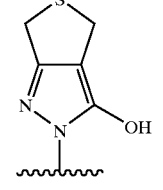 |

TABLE 1-continued
Compounds of general formula I:
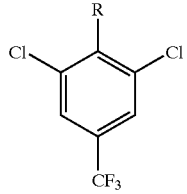
| Compound # | R |
|---|---|
| 5 | 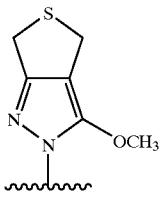 |
| (±), (+), (−)-5' | 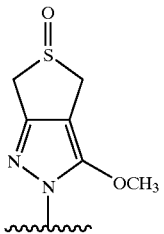 |
| 5" | 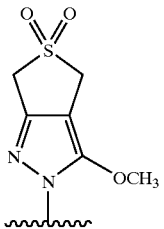 |
| 6 | 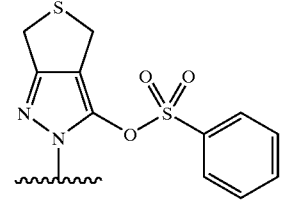 |
| (±), (+), (−)-6' | 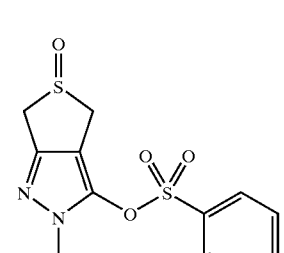 |
TABLE 1-continued
Compounds of general formula I:
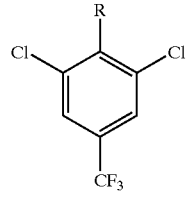
| Compound # | R |
|---|---|
| 6" | 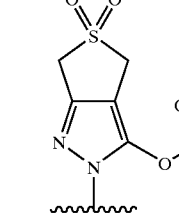 |
| 7 | 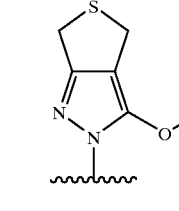 |
| (±), (+), (−)-7' | 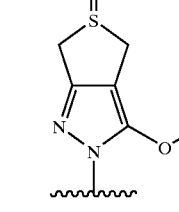 |
| 7" | 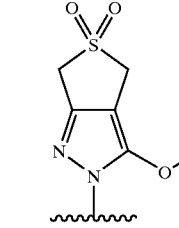 |
| 8 | 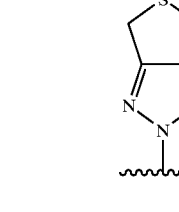 |

TABLE 1-continued

Compounds of general formula I:

(2,6-dichloro-4-trifluoromethylphenyl core with R substituent)

| Compound # | R |
|---|---|
| (±), (+), (−)-8' | 3-chloro-5-oxo-4,6-dihydro-2H-thieno[3,4-c]pyrazol-2-yl |
| 8" | 3-chloro-5,5-dioxo-4,6-dihydro-2H-thieno[3,4-c]pyrazol-2-yl |
| 9 | 3-bromo-4,6-dihydro-2H-thieno[3,4-c]pyrazol-2-yl |
| (±), (+), (−)-9' | 3-bromo-5-oxo-4,6-dihydro-2H-thieno[3,4-c]pyrazol-2-yl |
| 9" | 3-bromo-5,5-dioxo-4,6-dihydro-2H-thieno[3,4-c]pyrazol-2-yl |
| 10 | 4,5,6,7-tetrahydro-2H-thiopyrano[4,3-c]pyrazol-2-yl |
| (±), (+), (−)-10' | 5-oxo-4,5,6,7-tetrahydro-2H-thiopyrano[4,3-c]pyrazol-2-yl |
| 10" | 5,5-dioxo-4,5,6,7-tetrahydro-2H-thiopyrano[4,3-c]pyrazol-2-yl |
| 11 | 2,4,5,6-tetrahydrocyclopenta[c]pyrazol-2-yl |
| 12 | 6,6-dimethyl-2,4,5,6-tetrahydrocyclopenta[c]pyrazol-2-yl |
| 13 | 4,5,6,7-tetrahydro-2H-indazol-2-yl |

TABLE 1-continued

Compounds of general formula I:

(2,6-dichloro-4-trifluoromethylphenyl with R substituent)

| Compound # | R |
|---|---|
| 14 | 7,7-dimethyl-4,5,6,7-tetrahydro-2H-indazol-2-yl |
| 15 | 4,5,6,7,8-pentahydro-2H-cycloheptapyrazol-2-yl |
| 16 | 4H-indeno[1,2-c]pyrazol-2-yl (benzo-fused) |
| 17 | 4H-indeno[1,2-c]pyrazol-2-yl |
| 18 | 4-propyl-5,6-dihydro-4H-cyclopenta[c]pyrazol-2-yl |
| 19 | 4H-thieno[2,3-c]pyrazol-2-yl (dihydro) |
| 19" | corresponding sulfone (S(=O)₂) |
| (±), (+), (−)-19' | corresponding sulfoxide (S=O) |
| 20 | 5,5-difluoro-dihydrothieno[2,3-c]pyrazol-2-yl |
| 20" | 5,5-difluoro-dihydrothieno[2,3-c]pyrazol-2-yl sulfone |

TABLE 1-continued
Compounds of general formula I:
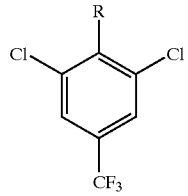
| Compound # | R |
|---|---|
| (±), (+), (−)-20′ | 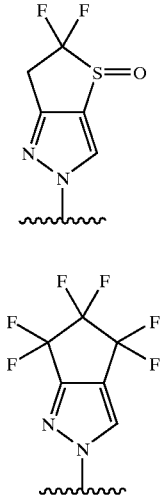 |
| 21 | 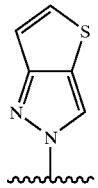 |
| 22 | 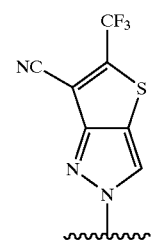 |
| 23 | 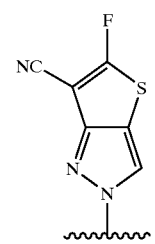 |
| 24 | 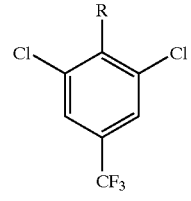 |
TABLE 1-continued
Compounds of general formula I:
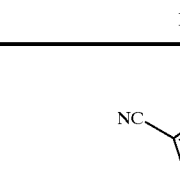
| Compound # | R |
|---|---|
| 25 | 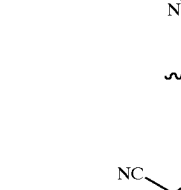 |
| 26 | 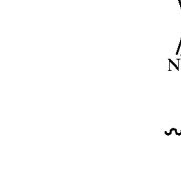 |
| 27 | 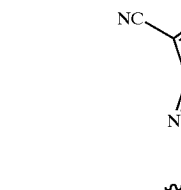 |
| 28 | 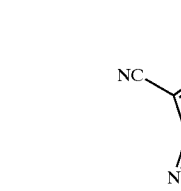 |
| 29 | 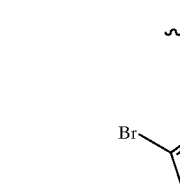 |

TABLE 1-continued
Compounds of general formula I:
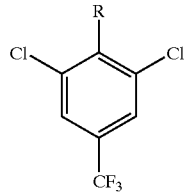
| Compound # | R |
|---|---|
| 30 | 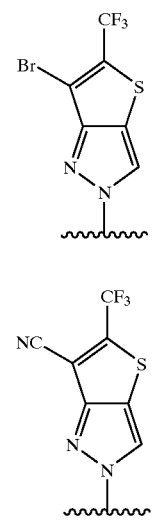 |
| 31 | 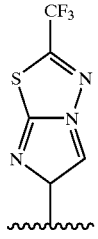 |
| 32 | 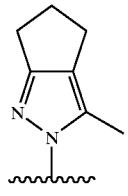 |
| 33 | 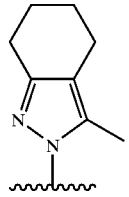 |
| 34 | 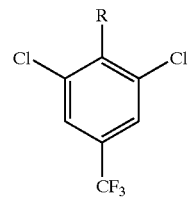 |
| 35 | 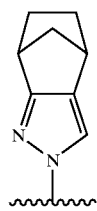 |
| 36 | 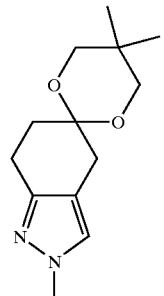 |
| 37 | 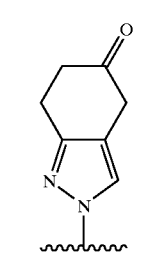 |
| 38 | 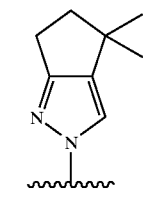 |
| 39 | 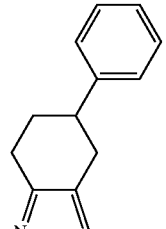 |

TABLE 1-continued

Compounds of general formula I:

(structure: 2,6-dichloro-4-trifluoromethylphenyl with R substituent)

| Compound # | R |
|---|---|
| 40 | 4-phenyl-5,6-dihydro-4H-cyclopenta[c]pyrazol-2-yl |
| 41 | 5,5-diethoxy-4,5,6,7-tetrahydro-2H-indazol-2-yl |
| (±), (+), (−)-42 | 4-methyl-5,6-dihydro-4H-cyclopenta[c]pyrazol-2-yl |
| 43 | spiro[1,3-dithiolane-2,5'-tetrahydroindazol]-2'-yl |
| 44 | 5-hydroxy-4,5,6,7-tetrahydro-2H-indazol-2-yl |
| 45 | 4,6,6-trimethyl-5,6-dihydro-4H-cyclopenta[c]pyrazol-2-yl |
| 46 | 2H-indazol-2-yl |
| 47 | tricyclic cyclopenta-fused pyrazolyl |

EXAMPLE 1

2-[2,6-Dichloro-4-(trifluoromethyl)phenyl]-4,6-dihydrothieno-[3,4-c]pyrazole-3-ylamine (1)

To a solution of 2,6-dichloro-4-(trifluoromethyl)phenyl hydrazine (2.45 g, 10 mmol) and 2-oxocyclopentanecarbonitrile (1.27 g, 10 mmol) in ethanol (40 mL) was added HCl (1:10 in water, 2 mL) and the mixture heated at reflux for 18 h. The solution was extracted with diethyl ether (100 mL) and washed with saturated NaHCO$_3$ (2×50 mL) and brine (2×50 mL). The organic phase was dried with MgSO$_4$, and the solvent removed under reduced pressure. Flash chromatography on silica (15% ethyl acetate:hexane), afforded the desired product as a yellow solid. (28%); $^1$H NMR (CDCl$_3$) δ 7.74 (2H, s), 3.8 and 4.0 (2H each, m); MS (M$^+$) 355.

EXAMPLE 2

3-Amino-2-[2,6-dichloro-4-(trifluoromethyl)phenyl]-4,6-dihydrothieno-[3,4-C]pyrazole-5-one (1')

To a solution of amine (1) (72 mg, 0.2 mmol) in CH$_2$Cl$_2$ (5 mL), m-CPBA (250 mg) was added. The reaction mixture was stirred at room temperature for 30 min. A solution of NaHCO$_3$ (10 mL) was added and the organic layer was separated and washed with water (2×10 mL), dried (Na$_2$SO$_4$) and concentrated to obtain the title compound as a white solid.(43%); $^1$H NMR (CDCl$_3$) δ 7.75 (2H, m), 3.6 and 4.4 (2H each, m); MS (M$^+$) 370.

EXAMPLE 3

N-{2-[2,6-Dichloro-4-(trifluoromethyl)phenyl]-4,6-dihydrothieno[3,4-c]pyrazol-3-yl}acetamide (2)

2-[2,6-dichloro-4-(trifluoromethyl)phenyl]-4,6-dihydrothiopheno[3,4-c]-pyazole-3-ylamine (354 mg, 1.0 mmol) was dissolved in CH$_2$Cl$_2$ (5 mL) under nitrogen and treated with triethylamine (0.3 mL). The resulting solution was cooled to 0° C., and acetyl chloride (0.17 mL) added dropwise. After 1 h, the reaction was worked up by dilution with water-ethyl ether, and the resulting mixture washed with NaOH (5%, 2×10 mL), HCl (5%, 2×10 mL), and brine (2×15 mL). The organic phase was dried (MgSO$_4$) and the solvent removed under reduced pressure. Crystallization from ethyl acetate-hexanes produced the desired acetamide as a white solid (65%); $^1$H NMR (CDCl$_3$) δ 7.75 (s, 2H), 4.04 (m, 4H each), 2.07 (s, 3H); MS (M$^+$) 396.

EXAMPLE 4

N-{2-[2,6-Dichloro-4-(trifluoromethyl)phenyl]-5-oxo-4,6-dihydrothieno-[3,4-c]pyrazol-3-yl}acetamide (2')

To a solution of acetamide (2) (145 mg, 0.37 mmol) in CH$_2$Cl$_2$ (5 mL), m-CPBA (500 mg) was added. The reaction mixture was stirred at room temperature for 30 min. and aq. NaHCO$_3$ (10 mL) was added and the organic layer separated and washed with water (2×10 mL), dried (Na$_2$SO$_4$) and concentrated to obtain the title compound as a white solid. (35%); $^1$H NMR (CDCl$_3$) δ 7.8 (2H, m), 4.33 and 4.46 (2H each, m), 2.12 (3H, s); MS (M$^+$) 428.

EXAMPLE 5

2-[2,6-Dichloro-4-(trifluoromethyl)phenyl]-4,6-dihydrothieno-[3,4-c]pyrazole (3)

A solution of 2-[2,6-dichloro-4-(trifluoromethyl)phenyl]-4,6-dihydrothieno-[3,4-c]pyrazole-3-ylamine (200 mg, 0.56 mmol) in DMF (5 mL) is warmed up to 65° C. and isoamyl nitrite (0.3 mL) was added dropwise and the reaction mixture stirred for 1 h at the same temperature. After cooling to room temperature, the mixture was extracted with ethyl ether (50 mL) and washed with brine (4×25 mL). After drying the organic phase (MgSO$_4$), volatile materials were removed under reduced pressure, and the residue was subjected to flash chromatography on silica, (10% ethyl acetate:hexanes). The product was recrystallized (hexane) and obtained in 76% yield. $^1$H NMR (CDCl$_3$) δ 7.72 (s, 2H), 4.01 and 4.09 (m, 2H each); MS (M$^+$) 339.

EXAMPLE 6

2-[2,6-Dichloro-4-(trifluoromethyl)phenyl]-4,6-dihydrothieno-[3,4-c]pyrazole-5-one ((±), (+), (−)-3')

To a solution of compound (3) (41 mg, 0.11 mmol) in CH$_2$Cl$_2$ (3 mL) m-CPBA (31.3 mg, 0.13 mmol) was added at −78° C. under N$_2$. After 30 min. the reaction mixture was allowed to warm to −30° C. and stirred at −30° C. until the starting material disappeared completely. Aqueous Na$_2$CO$_3$ (10 mL) was then added and the organic phase was separated. The organic layer was washed with aq. Na$_2$CO$_3$ (10×4 mL), dried, concentrated to obtain a solid which was purified by flash chromatography on silica (20% EtOAc:hexane) to obtain the title compound (60%). $^1$H NMR (CDCl$_3$) δ 7.78 (s, 2H), 7.45 (s, 1H), 7.53 (m, 2H), 4.01 (d, J=7.8 Hz, 1H), 3.88 (d, 7.8 Hz, 1H); MS (M$^+$) 355.

EXAMPLE 7

2-[2,6-Dichloro-4-(trifuoromethyl)phenyl]-4,6-dihydrothieno-[3,4-c]pyrazole-5,5-dione (3")

To a solution of compound (3) (47 mg, 0.13 mmol) in CH$_2$Cl$_2$ (3 mL), m-CPBA (84 mg, 0.48 mmol) was added at −78° C. under N$_2$. After 30 min. the reaction mixture was allowed to warm to −30° C. and stirred at −30° C. until the starting material disappeared completely. Aq. Na$_2$CO$_3$ (10 mL) was then added and the organic phase was separated. The organic layer was washed with aq. Na$_2$CO$_3$ (10×4 mL), dried, concentrated to obtain a solid which was purified by flash chromatography on silica (8% EtOAc: Hexane) to obtain the title compound (80%). $^1$H NMR (CDCl$_3$) δ 7.78 (s, 2H), 7.56 (s, 1H), 4.42 (s, 2H), 4.40 (s, 2H); MS (M$^+$) 371.

EXAMPLE 8

2-[2,6-Dichloro-4-(trifluoromethyl)phenyl]-4,6-dihydrothieno-[3,4-c]pyrazole-3-yl benzenesulfonate (6)

2,6-dichloro-4-(trifluoromethyl)phenylhydrazine (245 mg, 1 mmol) and 4-carbomethoxy-3-thiophenone (160 mg, 1 mmol) in MeOH was heated for 12 hr. The reaction mixture was allowed to cool to room temperature and a white hydrazone precipitate formed which was collected by suction filtration. The above-collected hydrazone precipitate (120 mg, 0.3 mmol) was dissolved in MeOH (5 mL) and NaOMe (20 mg) was added. The resulting mixture was then heated at reflux for 12 hr. The reaction mixture was allowed to cool to room temperature and poured into ice-water (10 mL) and acidified with AcOH. The precipitate formed was collected by suction filtration to obtain the title compound (4) (36%). Pyrazolone (4) (70 mg, 0.2 mmol) was dissolved in CH$_2$Cl$_2$ (5 mL) and Et$_3$N (0.1 mL). The resulting mixture was cooled to 0° C. and treated dropwise with PhSO$_2$Cl (0.05 mL, 0.4 mmol). The reaction mixture was allowed to warm to room temperature and stirred for 1 h. Water (10 mL) was then added and the organic phase was separated, dried and concentrated. The solid obtained was purified by flash chromatography on silica (10% EtOAc:Hexane) to obtain the title compound (6) (80%). $^1$H NMR (CDCl$_3$) δ 7.85 (m, 2H), 7.65 (s, 2H), 3.4 and 4.3 (m, 2H each), 7.4 (m, 2H); MS (M$^+$) 459.

EXAMPLES 9–14

Preparation of (10), (11), (12), (13), (15), (16)

To a solution of diisopropyl amine (0.14 mL, 1 mmol) in THF (5 mL) at −78° C. was added BuLi (0.62 mL, 1 mmol) and the resulting mixture was warmed to 0° C. and stirred for 15 min at 0° C. The mixture was then cooled back to −78° C. and the appropriate ketone (1 mmol) in THF (1 mL) was added dropwise and stirred at −78° C. for 30 min. at which time, TMSCl (0.12 mL, 1.2 mmol) was added. The resulting mixture was allowed to warm to room temperature.

After stirring for 30 min. at room temperature, the reaction mixture was poured into ice-cold, saturated NaHCO$_3$ and product (silyl enol ether) was extracted with ether (10×3 mL), dried and distilled underreduced pressure (where ever possible) or used directly after drying thoroughly. The thus obtained silyl enol ether (1.2 mmol) and trimethylorthoformate (0.1 mL, 1 mmol) in CH$_2$Cl$_2$ (2 mL) were cooled to −78° C. under N$_2$ and TMSI (0.01 mL, 0.1 mmol) was added. The resulting mixture was stirred at −78° C. for 1 h and poured into ice-cold saturated NaHCO$_3$ (10 mL). The organic layer was separated, dried and concentrated to obtain the corresponding 2-dimethoxyacetalketone. The keto acetal (1 mmol) and 2,6-dichloro-4-trifluoromethylphenylhydrazine (245 mg, 1 mmol) in MeOH (10 mL) were heated under reflux for 3 h. Concentrated sulfuric acid (5 drops) was added and heating was continued at reflux for an additional 1 h. The reaction mixture was allowed to cool to room temperature and saturated NaHCO$_3$ (0.5 mL) was added and MeOH removed under reduced pressure. The residue obtained was partitioned between CH$_2$Cl$_2$ and water. The CH$_2$Cl$_2$ layer was separated and concentrated to obtain a dark residue which was purified by flash chromatography on silica.

2-[2,6-Dichloro-4-(trifluoromethyl)phenyl]-2H,4H,6H,7H-thiano[4,3-c]pyrazole (10)

The title compound was synthesized using tetrahydrothiopyran-4-one as the starting ketone: yield 53%. $^1$H NMR (CDCl$_3$) δ 7.68 (s, 2H), 7.18 (s, 1H), 2.89 (t, J=7.2 Hz, 2H), 2.84 (s, 2H), 2.67 (t, J=7.2 Hz, 2H); MS (M$^+$) M+353.3.

2-[2,6-Dichloro-4-(trifluoromethyl)phenyl]-2,4,5,6-tetrahydrocyclopenta[c]pyrazole (11)

The title compound was synthesized using cyclopentanone as the starting ketone: yield 74%. $^1$H NMR (CDCl$_3$) δ 7.73 (s, 2H), 7.15 (s, 1H), 2.86 (t, J=7.2 Hz, 2H), 2.78 (t, J=7.2 Hz, 2H), 2.51 (m, 2H)); MS (M$^+$) 321.3.

2-[2,6-Dichloro-4-(trifluoromethyl)phenyl]-6,6-dimethyl-2,4,5,6-tetrahydrocyclopenta[c]pyrazole (12)

The title compound was synthesized using 2,2-dimethylcyclopentanone as the starting ketone: yield 64%. $^1$H NMR: (CDCl$_3$) δ 7.80 (s, 2H), 7.50 (s, 1H), 2.65 (t, J=7.0 Hz, 2H), 2.34 (t, J=7.0 Hz, 2H), 1.14 (s, 6H)); MS (M$^+$) 351.20.

2-[2,6-Dichloro-4-(trifluoromethyl)phenyl]-4,5,6,7-tetrahydro-2H-indazole (13)

The title compound was synthesized using cyclohexanone as the starting ketone: yield 57%. $^1$H NMR (CDCl$_3$) δ 7.73 (s, 2H), 7.60 (s, 1H), 2.5 (m, 2H), 2.34 (m, 2H), 1.8 (s, 4H); MS (M$^+$) 335.3.

2-[2,6-Dichloro-4-(trifluoromethyl)phenyl]-2,4,5,6,7,8-hexahydrocyclohepta[c]pyrazole (15)

The title compound was synthesized using cycloheptanone as the starting ketone: yield 48%. $^1$H NMR (CDCl$_3$) δ 7.73 (s, 2H), 7.653 (s, 1H), 2.5 (m, 2H), 2.34 (m, 2H), 1.8 (s, 6H); MS (M$^+$) 349.8.

2-[2,6-Dichloro-4-(trifluoromethyl)phenyl]indeno[1,2-c]pyrazole (16)

The title compound was synthesized using 1-indanone as the starting ketone: yield 48%. $^1$H NMR (CDCl$_3$) δ 7.80 (s, 2H), 7.60 (m, 2H), 7.34 (m, 2H), 7.10 (s, 1H), 3.80 (s, 3H); MS (M$^+$) 369.20.

EXAMPLES 15 and 16

Preparation of (22) and (46)

The appropriate 2-formyl-3-nitroarene (1 mmol) and 2,6-dichloro-4-trifluoromethylaniline (230 mg, 1 mmol) and toluenesulfonic acid (5 mg) in benzene (15 mL) was heated at reflux for 12 hr. Benzene was removed under reduced pressure and the resulting residue was purified by flash chromatography on silica (20% EtOAc:Hexane) to obtain the corresponding imine as yellow needles. The thus obtained imine (3 mmol), triethylphosphite (1.5 g, 9 mmol) and t-butylbenzene (10 mL) was heated under reflux for 14 hr. Solvent was removed under reduced pressure and the product purified by flash chromatography on silica (EtOAc:hexanes).

2-[2,6-Dichloro-4-(trifluoromethyl)phenyl]-2H-thieno[3,2-c]pyrazole (22)

The title compound was synthesized using 2-formyl-3-nitrothiophene as the starting nitroarene: yield 41%. $^1$H NMR (CDCl$_3$) δ 7.78 (s, 2H), 7.75 (s, 1H), 7.49 and 7,2 (d, J=4 Hz, 1H each); MS (M$^+$) 337.4.

2-[2,6-Dichloro-4-(trifluoromethyl)phenyl]-2H-indazole (46)

The title compound was synthesized using 2-formyl-3-nitrobenzene as the starting nitroarene: yield 61%. $^1$H NMR (CDCl$_3$) δ 8.1 (s, 1H), 7.8 (m, 4H), 7.13 and 7.35 (m, 1H each; MS (M$^+$) 331.2.

EXAMPLE 17

2-[2,6-Dichloro-4-(trifluoromethyl)phenyl]-3-methyl-2,4,5,6-tetrahydrocyclopenta[c]pyrazole (33)

2-Acetyl cyclopentanone (0.12 mL, 1 mmol) and 2,6-dichloro-4-trifluoromethylphenylhydrazine (245 mg, 1 mmol) in EtOH (10 mL) was heated under reflux for 12 hr. EtOH was removed under reduced pressure and the product purified by flash chromatography on silica (10% EtOAc:Hexane): yield 75%. $^1$H NMR (CDCl$_3$) δ 7.8 (s, 2H), 2.6 (m, 6H each), 2.2 (s, 3H); MS (M$^+$) 335.

EXAMPLE 18

2-[2,6-Dichloro-4-(trifluoromethyl)phenyl]-3-methyl-4,5,6,7-tetrahydro-2H-indazole (34)

2-Acetylcyclohexanone (0.12 mL, 1 mmol) and 2,6-dichloro-4-trifluoromethylphenylhydrazine (245 mg, 1 mmol) in EtOH (10 mL) was heated under reflux for 12 hr. EtOH was removed under reduced pressure and the product purified by flash chromatography on silica (10% EtOAc:Hexane): yield 67%. $^1$H NMR (CDCl$_3$) δ 7.8 (s, 2H), 2.7 and 2.05 (m, 2H each), 2.05 (s, 3H), 1.9 (m, 4H); MS (M$^+$) 349.

EXAMPLES 19–23

General Procedure for the Preparation of (35), (36), (39), (45), and (47)

To 5.5 mL (0.05 mol) of trimethylorthoformate at −30° C. under N$_2$ was added dropwise, with stirring over period of 10 min, a solution of BF$_3$OEt$_2$ (7.5 mL, 0.06 mol) in CH$_2$Cl$_2$ (20 mL). The reaction mixture was allowed to warm to 0° C. and kept at this temperature for 15 min. and then cooled back to −78° C. The appropriate ketone (0.025 mol) in $CH_2Cl_2$ (10 mL) was then added followed by diisopropylethylamine (0.075 mol) over 30 min. The resulting mixture was stirred at −78° C. for 1 h and poured into cold $NaHCO_3$ (500 mL) and $CH_2Cl_2$ (200 mL) with vigorous stirring. The organic phase was separated, washed with water (3×100 mL), dried and concentrated to obtain the corresponding 2-acetalketone which was directly used for the condensation with 2,6-dichloro-4-trifluoromethylphenylhydrazine as described above for the synthesis of (10), (11), (12), (13), (15), (16) and (17).

3,4-Diaza-4-[2,6-dichloro-4-(trifluoromethyl)phenyl]tricyclo-[5.2.1.0$^{2,6}$]deca-2,5-diene (35)

The title compound was synthesized using norcamphor as the starting ketone: yield 52%. $^1$H NMR ($CDCl_3$) δ 7.75 (s, 2H), 7.08 (s, 1H), 3.48 (d, J=7.4 Hz, 2H), 2.1 (d, J=7.0 Hz, 1H), 1.97 (d, J=7.0 Hz, 1H), 1.86 (d, J=7.0 Hz, 1H), 1.30 (m, 3H); MS (M$^+$) 347.3.

8-[2,6-Dichloro-4-(trifluoromethyl)phenyl]-5,5,9-trimethylspiro-[1,3-dioxane]-2,5'-2,4',5,6',7'-tetrahydro-2H-indazole (36)

The title compound was synthesized using 1,4-cyclohexenedione mono-2,2-dimethyltrimethylene ketal as the starting ketone: yield 40%. $^1$H NMR ($CDCl_3$) δ 7.82 (s, 2H), 7.23 (s, 1H), 3.75 (d, J=7.0 Hz, 2H), 3.54 (t, J=7.8 Hz, 2H), 3.08 (s, 2H), 1.88 (t, J=7.2 Hz, 2H), 2.30 (t, J=7.2 Hz, 2H), 1.18 (s, 3H), 0.98 (s, 3H); MS (M$^+$) 435.4.

2-[2,6-Dichloro-4-(trifluoromethyl)phenyl]-5-phenyl-4,5,6,7-tetrahydro-2H-indazole (39)

The title compound was synthesized using 4-phenylcyclohexanone as the starting ketone: yield 66%. $^1$H NMR ($CDCl_3$) δ 7.75 (s, 2H), 7.30 (m, 6H), 3.06 (d, J=7.2 Hz, 2H), 3.01 (m, 1H), 2.25 (m, 2H), 1.26 (t, J=7.4 Hz, 2H); MS (M$^+$) 411.5.

2-[2,6-Dichloro-4-(trifluoromethyl)phenyl]-4,6,6-trimethyl-2,4,5,6-tetrahydrocyclopenta[c]pyrazole (45)

The title compound was synthesized using 2,2,4-trimethylcyclohexanone as the starting ketone: yield 70%. $^1$H NMR: ($CDCl_3$) δ 7.67 (s, 2H), 7.40 (s, 1H), 3.12 (m, 1H), 2.49 (m, 1H), 1.97 (m, 1H), 1.23 (d, J=7.8 Hz, 3H), 1.11 (s, 3H), 1.08 (s, 3H); MS (M$^+$) 363.5.

5,6-Diaza-5-[2,6-dichloro-4-(trifluoromethyl)phenyl]tetracyclo-[8.2.1.0$^{2,9}$.0$^{3,7}$]trideca-3,6-diene (47)

The title compound was synthesized using tricyclo [5.2.1.0$^{2,6}$]decan-8-one as starting ketone: yield 56%. $^1$H NMR ($CDCl_3$) δ 7.60 (s, 2H), 6.95 (s, 1H), 3.15 (d, J=7.8 Hz, 2H), 2.10 (m, 6H), 1.55 (m, 2H), 1.16 (m, 2H); MS (M$^+$) 387.40.

EXAMPLE 24

2-[2,6-Dichloro-4-(trifluoromethyl)phenyl]-2,4,6,7-tetrahydroindazole-5-one (37)

Compound (36) (20 mg) was dissolved in THF (2 mL), $CH_3OH$ (1 mL), $H_2SO_4$ (0.1 mL) and water (0.5 mL). The resulting mixture was stirred at room temperature for 48 h and poured into 10% $NaHCO_3$ (20 mL). The product was extracted with $CH_2Cl_2$ (3×10 mL). The organic layer was combined, dried and concentrated. The residue obtained was purified by flash chromatography on silica (20% EtOAc:Hexane): yield 84%. $^1$H NMR ($CDCl_3$) δ 7.75 (s, 2H), 7.35 (s, 1H), 3:58 (s, 2H), 3.18 (t, J=7.2 Hz, 2H), 2.89 (t, J=7.2 Hz, 2H); MS (M$^+$) 349.4.

EXAMPLES 25–28

Preparation of (18), (38), (40) and (42)

An appropriate Grignard or organolithium reagent (2 mmol) was slowly added to CuBr.Me$_2$S in THF (10 mL) at −30° C. The resulting solution was stirred at −30° C. for 1 h and cooled back to −78° C. and HMPA (0.17,2 mmol) was added drop wise. A mixture of an appropriate enone (1 mmol) and TMSCl (0.24 mL, 2.4 mmol) was then added dropwise and the resulting mixture stirred for 30 min. and then warmed to −40° C. and stirred for an additional 30 min. Triethylamine (0.69 mL, 5 mmol) was then added to the reaction mixture followed by a mixture of ether:hexane (1:1 10 mL) and water (1 mL). The resulting mixture was allowed to warm to room temperature and passed through a pad of Celite. The Celite pad was washed with ether (3×5 mL). The ether layers were combined, dried and concentrated in vacuo to obtain the corresponding silyl enol ether. The thus obtained silyl enol ether was converted into 2-acetalketone which was then condensed with hydrazine as described in the latter part of the general procedure for the preparation of (10), (11), (12), (13), (15), (16) and (17).

2-[2,6-Dichloro-4-(trifluoromethyl)phenyl]-4-propyl-2,4,5,6-tetrahydrocyclopenta[c]pyrazole (18)

The title compound was synthesized using 2-cyclopentenone as the starting enone: yield 47%. $^1$H NMR ($CDCl_3$) δ 7.66 (s, 2H), 7.1 (s, 1H), 3.05 (m, 1H), 2.8 (m, 3H), 2.59 (m, 1H), 2.04 (m, 1H), 1.4 (m, 3H), 0.95 (t, J=7.8 Hz, 3H); MS (M$^+$) 363.5.

2-[2,6-Dichloro-4-(trifluoromethyl)phenyl]-4,4-dimethyl-2,4,5,6-tetrahydrocyclopenta[c]pyrazole (38)

The title compound was synthesized using a methyl Grignard or methyl lithium reagent and 3-methylcyclopentenone as the starting enone: yield 48%. $^1$H NMR ($CDCl_3$) δ 7.73 (s, 2H), 7.48 (s, 1H), 2.42 and 2.64 (t, J=6.6 Hz, 2H each), 1.3 and 1.5 (s, 3H each); MS (M$^+$) 349.4.

2-[2,6-Dichloro-4-(trifluoromethyl)phenyl]-4-phenyl-2,4,5,6-tetrahydrocyclopenta[c]pyrazole (40)

The title compound was synthesized using a phenyl Grignard or phenyl lithium reagent and cyclopentenone as the starting enone: yield 22%. $^1$H NMR: ($CDCl_3$) δ 7.77 (s, 2H), 7.53 (s, 1H), 7.73–7.26 (m, 5H), 4.41 (dd, J$_1$=7.6, J$_2$=5.8), 3.16 (m, 1H), 2.98 (m, 2H), 2.75 9m, 1H), 2.52 (m, 1H); MS (M$^+$+1) 397.1.

2-[2,6-Dichloro-4-(trifluoromethyl)phenyl]-4-methyl-2,4,5,6-tetrahydrocyclopenta[c]pyrazole (42)

The title compound was synthesized using a methyl Grignard or methyl lithium reagent and cyclopentenone as the starting enone; yield 64%. $^1$H NMR: ($CDCl_3$) δ 7.75 (s, 2H), 7.05 (s, 1H), 3.15 (m, 1H), 2.85 (m, 2H), 1.97 (m, 2H), 1.23 (d, J=7.8 Hz, 3H); MS (M$^+$) 335.15.

EXAMPLE 29–32

Preparation of (48), (49), (51) and (61)

A mixture of an appropriate cyclopentane derivative (11), (50) or (60) (10.00 mmol), chromium (VI) oxide (3.00 g, 30.00 mmol) and HOAc (30 mL) is allowed to stir at 50° C. for 16 hours. The solvent is removed in vacuo and residue is dissolved in EtOAc (100 mL) and washed with water (100 mL), saturated aq. NaHCO$_3$ (10 mL), and brine (100 mL) subsequently. The organic layer is dried (MgSO$_4$), concentrated and the resulting residue is purified on silica (methylene chloride: ethyl acetate 19:1).

2-[2,6-Dichloro-4-(trifluoromethyl)phenyl]-5,6-dihydro-2H-cyclopenta[c]pyrazol-4-one (48)

The title compound was synthesized using cyclopentane (11) as the starting alcohol: yield 78%. $^1$H NMR (CDCl$_3$); δ 7.83 (s, 1H), 7.79 (s, 2H), 3.18 (m, 2H), 3.09 (m, 2H); MS (M$^+$+1) 335.4.

2-[2,6-Dichloro-4-(trifluoromethyl)phenyl]-4,5-dihydro-2H-cyclopenta[c]pyrazol-6-one (49)

The title compound was synthesized using cyclopentane (11) as the starting alcohol: yield 8%. $^1$H NMR (CDCl$_3$); δ 7.83 (s, 2H), 7.56 (s, 1H), 3.12 (m, 4H); MS (M$^+$+1): 335.4.

2-[2,6-Dichloro-4-(trifluoromethyl)phenyl]-6,6-difluoro-5,6-dihydro-2H-cyclopenta[c]pyrazol-4-one (51)

The title compound was synthesized using cyclopentane (50) as the starting alcohol: yield 70%. $^1$H NMR (CDCl$_3$); δ 7.89 (s, 1H), 7.81 (s, 2H), 3.56 (t, 2H, J=10 Hz); MS (M$^+$+1) 371.4.

EXAMPLES 33–35

Preparation of (50), (72), and (78)

A mixture of an appropriate ketone (49) or alcohol (62) or (77) (1.76 mmol), diethylaminosulfur trifluoride (DAST) (1.7 g, 10.5 mmol) and CH$_2$Cl$_2$ (3 mL) was heated at 50° C. After 16 hours, the reaction was cooled to 10° C. and CH$_2$Cl$_2$ (30 mL) was added followed by dropwise addition of methanol (2 mL). The resulting solution was washed with 5% aqueous NaHCO$_3$ (10 mL), dried (MgSO$_4$) and concentrated in vacuo. The residue was purified on silica (hexane:ethyl acetate 90:10).

2-[2,6-Dichloro-4-(trifluoromethyl)phenyl]-6,6-difluoro-2,4,5,6-tetrahydrocyclopenta[c]pyrazole (50)

The title compound was synthesized using cyclopentane (49) as the starting ketone: yield 83%. $^1$H NMR (CDCl$_3$); δ 7.75 (s, 2H), 7.30 (s, 1H), 3.03–2.96 (m, 4H); MS (M$^+$+1) 357.3.

2-[2,6-Dichloro-4-(trifluoromethyl)phenyl]-4-fluoro-2,4,5,6-tetrahydrocyclopenta[c]pyrazole (72)

The title compound was synthesized using cyclopentane (62) as the starting alcohol: yield 35%. $^1$H NMR (CDCl$_3$); δ 7.74 (s, 2H), 7.47 (s, 1H), 5.13 (d, J=26 Hz, 1H), 3.08 (m, 1H), 2.81 (m, 2H), 2.60 (m 1H); MS (M$^+$+1) 339.3.

2-[2,6-Dichloro-4-(trifluoromethyl)phenyl]-4,6,6-trifluoro-4-methyl-2,4,5,6-tetrahydrocyclopenta[c]pyrazole (78)

The title compound was synthesized using cyclopentane (77) as the starting alcohol: yield 40%. $^1$H NMR (CDCl$_3$); δ 7.78 (s, 2H), 7.58 (s, 1H), 3.35 (m, 1H), 3.14 (m, 1H), 1.89 (d, 3H, J=40 Hz); MS (M$^+$+1) 389.5.

EXAMPLES 36 and 37

General Procedure for the Preparation of (54) and (58)

To a magnetically stirred solution of appropriate ketone (48) (670 mg, 2 mmol) in 1:1 mixture of ether/THF (10 mL) at –85° C. (bath temperature) LiHMDS (2 mL, 2 mmol) was added dropwise over 10 min. The reaction mixture was stirred at –85° C. for 15 min. and TMSCl (1.2 mL, 10 mmol) was added. The resulting mixture was stirred at –85° C. for 15 min. and Et$_3$N (2.5 mL) was added and stirred at –78° C. for 30 min. Ether (10 mL) and saturated aq. NaHCO$_3$ (10 mL) was then added to the reaction mixture with vigorous stirring. The ether layer was separated, dried (MgSO$_4$) and concentrated in vacuo for 12 hr. The crude product was then dissolved in CH$_3$CN (10 mL) at 0° C. and SELECTFLOUR (708 mg, 2 mmol) was added. The reaction mixture was allowed stirred at RT for 12 hr. and poured in to EtOAc (20 mL). The resulting mixture was then washed with brine (3×10 mL), dried (MgSO$_4$) and concentrated in vacuo to obtain viscous oil which was chromatographed on silica (hexane:ethyl acetate 90:10).

[2,6-Dichloro-4-(trifluoromethyl)phenyl]-5-fluoro-5,6-dihydro-2H-cyclopenta[c]pyrazol-4-one (54)

The title compound was synthesized using cyclopentane (48) as the starting ketone: yield 4% overall. $^1$H NMR (CDCl$_3$); δ 8.3 (s, 1H), 8.15 (s, 2H), 5.34 (ddd, 1H, J$_1$=48.7, J$_2$=7.5 and J$_3$=4) 3.7 and 3. 1 (m, 1H each,); MS (M$^+$) 353.4.

2-[2,6-Dichloro-4-(trifluoromethyl)phenyl]-5-fluoro-4,5-dihydro-2H-cyclopenta[c]pyrazol-6-one (58)

The title compound was synthesized using cyclopentane (49) as the starting ketone: yield 18% overall. $^1$H NMR (CDCl$_3$); δ 7.7 (s, 1H,), 7.45 (s, 1H), 5.34 (ddd, 1H, J$_1$=48.7, J$_2$=7.5 and J$_3$=4 Hz) 3.6 and 3.0 (m, 1H each,); MS (M$^+$) 353.

EXAMPLES 38–42

General Procedure for the Preparation of (53), (56), and (61)

To an appropriate ketone (51), (54), or (58) (0.34 mmol) in CH$_2$Cl$_2$ (2 mL) under N$_2$, ethanedithiol (0.03 mL, 0.34 mmol) was added followed BF$_3$xOEt (0.11 mL). The resulting mixture was stirred for 12 hr. and 10% NaHCO$_3$ (aq.) was added. The organic phase was separated dried (MgSO$_4$) and concentrated to obtain corresponding ditholanes (52), (55), or (59).

A solution of N-iodosuccinimide (NIS) (293 mg, 1.3 mmol) CH$_2$Cl$_2$ (2.5 mL) was cooled to –30° C. under N$_2$ and pyridinium poly(hydrogen fluoride) (PPHF) (0.16 mL) was added followed by appropriate crude dithiolanes (52) or (55) in CH$_2$Cl$_2$ (0.5 mL). The resulting mixture was stirred at –30° C. for 30 min. and diluted with CH$_2$Cl$_2$ (10 mL). The reaction mixture was then passed through a pad of basic alumina and washed with 2% Na$_2$S$_2$O$_3$ solution. The organic phase was concentrated and the product was purified by flash chromatography on silica.

2-[2,6-Dichloro-4-(trifluoromethyl)phenyl]-4,4,6,6-tetrafluoro-2,4,5,6-tetrahydrocyclopenta[c]pyrazole (53)

The title compound was synthesized using cyclopenane (51) as the starting ketone: yield 64% overal. $^1$H NMR (CDCl$_3$); δ 7.85 (s, 2H), 7.72 (s, 1H), 3.4 (m, 2H), 3.09; MS (M$^+$+1) 394.

2-[2,6-Dichloro-4-(trifluoromethyl)phenyl]-4,4,5-trifluoro-2,4,5,6-tetrahydrocyclopenta[c]pyrazole (56)

The title compound was synthesized using cyclopentane (54) as the starting ketone: yield 38% overall. $^1$H NMR (CDCl$_3$); δ 7.7 (s, 1H,), 7.6 (s, 1H), 5.4 (dm, 1H, J$_1$=46,) 3.6 and 3.2 (1H each, m); MS (M$^+$) 375.6.

2-[2,6-Dichloro-4-(trifluoromethyl)phenyl]-4,4-difluoro-2,4,5,6-tetrahydrocyclopenta[c]pyrazole (63)

The title compound was synthesized using cyclopentane (48) as the starting ketone: yield 41% overall. $^1$H NMR (CDCl$_3$) δ 7.7 (1H, s), 7.55 (s, 1H), 2.6 (m, 4H,); MS (M$^+$) 357.5.

EXAMPLES 43–45

General Procedure for the Preparation of (57), (73) and (77)

To a solution of appropriate ketone (54), (48) or (51) (1 mmol) in ether (5 mL) under N$_2$, an appropriate Grignard reagent was added at 0° C. The progress of the reaction was monitored by TLC and when the reaction was completed the reaction mixture was poured into a mixture of ether (10 mL) and saturated aq. NH$_4$Cl solution (20 mL) at 0° C. The ether layer was separated, dried (MgSO$_4$) and concentrated in vacuo to obtain the corresponding tertiary alcohols.

2-[2,6-Dichloro-4-(trifluoromethyl)phenyl]-5-fluoro-4-methyl-2,4,5,6-tetrahydrocyclopenta[c]pyrazol-4-ol (57).

The title compound was synthesized using cyclopentane (54) as the starting ketone: yield 80%. $^1$H NMR (CDCl$_3$); δ 7.76 (s, 2H), 7.35 (s, 1H), 5.1 (dm, 1H, J=42), 3.10 (m, 2H), 1.6 (s, 3H); MS (M$^+$+1) 387.4.

2-[2,6-Dichloro-4-(trifluoromethyl)phenyl]-4-methyl-2,4,5,6-tetrahydrocyclopenta[c]pyrazol-4-ol (73)

The title compound was synthesized using cyclopentane (48) as the starting ketone: yield 63%. $^1$H NMR (CDCl$_3$); δ 7.7 (s, 2H), 7.25 (s, 1H), 3.95 (m, 1H), 2.76 (m, 1H), 2.4 (m, 2H); MS (M$^+$) 351.5.

2-[2,6-Dichloro-4-(trifluoromethyl)phenyl]-6,6-difluoro-4-methyl-2,4,5,6-tetrahydrocyclopenta[c]pyrazol-4-ol (77)

The title compound was synthesized using cyclopentane (51) as the starting ketone: yield 70%: $^1$H NMR (CDCl$_3$); δ 7.76 (s, 2H), 7.48 (s, 1H), 3.10 (t, 2H, J=12), 2.76 (s, 3H); MS (M$^+$) 369.4.

EXAMPLES 46 and 47

Preparation of (62) and (75)

To a solution of appropriate ketones (48) or (51) (1.02 mmol) in 10 mL of methanol, sodium borohydride (38.7 mg, 1.02 mmol) was added. The reaction mixture was allowed to stir at ambient temperature. After 1 hour, water (1 mL) was added and the solution was kept stirring for 10 minutes. The solvent was evaporated in vacuo. The residue was dissolved in 50 mL of ethyl acetate and washed with saturated aq. NaHCO$_3$ (50 mL×2) and brine (50 mL×1). The organic layer was dried (MgSO$_4$) and concentrated in vacuo. The residue was purified on silica (hexane-ethyl acetate, 3:1).

2-[2,6-Dichloro-4-(trifluoromethyl)phenyl]-2,4,5,6-tetrahydrocyclopenta[c]pyrazol-4-ol (62)

The title compound was synthesized using cyclopentane (48) as the starting ketone: yield 95%. $^1$H NMR (CDCl$_3$); δ 7.70 (s, 2H), 7.35 (s, 1H), 5.25 (b, 1H), 3.06 (m, 1H), 2.85–2.65 (m, 2H), 2.38 (m, 1H); MS (M$^+$+1) 337.3.

2-[2,6-Dichloro-4-(trifluoromethyl)phenyl]-6,6-difluoro-2,4,5,6-tetrahydrocyclopenta[c]pyrazol-4-ol (75)

The title compound was synthesized using cyclopentane (51) as the starting ketone: yield 91%. $^1$H NMR (CDCl$_3$); δ 7.77 (s, 2H), 7.54 (s, 1H), 5.40 (b, 1H), 3.40 (m, 1H), 2.89 (m, 1H); MS (M$^+$+1) 373.4.

EXAMPLE 48

2-[2,6-Dichloro-4-(trifluoromethyl)phenyl]-4-chloro-2,4,5,6-tetrahydrocyclopenta[c]pyrazole (64)

Thionyl chloride (0.1 mL, 1.37 mmol) was added to a solution of (62) (100.0 mg, 0.29 mmol) in THF (2 mL). After stirring for 2 hours at ambient temperature, EtOAc (10 mL) was added and the resulting mixture was poured into 5% aq. NaHCO$_3$ (20 mL) at 4° C. The resulting mixture was extracted with EtOAc (10 mL). The organic layer was washed with 5% NaHCO$_3$ (20 mL) at 4° C., dried (Na$_2$SO$_4$) and concentrated in vacuo to give the title compound as a pale solid in quantitative yield. $^1$H NMR (CDCl$_3$); δ 7.72 (s, 2H), 7.42 (s, 1H), 5.43 (d, 1H, J=5.6), 3.22–2.94 (m, 2H), 2.85–2.70 (m, 2H); MS (M$^+$+1) 355.4.

EXAMPLE 49

2-[2,6-Dichloro-4-(trifluoromethyl)phenyl]-6-hydrocyclopenta[1,2-c]pyrazole (63)

A solution of (62) (71.0 mg, 0.20 mmol) in DMF (2 mL) was treated with potassium t-butoxide (22.4 mg, 0.20 mmol). After stirring at ambient temperature for 8 hours, the solvent was removed. The residue was dissolved in EtOAc (10 mL) and washed with 5% NaHCO$_3$ (25 mL×2). Dried (Na$_2$SO$_4$) and concentrated in vacuo. The residue was obtained by chromatography on silica (hexane-ethyl acetate, 8:1). Yield 90%: $^1$H NMR (CDCl$_3$); δ 7.74 (s, 2H), 7.30 (s, 1H), 6.68 (d, 1H, J=6.0), 6.38 (d, 1H, J=6.0), 3.37 (s, 2H); MS (M$^+$+1) 319.4.

EXAMPLES 50 and 51

Preparation of (71) and (76)

To a solution of appropriate alcohol (0.134 mmol) in THF (2 mL), potassium t-butoxide (15.0 mg, 0.134 mmol) was added at 0° C. After 10 minutes, the reaction mixture was treated with MeI (28.5 mg, 0.201 mmol) and kept stirring at ambient temperature. After 1 hour, the reaction mixture was poured into 25 mL of water and extracted with EtOAc (25 mL×2), dried (Na$_2$SO$_4$) and concentrated in vacuo. The residue was purified on silica (hexane-ethyl acetate, 8:1) to give corresponding methylated products.

2-[2,6-Dichloro-4-(trifluoromethyl)phenyl]-4-methoxy-2,4,5,6-tetrahydrocyclopenta[c]pyrazole (71)

The title compound was synthesized using cyclopentane (62) as the starting alcohol: yield 27%. $^1$H NMR (CDCl$_3$);

δ 7.73 (s, 2H), 7.44 (s, 1H), 4.86 (m, 1H), 3.38 (s, 3H), 3.16–2.96 (m, 1H), 2.87–2.63 (m, 2H), 2.57–2.40 (m, 1H); MS (M$^+$+1) 351.4.

2-[2,6-Dichloro-4-(trifluoromethyl)phenyl]-6,6-difluoro-4-methoxy-2,4,5,6-tetrahydrocyclopenta[c]pyrazole (76)

The title compound was synthesized using cyclopentane (75) as the starting alcohol: yield 26%. $^1$H NMR (CDCl$_3$); δ 7.77 (s, 2H), 7.56 (s, 1H), 4.96 (b, 1H), 3.44 (s, 1H), 3.29 (m, 1H), 2.95 (m, 1H); MS (M$^+$+1) 387.4.

EXAMPLES 52 and 53

Preparation of (65) and (68)

A mixture of (64) (250 mg, 0.703 mmol), appropriate copper thiolate (0.844 mmol) and DMF (5 mL) was allowed to stir at ambient temperature for 4 hours. The solvent was removed and the residue was dissolved in EtOAc (100 mL) and washed with 5% NaHCO$_3$ (100 mL×2). The organic layer was dried (Na$_2$SO$_4$) and concentrated in vacuo. The residue was purified on silica (hexane-ethyl acetate, 8:1) to give the title compounds.

{2-[2,6-Dichloro-4-(trifluoromethyl)phenyl]-2,4,5,6-tetrahydrocyclopenta[c]pyrazol-4-ylthio}trifluoromethane (65)

The title compound was synthesized using copper trifluoromethylthiolate as the starting thiolate: yield 53%. $^1$H NMR (CDCl$_3$); δ 7.74 (s, 2H), 7.35 (s, 1H), 4.82 (m, 1H), 3.03 (m, 2H), 2.92 (m, 1H), 2.63 (m, 1H); MS (M$^+$+1) 421.5.

2-[2,6-Dichloro-4-(trifluoromethyl)phenyl]-4-methylthio-2,4,5,6-tetrahydrocyclopenta[c]pyrazole (68)

The title compound was synthesized using copper methylthiolate as the starting thiolate: yield 30%. $^1$H NMR (CDCl$_3$); δ 7.70 (s, 2H), 7.30 (s, 1H), 4.29 (m, 1H), 2.98 (m, 2H), 2.85 (m, 1H), 2.45 (m, 1H); MS (M$^+$+1) 367.4.

EXAMPLES 54–57

Preparation of (66), (67), (69) and (70)

A mixture of appropriate sulfide (65) or (68) (0.05 mmol), 3-chloroperoxybenzoic acid (17.2 mg, 0.10 mmol) and CH$_2$Cl$_2$ (3 mL) was allowed to stir at ambient temperature. After 8 hours, the reaction mixture was diluted with CH$_2$Cl$_2$ (25 mL) and washed with 5% NaHCO$_3$ (30 mL×2). The organic layer was dried (Na$_2$SO$_4$) and concentrated in vacuo. The residue was purified on silica (hexane-ethyl acetate, 8:1) to give title compounds.

({2-[2,6-Dichloro-4-(trifluoromethyl)phenyl](2,4,5,6-tetrahydrocyclopenta[c]pyrazol-4-yl)}sulfinyl)trifluoromethane (66)

The title compound was synthesized using cyclopentane (65) as the starting sulfide: yield 64%. $^1$H NMR (CDCl$_3$); δ 7.74 (s, 2H), 7.56 and 7.40 (s, 1H), 4.86 and 4.65 (m, 1H), 3.30–2.60 (m, 4H); MS (M$^+$+1) 437.1.

({2-[2,6-Dichloro-4-(trifluoromethyl)phenyl]-2,4,5,6-tetrahydrocyclopenta[c]pyrazol-4-yl)}sulfonyl)trifluoromethane (67)

The title compound was synthesized using cyclopentane (66) as the starting sulfoxide: yield (18%). $^1$H NMR (CDCl$_3$); δ 7.76 (s, 2H), 7.56 (s, 1H), 4.88 (d, 1H, J=7.8), 3.20–2.88 (m, 4H); MS (M$^+$+1) 453.1.

2-[2,6-Dichloro-4-(tifluoromethyl)phenyl]-4-methylsulfinyl-2,4,5,6-tetrahydrocyclopenta[c]pyrazole (69)

The title compound was synthesized using cyclopentane (70) as the starting sulfide: yield (70%). $^1$H NMR (CDCl$_3$); δ 7.68 (s, 2H), 7.43 and 7.41 (s, 1H), 4.27 (m, 1H), 2.9 (m, 4H), 2.68 and 2.33 (s, 3H); MS (M$^+$) 383.

2-[2,6-Dichloro-4-(trifluoromethyl)phenyl]-4-methylsulfonyl-2,4,5,6-tetrahydrocyclopenta[c]pyrazole (70)

The title compound was synthesized using cyclopentane (71) was the starting sulfoxide: yield (37%). $^1$H NMR (CDCl$_3$); δ 7.69 (s, 2H), 7.5 (s, 1H), 4.5 (m, 1H), 3.0 (m, 4H), 2.7 (s, 3H); MS (M$^+$) 399.

EXAMPLE 58 cis-2-[2,6-Dichloro-4-(trifluoromethyl)phenyl]-2,4,5,6-tetrahydrocyclopenta[c]pyrazole-5,6-diol (80)

A solution of 79 (20.0 mg, 62 μmol) in 0.15 mL of t-BuOH and 0.3 mL of water was added 1.96% w/w OsO$_4$ solution in t-BuOH (186 μL, 11 μmol). 4-methylmorpholine N-oxide (8.4 mg, 62 μmol) was added to the mixture. The mixture was stirred at room temperature for 12 h. Then mixture was poured into NaHCO$_3$ solution (5 mL) and extracted with CH$_2$Cl$_2$ (5 mL×3). The organic layers were combined and dried. The solvent was then removed under reduced pressure. The product purified using PTLC (hexane:ethyl acetate 1:1). Yield 50%: $^1$H NMR (CDCl$_3$); δ 7.70 (s, 2H), 7.21 (s, 1H), 5.05 (t, 1H, J=4.58), 4.73 (quintet, 1H, J=6.14), 3.12 (dd, 1H, J$_1$=15.2 , J$_2$=6.6), 2.97 (d, 1H, J=7.51 Hz), 2.76 (dd, 1H, J$_1$=15.2 , J$_2$=6.6), 2.66 (d, 1H, J=4.66 ); MS (M$^+$) 353.5.

EXAMPLE 59 cis-2-[2,6-Dichloro-4-(trifluoromethyl)phenyl]-5,6-difluoro-2,4,5,6-tetrahydrocyclopenta[c]pyrazole (81)

A solution of 80 (9.6 mg, 27.2 μmol) in 500 μL of 1,2-dichloroethane was added diethylaminosulfur trifluoride (DAST) (14 μL, 109 μmol). The mixture was stirred at room temperature for 12 h. The product was purified using preparative TLC (hexane:ethyl acetate 3:1). Yield 58%: $^1$H NMR (CDCl$_3$) δ 7.72 (s, 2H), 7.31 (d, 1H), 5.81 76 (dd, 1H, J$_1$=57.3, J$_2$=4.4), 5.36 (md, 1H, J=48.59), 3.27 (ddd, 1H, J$_1$=14.8, J$_2$=7.01, J$_3$=3.7), 3.15 (dt, 1H, J=6.96, 14.8); MS (M$^+$) 357.3.

EXAMPLE 60

3-[2,6-Dichloro-4-(trifluoromethyl)phenyl]-5,1a,5a-trihydro-1aH,5aH-pyrazolo[4',3'-2,1]cyclopenta[3,4-b]oxirane (82)

A solution of 79 (17.6 mg, 54.5 μmol) in DCE (1 mL) was added 3-chloroperoxybenzoic acid (50%, 28 mg, 81.8 μmol). The resulting mixture was stirred at room temperature for 12 h. The product was then purified using preparative TLC (PTLC). (hexane/ethyl acetate 3:1). Yield 52%: $^1$H NMR (CDCl$_3$) δ 7.69 (s, 2H), 7.17 (s, 1H), 4.29 (t, 1H, J=2.61), 4.27 (d, 1H, J=2.39), 3.08 (d, 1H, J=17.2), 2.85 (dd, 1H, J$_1$=17.2, J$_2$=1.9); MS (M$^+$) 335.5.

EXAMPLE 61

2-[2,6-Dichloro-4-(trifluoromethyl)phenyl]-6-fluoro-2,4,5,6-tetrahydrocyclopenta[c]pyrazol-5-ol (83)

A solution of 82 (9.9 mg, 29.5 μmol) in 1,2-dichloroethane (μL) was added 20 μL of 50% pyridinium poly(hydrogen fluoride) (PPHF) (20 μL). The mixture was stirred at room temperature for 12 h and poured into saturated NaHCO$_3$ solution (5 mL) and extracted with CH$_2$Cl$_2$ (5 mL×3). The organic layers were combined and dried (Na$_2$SO$_4$) and concentrated in vacuo. The product was then purified using PTLC (hexane:ethyl acetate 1:1). Yield 51%: $^1$H NMR (CDCl$_3$) δ 7.72 (s, 2H), 7.27 (s, 1H), 5.69 (dd, 1H, J$_1$=58.2, J$_2$=4.6), 4.71 (br d, 1H, J=18.51), 3.23 (dd, 1H, J$_1$=15, J$_2$=7.2), 2.78 (dd, 1H, J$_1$=15, J$_2$=7.2), 2.65 (br s, 1H); MS (M$^+$) 355.4.

EXAMPLE 62

2-[2,6-Dichloro-4-(trifluoromethyl)phenyl]-2,4,5,6-tetrahydrocyclopenta[c]pyrazole-5,6-diol (84) and 2-[2,6-Dichloro-4-(trifluoromethyl)phenyl]-2,4,5,6-tetrahydrocyclopenta[c]pyrazole-4,5-diol (85)

To a solution of (62) (5 g) in Benzene (50 mL) p-TSA (500 mg) was added and the resulting mixture was heated at reflux for 6 hr. while water formed in the reaction was removed using a Dean-Stark Trap. The reaction mixture was allowed to cool down to room temperature and washed with water (5×50 mL). The organic layer was concentrated in vacuo to obtain an oil which was dried on a high vacuum and directly used in next step. To a solution of above product (4.8 g) in 1:1 t-BuOH/H$_2$O (100 mL) was treated with NMO (3 g) and OsO$_4$ (380 mg). The resulting mixture was stirred at RT for 12 hr. Aq. NaHCO$_3$ (300 mL) and EtOAc (300 mL) were then added, and the product was extracted in to EtOAc. Organic phase was separated, and the concentrated in vacuo to obtain compounds (80) and (84) which were separated on silica (EtOAc:Hexane 2:3).

(80): yield 26.9% overall; $^1$H NMR (400 MHz, CDCl$_3$) δ 7.68 (s, 2H), 7.18 (s, 1H), 5.00 (m, 1H), 4.6 (m, 1H,), 3.5 (m, 1H), 3.15 (m, 2H), 2.7 (dd, 1H, J=4.46, 16 Hz).

(84); Yield 15.3% overall; $^1$H NMR (400 MHz, CDCl$_3$) δ 7.68 (s, 2H), 7.43 (s, 1H), 5.00 (t, 1H, J=8 Hz), 4.72 (m, 1H,), 3.15 (dd, 1H, J=J=4.5, 15.8, 1H), 2.8 (dd, 1H, J=4.5, 15.8 Hz), 2.75 (d, 1H J=8 Hz), 2.31 (d, 1H, j=8 Hz).

EXAMPLE 63

2-[2,6-Dichloro-4-(trifluoromethyl)phenyl]-5,6-difluoro-2,4,5,6-tetrahydrocyclopenta[c]pyrazole (86)

To a solution of (80) (9.6 mg, 27.2 mmol) in 500 mL of 1,2-dichloroethane was added DAST (14 mL, 109 mmol). The mixture was stirred at room temperature for 12 h. The mixture was then chromatographed on a silica gel TLC plate using hexane/ethyl acetate (3:1): yield 58%: $^1$H NMR (400 MHz, CDCl$_3$) δ 7.72 (s, 2H), 7.31 (s, 1H), 5.81 (dd, 1H, J=4.46, 57.36 Hz), 5.36 (md, 1H, J=48.59 Hz), 3.27 (ddd, 1H, J=3.77, 7.01, 14.86 Hz), 3.15 (dt, 1H, J=6.96, 14.86 Hz); MS (M$^+$) 357.3.

EXAMPLE 64

2-[2,6-Dichloro-4-(trifluoromethyl)phenyl]-5,6-difluoro-5,6-dihydrocyclopenta[c]pyrazol-4-one (87)

To a solution of (86) (20.2 mg, 56.6 mmol) in 500 mL acetic acid was added chromium(VI) oxide (30 mg, 283 mmol). The mixture was stirred at 50° C. for 12 h. The solvent was removed under reduced pressure. The mixture was then chromatographed on a silica gel TLC plate using hexane/ethyl acetate (9:1) to give (87): Yield 76%): $^1$H NMR (400 MHz, CDCl$_3$) δ 7.97 (s, 1H), 7.81 (s, 2H), 6.23 (dd, 1H, J=4.97, 55.81 Hz), 5.37 (ddd, 1H, J=4.97, 12.36, 47.15 Hz).

EXAMPLE 65

2-[2,6-Dichloro-4-(trifluoromethyl)phenyl]-5,6-difluoro-4-methyl-2,4,5,6-tetrahydrocyclopenta[c]pyrazol-4-ol (88)

To a solution of (87) (6.6 mg, 17.8 mmol) in 500 mL THF was added methyl magnesium bromide (10 mL, 3.0 M). The mixture was stirred at room temperature for 3 h. The mixture was poured into 5 mL dilute NaHCO$_3$ solution. The aqueous solution was extracted with dichloromethane (5 mL×3). The organic layers were combined, washed with brine and dried with anhydrous sodium sulfate. The mixture was then chromatographed on a silica gel TLC plate using dichloromethane/ethyl acetate (9:1) to give (88): yield (32%): $^1$H NMR (400 MHz, CDCl$_3$) δ 7.75 (s, 2H), 7.57 (s, 1H), 5.89 (dd, 1H, J=4.25, 56.66 Hz), 4.92 (ddd, 1H, J=4.25, 15.76, 48.17 Hz), 2.47 (br s, 1H), 1.75 (s, 3H).

EXAMPLE 66

2-[2,6-Dichloro-4-(trifluoromethyl)phenyl]-4,4,5,6-tetrafluoro-2,4,5,6-tetrahydrocyclopenta[c]pyrazole (89)

To a solution of (87) (14.8 mg, 40 mmol) in 1 mL dichloromethane under nitrogen was added 1,2-ethanedithiol (3.8 mg, 40 mmol) and 13 mL of boron trifluoride diethyl etherate. The mixture was stirred at room temperature for 12 h. The mixture was poured into 5 mL dilute NaHCO$_3$ solution. The aqueous solution was extracted with dichloromethane (5 mL×3). The organic layers were combined, washed with brine, and dried with anhydrous sodium sulfate. The mixture was then chromatographed on a silica gel TLC plate using hexane/ethyl acetate (3:1) to give corresponding dithiolane: yield 91%: $^1$H NMR (400 MHz, CDCl$_3$) δ 7.74 (s, 2H), 7.57 (s, 1H), 5.90 (dd, 1H, J=4.21, 56.51 Hz), 4.28 (ddd. 1H, J=4.21, 14.95, 48.56 Hz), 2.62 (m, 4H).

A solution of above dithiolane (16.2 mg, 36.2 mmol) in 1 mL of dichloromethane was added to a solution of N-iodosuccinimide (33 mg, 145 mmol) and 50 mL of hydrogen fluoride-pyridine in 2 mL dichloromethane at −30° C. The reaction was stirred at the same temperature for 30 min. The mixture was poured into 5 mL saturated NaHCO$_3$ solution. The aqueous solution was extracted with dichloromethane (5 mL×3). The organic layers were combined, washed with brine and dried with anhydrous sodium sulfate. The mixture was then chromatographed on a silica gel TLC plate using hexanes/ethyl acetate (3:1) to give (89): yield (80%): $^1$H NMR (400 MHz, CDCl$_3$) δ 7.78 (br s, 3H), 6.01 (td, 1H, J=3.80, 55.68 Hz), 5.30 (dm, 1H, J=49.18 Hz).

EXAMPLE 67

2-[2,6-Dichloro-4-(trifluoromethyl)phenyl]-4,6-dihydrocyclopenta[c]pyrazol-5-one (85)

A solution of (84) (353 mg, 1 mmol) in benzene (5 mL) and p-TSA (35 mg) was heated at reflux for 15 min. The reaction mixture was allowed to cool to room temperature and washed with water (5×5 mL). The organic layer was separated and concentrated to obtain a viscous oil which was then chromatographed on a silica gel TLC plate using hexane/ethyl acetate (3:1) to give (85): yield 65%: $^1$H NMR (400 MHz, CDCl$_3$) δ 7.74 (s, 2H), 7.38 (s, 1H), 3.54 (s, 2H), 3.49 (s, 2H).

EXAMPLE 68

2-[2,6-Dichloro-4-(trifluoromethyl)phenyl]-5,5-difluoro-2,4,5,6-tetrahydrocyclopenta[c]pyrazole (90)

To a solution of (85) (13 mg, 38.3 mmol) in 1 mL of 1,2-dichloroethane was added DAST (40 mL, 31 mmol). The reaction mixture was stirred at 50° C. for 12 h. The mixture was then chromatographed on a silica gel TLC plate using hexane/ethyl acetate (9:1) to give (90): yield 46%: $^1$H NMR (400 MHz, CDCl$_3$) δ 7.74 (s, 1H), 7.72 (s, 1H), 7.28 (s, 1H), 3.43 (t, 2H, J=13.77 Hz), 3.34 (t, 2H, J=13.77 Hz).

EXAMPLE 69

2-[2,6-Dichloro-4-(trifluoromethyl)phenyl]-5,5-difluoro-5,6-dihydrocyclopenta[c]pyrazol-4-one (91)

To a solution of (90) (36.7 mg, 103 mmol) in 1 mL acetic acid was added chromium(VI) oxide (31 mg, 308 mmol). The mixture was stirred at 50° C. for 12 h. The mixture was then chromatographed on a silica gel TLC plate using hexane/ethyl acetate (9:1) to give (91): yield 50%: $^1$H NMR (400 MHz, CDCl$_3$) δ 8.01 (s, 1H), 7.80 (s, 2H), 3.63 (t, 2H, J=11.77 Hz).

EXAMPLE 70

2-[2,6-Dichloro-4-(trifluoromethyl)phenyl]-5,5-difluoro-4-methyl-2,4,5,6-tetrahydrocyclopenta[c]pyrazol-4-ol (93)

To a solution of (91) (3.6 mg, 9.7 mmol) in 300 mL THF was added methyl magnesium bromide (50 mL, 3.0 M) at 0° C. The solution was then stirred at room temperature for 30 min. The mixture was poured into 5 mL of saturated NaHCO$_3$ solution and extracted with dichlormethane (5 mL×3). The organic layers were combined, washed with brine, and dried with anhydrous sodium sulfate. The mixture was then chromatographed on a silica gel TLC plate using hexane/ethyl acetate (3:1) to give (93): yield 98%: $^1$H NMR (400 MHz, CDCl$_3$) δ 7.73 (s, 2H), 7.47 (s, 1H), 3.65–3.31 (m, 2H), 2.46 (br s, 1H), 1.67 (s, 3H).

EXAMPLE 71

2-[2,6-Dichloro-4-(trifluoromethyl)phenyl]-4,4,5,5-tetrafluoro-2,4,5,6-tetrahydrocyclopenta[c]pyrazole (92)

A solution of (91) (14.7 mg, 39.6 mmol) in 1 mL dichloromethane under nitrogen was added 1,2-ethanedithiol (3.3 mg, 39.6 mmol) and 13 mL of boron trifluoride diethyl etherate. The mixture was stirred at room temperature for 12 h. The mixture was poured into 5 mL dilute NaHCO$_3$ solution. The aqueous solution was extracted with dichloromethane (5 mL×3). The organic layers were combined, washed with brine, and dried with anhydrous sodium sulfate. The mixture was then chromatographed on a silica gel TLC plate using hexanes/ethyl acetate (3:1) to give corresponding dithiolane: yield 87%; $^1$H NMR (400 MHz, CDCl$_3$) δ 7.72 (s, 2H), 7.49 (s, 1H), 3.48 (m, 6H).

A solution of the above dithiolane (15.4 mg, 34.4 mmol) in 1 mL of dichloromethane was added to a solution of N-iodosuccinimide (31 mg, 138 mmol) and 50 mL of hydrogen fluoride-pyridine in 1.5 mL dichloromethane at −30° C. The reaction was stirred at that temperature for 30 min. The mixture was poured into 5 mL saturated NaHCO$_3$ solution. The aqueous solution was extracted with dichloromethane (5 mL×3). The organic layers were combined, washed with brine, and dried with anhydrous sodium sulfate. The mixture was then chromatographed on a silica gel TLC plate using hexanes/ethyl acetate (9:1) to give (92): yield 54%; $^1$H NMR (400 MHz, CDCl$_3$) δ 7.77 (s, 2H), 7.74 (t, 1H, J=1.60 Hz), 3.56 (t, 2H, J=11.70 Hz).

EXAMPLE 72

In Vitro Assay to Screen Compounds for Ability to Bind Housefly GABA Receptors

Housefly neuronal membranes were prepared as described above from housefly heads. Test compounds were dissolved in dimethylsulfoxide (DMSO) at concentrations ranging from about 2 nM to about 100 mM. About 1 μL of a dissolved test compound was dispensed into a well of a 96-well polystyrene plate. About 100 μL of ice cold assay buffer (10 mM phosphate, 300 mM NaCl, pH 7.5) containing 5.2 nM 4'-Ethynyl-4-n-[2,3-$^3$H$_2$]propylbicycloorthobenzoate ($^3$H-EBOB, 38 Ci/mmol, available from NEN Life Science Products, Boston, Mass.) was added to the well, followed by about 100 μL of ice cold assay buffer containing about 0.5–1.0 mg/mL housefly neuronal membranes. Control wells were prepared the same way except that the housefly neuronal membranes were omitted from the "negative" wells, and the test compounds were omitted from the "positive" wells. The samples were incubated for about 45 min at about 24° C. and then filtered on a 0.1% (w/v) polyethylenimine-soaked glass fiber Filtermat A (available from EG&G Wallac Inc., Gaithersburg, Md.) followed by four 100 mL rinses of cold assay buffer using a Harvester 96® cell harvester (available from Tomtec, Orange, Conn.). The filtermat was air dried and radioactivity bound to the filtermat was detected with either a 1450 MicroBeta® Trilux scintillation counter (available from EG&G Wallac Inc.) or a Topcount NXT™ scintillation counter (available from Packard Instrument Co., Meriden, Conn.) using standard methods.

Specific binding was considered to be the difference between total $^3$H bound to the neuronal membranes in the absence of any inhibitors and nonspecific $^3$H bound to the neuronal membranes upon the addition of 5 μM unlabeled EBOB. The average radioactivity contained in the "negative" wells was subtracted from each of the assay wells. The results indicated that about 60–90% of the $^3$H-EBOB bound to the housefly neuronal membranes in the absence of inhibitors was specifically bound. Compounds that displaced $^3$H-EBOB at a level equivalent to 5 μM unlabeled EBOB were said to display "100% inhibition" of $^3$H-EBOB binding, while compounds that did not displace $^3$H-EBOB at all were said to display "0% inhibition" of $^3$H-EBOB binding. Compounds that displaced $^3$H-EBOB specifically bound to the housefly neuronal membranes were tested at 24–48 different final concentrations, varying from about 0.1 nM to about 125 μM, in order to determine the concentration at which 50% of the maximum inhibition due to the addition of that compound was observed (IC$_{50}$). This value was calculated by plotting the data on a log-linear plot and either dropping a line to the x-axis perpendicular to a line drawn to the y-axis at approximately 50% inhibition of $^3$H-EBOB binding, or by fitting the data to the formula I=XY/(X+Z), in which I is the percent inhibition of $^3$H-EBOB binding, X is the inhibitor concentration, Y is the maximum percent inhibition of $^3$H-EBOB binding observed, and Z is the calculated IC$_{50}$.

The results indicated that several of the compounds tested had IC$_{50}$ values ranging from about 10 nM to about 100 µM. Compounds with the most activity are (1), (3), (10), (11), (12), (13), (15), (22), (35), (38) and (42).

EXAMPLE 73

In Vitro Assay to Screen Compounds for Their Ability to Bind Mouse Brain GABA Receptors Mouse brain membranes were prepared as described above from dissected mouse brains. Test compounds were dissolved in dimethylsulfoxide (DMSO) at concentrations ranging from about 2 nM to about 100 mM. About 1 µL of a dissolved test compound was dispensed into a well of a 96-well polystyrene plate. About 100 µL of ice cold assay buffer (10 mM phosphate, 300 mM NaCl, pH 7.5) containing 5.2 nM 4'-Ethynyl-4-n-[2,3-$^3$H$_2$] propylbicycloorthobenzoate ($^3$H-EBOB, 38 Ci/mmol, available from NEN Life Science Products, Boston, Mass.) was added to the well, followed by about 100 µL of ice cold assay buffer containing about 0.25–0.5 mg/mL mouse brain membranes. Control wells were prepared the same way except that the mouse brain membranes were omitted from the "negative" wells, and the test compounds were omitted from the "positive" wells. The samples were incubated for about 45 min at about 24° C. and then filtered on a 0.1% (w/v) polyethylenimine-soaked glass fiber Filtermat A (available from EG&G Wallac Inc., Gaithersburg, Md.) followed by four 100 mL rinses of cold assay buffer using a Harvester 96® cell harvester (available from Tomtec, Orange, Conn.). The filtermat was air dried and radioactivity bound to the filtermat was detected with either a 1450 MicroBeta® Trilux scintillation counter (available from EG&G Wallac Inc.) or a Topcount NXT™ scintillation counter (available from Packard Instrument Co., Meriden, Conn.) using standard methods.

Specific binding was considered to be the difference between total $^3$H bound to the mouse brain membranes in the absence of any inhibitors and nonspecific $^3$H bound to the mouse brain membranes upon the addition of 5 µM unlabeled EBOB. The average radioactivity contained in the "negative" wells was subtracted from each of the assay wells. The results indicated that about 80–95% of the $^3$H-EBOB bound to the mouse brain membranes in the absence of inhibitors was specifically bound. Compounds that displaced $^3$H-EBOB at a level equivalent to 5 µM unlabeled EBOB were said to display "100% inhibition" of $^3$H-EBOB binding, while compounds that did not displace $^3$H-EBOB at all were said to display "0% inhibition" of $^3$H-EBOB binding. Compounds that displaced $^3$H-EBOB specifically bound to the mouse brain membranes were tested at 24–48 different final concentrations, varying from about 1 nM to about 125 µM, in order to determine the concentration at which 50% of the maximum inhibition due to the addition of that compound was observed (IC$_{50}$). This value was calculated by plotting the data on a log-linear plot and either dropping a line to the x-axis perpendicular to a line drawn to the y-axis at approximately 50% inhibition of $^3$H-EBOB binding, or by fitting the data to the formula I=XY/(X+Z), in which I is the percent inhibition of $^3$H-EBOB binding, X is the inhibitor concentration, Y is the maximum percent inhibition of $^3$H-EBOB binding observed, and Z is the calculated IC$_{50}$.

As reported in Table 2, the results indicated that several of the compounds tested had IC$_{50}$ values ranging from about 1 µM to about 100 µM.

TABLE 2

| | In Vitro Binding Assay | |
|---|---|---|
| Compound No.* | IC$_{50}$ (nM), Fly Head | IC$_{50}$ (nM), Mouse Brain |
| 1 | 530 | 1 × 10$^6$ |
| (±); (+); or (−)-1' | 950 | 1 × 10$^6$ |
| 2 | 4000 | 1 × 10$^6$ |
| 2" | 1000 | 1 × 10$^6$ |
| 3 | 90 | 2000 |
| 6 | 1100 | 730 |
| 10 | 350 | 3800 |
| 11 | 83 | 1600 |
| 12 | 1000 | 3 × 10$^4$ |
| 13 | 30 | 1 × 10$^6$ |
| 15 | 22 | 3 × 10$^4$ |
| 16 | 3000 | 1 × 10$^6$ |
| 49 | 530 | 1 × 10$^6$ |
| 56 | <100 | 1000 |
| 57 | 140 | 2.5 × 10$^4$ |
| 61 | <100 | 1000 |
| 63 | 400 | 1000 |
| 67 | 32 | 2.5 × 10$^4$ |
| 68 | 10 | 1000 |
| 81 | <100 | 1000 |
| 88 | 350 | 1 × 10$^6$ |
| 89 | <<100 | 180 |
| 92 | <<100 | 60 |
| 93 | 100 | 2300 |

*Compound No. refers to the number in Table 1, supra and Schemes 9–13.

EXAMPLE 74

In Vivo Housefly Assay

This example describes an in vivo assay to screen compounds for their ability to kill houseflies via contact. Newly emerged houseflies (*Musca domestica*, available from Rincon-Vitova Insectaries, Inc., Ventura, Calif.) were sedated with carbon dioxide gas, collected in 50 mL polypropylene conical tubes containing filter paper saturated with 10% (w/w) sucrose in water, and allowed to feed at room temperature for about 2–4 hours. Test compounds were dissolved as in dimethylsulfoxide (DMSO) at concentrations ranging from about 0.05 mM to about 100 mM. About 1 µL of dissolved test compound and about 100 µL of isopropanol were dispensed into the bottom of a 9 mL screw-top glass test tube. Positive control test tubes were prepared in the same manner except that no test compounds were dissolved in the DMSO. Each test tube was rolled to coat the sides with the chemical solution, and allowed to air dry 24–48 hours. About 20 houseflies were sedated by refrigeration at 0–4° C. and transferred to each test tube. Each test tube was sealed with organdy cloth secured by an open top screw cap and laid horizontally in the dark. After about 24 hours, the healthy, moribund, and dead houseflies in each test tube were counted. The percentage of dead houseflies in each test tube was then calculated using the formula M=100(D−(FC/100))/(F−(FC/100)), in which M is the percentage of dead houseflies due to the addition of the test compound, D is the number of dead houseflies in the test tube, F is the total number of houseflies in the test tube, and C is the percentage of dead houseflies in the control test tubes.

Compounds of the invention that affected the survival of houseflies preferably cause 20–100% mortality or morbidity at 100 mM. Results for compounds of the invention appear in Table 3, column 2, below.

EXAMPLE 75

In Vivo Cat Flea Assay

This example describes an in vivo assay to screen compounds for their ability to kill cat fleas via contact.

Test compounds were dissolved in dimethylsulfoxide (DMSO) at concentrations ranging from about 0.05 mM to about 100 mM. About 1 μL of dissolved test compound was dispensed onto a 6 mm (diameter) GF/C filter disk (filter material available from Whatman Inc., Clifton, N.J.) in the bottom of a 4 mL screw-top glass vial and allowed to air dry 24–48 hours. Positive control vials were prepared in the same manner except that no test compounds were dissolved in the DMSO. About 20 newly emerged cat fleas (Ctenocephalides felis) were sedated by refrigeration at 0–4° C. and transferred to each vial. Each vial was sealed with a thin, perforated Teflon™ septum secured by an open top screw cap and held vertically in the dark. After about 24–30 hours, the healthy, moribund, and dead cat fleas in each vial were counted. The percentage of dead cat fleas in each vial was then calculated using the formula M=100(D−(FC/100))/(F−(FC/100)), in which M is the percentage of dead cat fleas due to the addition of the test compound, D is the number of dead cat fleas in the test vial, F is the total number of cat fleas in the test vial, and C is the percentage of dead cat fleas in the control vials.

Compounds of the invention that affected the survival of cat fleas preferably cause 20–100% mortality or morbidity at 100 mM. Results for compounds of the invention appear in Table 3, columns 3 and 4, below.

TABLE 3

| | Contact Assay | | |
| --- | --- | --- | --- |
| Compound No.* | LD$_{50}$ (mM), Flies | LD$_{50}$ (mM), CO Fleas | LD$_{50}$ (mM), NC Fleas |
| 3 | 2.7 | 1.7 | 3.0 |
| (±); (+); or (−)-3' | 2 | >100 | >100 |
| 3" | 5 | >100 | >100 |
| 11 | >100 | 8 | 7 |
| 13 | >100 | 37.5 | 20 |
| 15 | >100 | 29.5 | 33.5 |
| 35 | 48 | 17 | 12 |
| 38 | >100 | 54 | 15 |
| 56 | N.D.** | 1 | N.D. |
| 57 | N.D. | 3.8 | N.D. |
| 61 | N.D. | 5 | N.D. |
| 81 | N.D. | 1.5 | N.D. |
| 88 | N.D. | 5 | N.D. |
| 89 | N.D. | <0.5 | N.D. |
| 92 | N.D. | <0.5 | N.D. |

*Compound No. refers to the number in Table 1, supra and Schemes 9–13.
**N.D. = not determined.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound of Formula I:

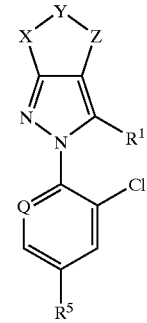

or a salt thereof, wherein
R$^1$ is amino, hydrogen, alkyl, hydroxy, halo, alkoxy, alkylamino, dialkylamino, alkylthio, alkylsulfinyl, alkylsulfonyl, trifluoroalkylsulfinyl, trifluoroalkylsulfonyl, hydroxy, trifluoromethyl, or acetylamino;

X, Y and Z are each independently (CH)$_n$ or (CR$^3$R$^4$)$_n$, wherein n is 1 or 2;

Q is N or C—R$^6$, wherein R$^6$ is fluoro, chloro, bromo, or iodo;

R$^5$ is halo, C$_1$–C$_6$ alkyl, C$_1$–C$_4$ alkenyl, C$_1$–C$_4$ alkoxy, C$_1$–C$_4$ alkylamino, C$_1$–C$_4$ dialkylamino, C$_1$–C$_4$ alkylthio, C$_1$–C$_4$ alkylsulfinyl, C$_1$–C$_4$ alkylsulfonyl, C$_1$–C$_4$ trifluoroalkylsulfinyl, C$_1$–C$_4$ trifluoroalkylsulfonyl, hydroxy, amino, or trifluoromethyl;

R$^3$ and R$^4$ are each independently hydrogen, halo, alkyl, alkenyl, alkynyl, cycloalkyl, cyano, trifluoromethyl, aryl, alkylamino, dialkylamino, alkoxy, cycloalkoxy, trifluoroalkyl, pentafluoroalkyl, perfluoroalkyl, thioalkyl, cycloalkylthio, trifluoroalkylthio, alkylthio, alkylsulfinyl, alkylsulfonyl, amino, or hydroxy, or R$^3$ and R$^4$ taken together are oxo, or R$^3$ and R$^4$ taken together with the carbon to which they are attached form a 3- to 7-membered saturated ring optionally including one or two oxygen or sulfur atoms, said ring being optionally substituted by one to three C$_{1-4}$ alkyl groups;

or vicinal R$^4$ forms an optionally substituted cycloalkyl or aryl ring while R$^3$ is as defined above;

with the proviso that, when X, Y, and Z together form —(CH$_2$)$_3$—, —(CH$_2$)$_4$—, or —(CH$_2$)$_5$— then R$^1$ is not halo or butyl.

2. A compound of claim 1, wherein:
R$^1$ is amino, hydrogen, alkyl, hydroxy, halo, alkoxy, or acetylamino;

Q is C—Cl;

R$^5$ is CF$_3$; and

R$^3$ and R$^4$ are each independently hydrogen, halo, alkyl, alkenyl, alkynyl, cycloalkyl, cyano, trifluoromethyl, aryl, alkoxy, cycloalkoxy, trifluoroalkyl, pentafluoroalkyl, perfluoroalkyl, thioalkyl, cycloalkylthio, trifluoroalkylthio, alkylthio, alkylsulfinyl, alkylsulfonyl or hydroxy, or R$^3$ and R$^4$ taken together are oxo, or R$^3$ and R$^4$ taken together with the carbon to which they are attached form a 3- to 7-membered saturated ring optionally including one or two oxygen or sulfur atoms, said ring being optionally substituted by one to three $C_{1-4}$ alkyl groups;

or vicinal $R^4$ forms an optionally substituted cycloalkyl or aryl ring while $R^3$ is defined as above.

3. The compound of claim 2, wherein $R^1$ is hydrogen, methoxy, methyl, hydroxy, acetylamino, amino, chloro or bromo.

4. The compound of claim 3, wherein $R^1$ is hydrogen.

5. The compound of claim 3, wherein $R^1$ is amino.

6. The compound of claim 2, wherein

X is $CH_2$;

Y is $CH_2$; and

Z is $CH_2$.

7. The compound of claim 2 wherein:

$R^1$ is hydrogen; and $R^3$ and $R^4$ are each independently:

hydrogen; or hydroxy; or fluoro, chloro, bromo or iodo; or $C_1$–$C_6$ alkyl, $C_2$–$C_6$ alkenyl, $C_2$–$C_6$ alkynyl or $C_3$–$C_7$ cycloalkyl; or $C_1$–$C_6$ alkoxy, $C_3$–$C_7$ cycloalkyloxy, trifluoroalkyl, pentafluoroalkyl, or perfluoroalkyl; or $C_1$–$C_6$ thioalkyl, $C_3$–$C_7$ cycloalkylthio, $C_1$–$C_2$ trifluoroalkylthio or $C_1$–$C_6$ alkylthio; or $C_1$–$C_6$ sulfinyl, $C_1$–$C_6$ sulfonyl, $C_{1-2}$ trifluoroalkylsulfinyl, $C_{1-2}$ trifluoroalkylsulfonyl; or $R^3$ and $R^4$ are taken together form oxo.

8. The compound of claim 7 wherein X and Y are $CH_2$, and Z is $CR^3R^4$ wherein $R^3$ is hydrogen and $R^4$ is selected from the group consisting of hydrogen, hydroxy, methoxy, trifluoromethoxy, methylthio, and trifluoromethylthio.

9. The compound of claim 7 wherein X, Y, and Z are $CR^3R^4$ wherein $R^3$ and $R^4$ are independently hydrogen or fluorine.

10. The compound of claim 7 wherein X, Y, and Z are $(CR^3R^4)_n$, wherein $R^3$ and $R^4$ are independently hydrogen, fluoro, hydroxy, $C_1$–$C_6$ alkoxy, $C_1$–$C_6$ alkyl, $C_2$–$C_6$ alkenyl, $C_2$–$C_6$ alkynyl or $C_3$–$C_7$ cycloalkyl; or $R^3$ and $R^4$ are taken together form oxo.

11. The compound of claim 7 wherein X is $CH_2$, Y is $CF_2$, and Z is $CR^3R^4$ wherein $R^3$ is hydrogen and $R^4$ is selected from the group consisting of hydrogen, hydroxy, methoxy, trifluoromethoxy, methylthio, and trifluoromethylthio.

12. The compound of claim 2, wherein:

$R^1$ is hydrogen; and $R_3$ and $R_4$ are each independently hydrogen, fluoro, hydroxy, $C_1$–$C_6$ alkoxy, $C_1$–$C_6$ alkyl, $C_2$–$C_6$ alkenyl, $C_2$–$C_6$ alkynyl or $C_3$–$C_7$ cycloalkyl; or $R^3$ and $R^4$ are taken together form oxo.

13. A pesticidal composition, comprising:

(a) a pesticidally effective amount of at least one compound of claim 1; and (b) one or more pesticidally-acceptable excipients.

14. The composition of claim 13, useful for oral or topical administration.

15. The composition of claim 14, further comprising at least one additional substance selected from a synergist, stabilizing substance, insecticide, pesticide, acaricide, plant nematocide, anthelmintic, anticoccidial, fungicide, bactericide, antiviral, arthropod attractant, arthropod repellent, arthropod pheromone, vertebrate attractant, vertebrate repellent, vertebrate pheromone, deodorant, flavoring agent, dye, trace element, and vitamin.

16. The composition of claim 15, wherein said at least one additional substance is selected from the group consisting of chlorpyrifos, demeton-S-methyl, disulfoton, ethoprofos, fenitrothion, malathion, parathion, triazophos, amitraz, cypermethrin, deltamethrin, fenpropathrin, fenvalerate, permethrin, aldicarb, carbosulfan, pirimicarb, bendiocarb, teflubenzuron, dicofol, endosulfan, lindane, benzoximate, avermectins, ivermectin, milbemycins, thiophanate, trichlorfon, dichlorvos, diaveridine and dimetridazole.

17. A method of inhibiting a pest GABA receptor, comprising contacting one or more pest GABA receptors with at least one compound of claim 1.

18. A method for controlling pests, comprising contacting an animal, plant or object with a composition comprising:

(a) a pesticidally effective amount of at least one compound of claim 1; and (b) one or more pesticidally-acceptable excipients.

19. The compound of claim 1, wherein said compound is selected from the group consisting of:

2-(2,6-dichloro-4-(trifluoromethyl)phenyl)-2,4,5,6-tetrahydrocyclopenta(c)pyrazole;

2-(2,6-dichloro-4-(trifluoromethyl)phenyl)-6,6-dimethyl-2,4,5,6-tetrahydrocyclopenta(c)pyrazole;

2-(2,6-dichloro-4-(trifluoromethyl)phenyl)-4,5,6,7-tetrahydro-2H-indazole;

2-(2,6-dichloro-4-(trifluoromethyl)phenyl)-2,4,5,6,7,8-hexahydrocyclohepta(c)pyrazole;

2-(2,6-dichloro-4-(trifluoromethyl)phenyl)indeno(1,2-c)pyrazole;

2-(2,6-dichloro-4-(trifluoromethyl)phenyl)-3-methyl-2,4,5,6-tetrahydrocyclopenta(c)pyrazole;

2-(2,6-dichloro-4-(trifluoromethyl)phenyl)-3-methyl-4,5,6,7-tetrahydro-2H-indazole;

3,4-diaza-4-(2,6-dichloro-4-(trifluoromethyl)phenyl)tricyclo(5.2.1.0$^{2.6}$)deca-2,5-diene;

8-(2,6-dichloro-4-(trifluoromethyl)phenyl)-5,5,9-trimethylspiro-(1,3-dioxane)-2,5'-2,4',5,6',7'-tetrahydro-2H-indazole;

2-(2,6-dichloro-4-(trifluoromethyl)phenyl)-2,4,6,7-tetrahydroindazole-5-one;

2-(2,6-dichloro-4-(trifluoromethyl)phenyl)-5-phenyl-4,5,6,7-tetrahydro-2H-indazole;

2-(2,6-dichloro-4-(trifluoromethyl)phenyl)-4,6,6-trimethyl-2,4,5,6-tetrahydrocyclopenta(c)pyrazole;

5,6-diaza-5-(2,6-dichloro-4-(trifluoromethyl)phenyl)tetracyclo-(8.2.1.0$^{2.9}$.0$^{3.7}$)trideca-3,6-diene;

2-(2,6-dichloro-4-(trifluoromethyl)phenyl)-4,4-dimethyl-2,4,5,6-tetrahydrocyclopenta(c)pyrazole;

2-(2,6-dichloro-4-(trifluoromethyl)phenyl)-4-phenyl-2,4,5,6-tetrahydrocyclopenta(c)pyrazole;

2-(2,6-dichloro-4-(trifluoromethyl)phenyl)-4-methyl-2,4,5,6-tetrahydrocyclopenta(c)pyrazole;

and pesticidally acceptable salts thereof.

20. The compound of claim 7, wherein said compound is selected from the group consisting of:

2-(2,6-dichloro-4-(trifluoromethyl)phenyl)-4-hydroxy-2,4,5,6-tetrahydrocyclopenta(c)pyrazole;

2-(2,6-dichloro-4-(trifluoromethyl)phenyl)-4-methoxy-2,4,5,6-tetrahydrocyclopenta(c)pyrazole;

2-(2,6-dichloro-4-(trifluoromethyl)phenyl)-4-trifluoromethoxy-2,4,5,6-tetrahydrocyclopenta(c)pyrazole;

2-(2,6-dichloro-4-(trifluoromethyl)phenyl)-4-methylthio-2,4,5,6-tetrahydrocyclopenta(c)pyrazole;

2-(2,6-dichloro-4-(trifluoromethyl)phenyl)-4-trifluoromethylthio-2,4,5,6-tetrahydrocyclopenta(c)pyrazole;

2-(2,6-dichloro-4-(trifluoromethyl)phenyl)-5,5-difluoro-4-hydroxy-2,4,5,6-tetrahydrocyclopenta(c)pyrazole;

2-(2,6-dichloro-4-(trifluoromethyl)phenyl)-5,5-difluoro-4-methoxy-2,4,5,6-tetrahydrocyclopenta(c)pyrazole;

2-(2,6-dichloro-4-(trifluoromethyl)phenyl)-5,5-difluoro-4-trifluoromethoxy-2,4,5,6-tetrahydrocyclopenta(c)pyrazole;

2-(2,6-dichloro-4-(trifluoromethyl)phenyl)-5,5-difluoro-4-methylthio-2,4,5,6-tetrahydrocyclopenta(c)pyrazole;

2-(2,6-dichloro-4-(trifluoromethyl)phenyl)-5,5-difluoro-4-trifluoromethylthio-2,4,5,6-trihydrocyclopenta(c)pyrazole;

2-(2,6-dichloro-4-(trifluoromethyl)phenyl)-6,6-difluoro-2,4,5,6-tetrahydrocyclopenta(c)pyrazole;

2-(2,6-dichloro-4-(trifluoromethyl)phenyl)-4,4-difluoro-2,4,5,6-tetrahydrocyclopenta(c)pyrazole;

2-(2,6-dichloro-4-(trifluoromethyl)phenyl)-5,5-difluoro-2,4,5,6-tetrahydrocyclopenta(c)pyrazole;

2-(2,6-dichloro-4-(trifluoromethyl)phenyl)-4,4,6,6-tetrafluoro-2,4,5,6-tetrahydrocyclopenta(c)pyrazole; and 2-(2,6-dichloro-4-(trifluoromethyl)phenyl)-4,4,5-trifluoro-2,4,5,6-tetrahydrocyclopenta(c)pyrazole;

and pesticidally acceptable salts thereof.

21. The compound of claim 7, wherein said compound is selected from the group consisting of:

2-(2,6-dichloro-4-(trifluoromethyl)phenyl)-4,4,5,5-tetrafluoro-2,4,5,6-tetrahydrocyclopenta(c)pyrazole;

2-(2,6-dichloro-4-(trifluoromethyl)phenyl)-5,5-difluoro-4-methyl-2,4,5,6-tetrahydrocyclopenta(c)pyrazol-4-ol;

2-(2,6-dichloro-4-(trifluoromethyl)phenyl)-5,5-difluoro-5,6-dihydrocyclopenta(c)pyrazol-4-one;

2-(2,6-dichloro-4-(trifluoromethyl)phenyl)-5,5-difluoro-2,4,5,6-tetrahydrocyclopenta(c)pyrazole;

2-(2,6-dichloro-4-(trifluoromethyl)phenyl)-4,6-dihydrocyclopenta(c)pyrazol-5-one;

2-(2,6-dichloro-4-(trifluoromethyl)phenyl)-4,4,5,6-tetrafluoro-2,4,5,6-tetrahydrocyclopenta(c)pyrazole;

2-(2,6-dichloro-4-(trifluoromethyl)phenyl)-5,6-difluoro-4-methyl-2,4,5,6-tetrahydrocyclopenta(c)pyrazol-4-ol;

2-(2,6-dichloro-4-(trifluoromethyl)phenyl)-5,6-difluoro-5,6-dihydrocyclopenta(c)pyrazol-4-one;

2-(2,6-dichloro-4-(trifluoromethyl)phenyl)-5,6-difluoro-2,4,5,6-tetrahydrocyclopenta(c)pyrazole;

and pesticidally acceptable salts thereof.

* * * * *

UNITED STATES PATENT AND TRADEMARK OFFICE
CERTIFICATE OF CORRECTION

PATENT NO. : 6,545,033 B1  Page 1 of 1
DATED : April 8, 2003
INVENTOR(S) : Dhanoa et al.

It is certified that error appears in the above-identified patent and that said Letters Patent is hereby corrected as shown below:

<u>Column 74,</u>
Line 37, delete "3,4-diaza-4-(2,6-dichloro-4-(trifluoromethyl)phenyl) tricycle(5.2.1.0 $^{2.6}$ )deca-2,5-diene;" and add therefore -- 3,4-diaza-4-(2,6-dichloro-4-(trifluoromethyl)phenyl)tricycle(5.2.1.0 $^{2,6}$)deca-2,5-diene; --
Line 47, delete "5,6-diaza-4-(2,6-dichloro-4-(trifluoromethyl)phenyl)tetracyclo-(8.2.1.0 $^{2.9}$,0 $^{3.7}$)trideca-3,6-diene;" and add therefore -- 5,6-diaza-4-(2,6-dichloro-4-(trifluoromethyl)phenyl)tetracyclo-(8.2.1.0$^{2,9}$,0$^{3,7}$)trideca-3,6-diene; --

Signed and Sealed this

Tenth Day of February, 2004

JON W. DUDAS
*Acting Director of the United States Patent and Trademark Office*